United States Patent
Yao et al.

(10) Patent No.: US 10,513,522 B2
(45) Date of Patent: *Dec. 24, 2019

(54) AZETIDINYL PHENYL, PYRIDYL OR PYRAZINYL CARBOXAMIDE DERIVATIVES AS JAK INHIBITORS

(71) Applicants: Incyte Corporation, Wilmington, DE (US); Incyte Holdings Corporation, Wilmington, DE (US)

(72) Inventors: Wenqing Yao, Chadds Ford, PA (US); David M. Burns, Plymouth Meeting, PA (US); Jincong Zhuo, Garnet Valley, PA (US)

(73) Assignees: Incyte Corporation, Wilmington, DE (US); Incyte Holdings Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/435,735

(22) Filed: Feb. 17, 2017

(65) Prior Publication Data

US 2017/0253598 A1    Sep. 7, 2017

Related U.S. Application Data

(63) Continuation of application No. 14/697,236, filed on Apr. 27, 2015, now Pat. No. 9,611,269, which is a continuation of application No. 14/186,338, filed on Feb. 21, 2014, now Pat. No. 9,023,840, which is a continuation of application No. 13/526,957, filed on Jun. 19, 2012, now Pat. No. 8,691,807.

(60) Provisional application No. 61/591,094, filed on Jan. 26, 2012, provisional application No. 61/498,942, filed on Jun. 20, 2011.

(51) Int. Cl.
    *C07D 487/04* (2006.01)
    *C07D 471/04* (2006.01)

(52) U.S. Cl.
    CPC ......... *C07D 487/04* (2013.01); *C07D 471/04* (2013.01)

(58) Field of Classification Search
    CPC .................................................. C07D 487/04
    See application file for complete search history.

(56) References Cited

U.S. PATENT DOCUMENTS

| | | |
|---|---|---|
| 2,985,589 A | 5/1961 | Broughton et al. |
| 3,832,460 A | 8/1974 | Kosti |
| 4,140,755 A | 2/1979 | Sheth |
| 4,402,832 A | 9/1983 | Gerhold |
| 4,498,991 A | 2/1985 | Oroskar |
| 4,512,984 A | 4/1985 | Seufert et al. |
| 4,548,990 A | 10/1985 | Mueller et al. |
| 4,814,477 A | 3/1989 | Wijnberg et al. |
| 5,378,700 A | 1/1995 | Sakuma et al. |
| 5,472,949 A | 12/1995 | Arasaki |
| 5,510,101 A | 4/1996 | Stroppolo |
| 5,521,184 A | 5/1996 | Zimmermann |
| 5,630,943 A | 5/1997 | Grill |
| 5,795,909 A | 8/1998 | Shashoua et al. |
| 5,856,326 A | 1/1999 | Anthony |
| 5,919,779 A | 7/1999 | Proudfoot et al. |
| 6,025,366 A | 2/2000 | Walsh et al. |
| 6,060,038 A | 5/2000 | Burns |
| 6,075,056 A | 6/2000 | Quigley, Jr. et al. |
| 6,136,198 A | 10/2000 | Adam et al. |
| 6,217,895 B1 | 4/2001 | Guo et al. |
| 6,335,342 B1 | 1/2002 | Longo et al. |
| 6,375,839 B1 | 4/2002 | Adam et al. |
| 6,413,419 B1 | 7/2002 | Adam et al. |
| 6,486,322 B1 | 11/2002 | Longo et al. |
| 6,518,265 B1 | 2/2003 | Kato et al. |
| 6,548,078 B2 | 4/2003 | Guo |
| 6,569,443 B1 | 5/2003 | Dawson |
| 6,579,882 B2 | 6/2003 | Stewart et al. |
| 6,624,138 B1 | 9/2003 | Sung et al. |
| 6,635,762 B1 | 10/2003 | Blumenkopf et al. |
| 6,712,973 B2 | 3/2004 | Adam et al. |
| 6,713,089 B1 | 3/2004 | Bertelsen et al. |
| 6,852,727 B2 | 2/2005 | Goulet et al. |
| 6,953,776 B2 | 10/2005 | Di Napoli |
| 7,005,436 B2 | 2/2006 | Lloyd et al. |
| 7,167,750 B2 | 1/2007 | Knudson et al. |
| 7,265,108 B2 | 9/2007 | Ozaki |

(Continued)

FOREIGN PATENT DOCUMENTS

| | | |
|---|---|---|
| CN | 102026999 | 4/2011 |
| CN | 102985417 | 3/2013 |

(Continued)

OTHER PUBLICATIONS

Clark, James, D., et al. "Discovery and Development of Janus Kinase (JAK) Inhibitors for Inflammatory Diseases." Journal of Medicinal Chemistry. (Perspective). Jan. 13, 2014. pp. A-P. (Year: 2014).*
Parks, Deborah L. "Tofacitinib and Other Kinase Inhibitors Offer New Approach to Treating Rheumatoid Arthritis." The Rheumatologist. Jun. 2013, pp. 1-12. (Year: 2013).*
Men's Health. "Prostate cancer prevention: What you can do." (Dec. 6, 2008). (Year: 2008).*
Norman, P. "Selective JAK1 inhibitor and selective Tyk2 inhibitor patents." Expert Opinion. Informa Healthcare. Published 2012. Available at: < http://informahealthcare.com/doi/pdfplus/10.1517/13543776.2012.723693 >. (Year: 2012).*
Bock, C., et al. "Managing drug resistance in cancer: lessons from HIV therapy." Nature. (Jul. 2012), vol. 12, pp. 494-501. (Year: 2012).*

(Continued)

*Primary Examiner* — Andrew D Kosar
*Assistant Examiner* — John S Kenyon
(74) *Attorney, Agent, or Firm* — Fish & Richardson P.C.

(57) ABSTRACT

The present invention provides azetidinyl phenyl, pyridyl, or pyrazinyl carboxamide derivatives, as well as their compositions and methods of use, that modulate the activity of Janus kinase (JAKs) and are useful in the treatment of diseases related to the activity of JAK including, for example, inflammatory disorders, autoimmune disorders, cancer, and other diseases.

25 Claims, No Drawings

(56) References Cited

U.S. PATENT DOCUMENTS

| | | |
|---|---|---|
| 7,335,667 B2 | 2/2008 | Rodgers et al. |
| 7,358,255 B2 | 4/2008 | Nakamura |
| 7,517,870 B2 | 4/2009 | Auricchio |
| 7,598,257 B2 | 10/2009 | Rodgers et al. |
| 7,683,171 B2 | 3/2010 | Pitts et al. |
| 7,745,437 B2 | 6/2010 | Ren et al. |
| 7,750,007 B2 | 7/2010 | Bearss et al. |
| 7,834,022 B2 | 11/2010 | Rodgers et al. |
| 8,053,433 B2 | 11/2011 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,420,629 B2 | 4/2013 | Rodgers et al. |
| 8,440,679 B2 | 5/2013 | McAllister |
| 8,445,488 B2 | 5/2013 | Rodger et al. |
| 8,486,902 B2 | 7/2013 | Rodgers et al. |
| 8,513,270 B2 | 8/2013 | Arvanitis et al. |
| 8,530,485 B2 | 9/2013 | Rodgers et al. |
| 8,541,425 B2 | 9/2013 | Rodgers et al. |
| 8,563,541 B2 | 10/2013 | Arvanitis et al. |
| 8,604,043 B2 | 12/2013 | Li et al. |
| 8,637,529 B2 | 1/2014 | Woller |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,835,423 B2 | 9/2014 | Arvanitis et al. |
| 8,841,318 B2 | 9/2014 | Arvanitis et al. |
| 8,883,806 B2 | 11/2014 | Zhou et al. |
| 8,889,697 B2 | 11/2014 | Rodgers et al. |
| 8,933,085 B2 | 1/2015 | Rodgers et al. |
| 8,933,086 B2 | 1/2015 | Rodgers et al. |
| 8,946,245 B2 | 2/2015 | Rodgers et al. |
| 8,987,442 B2 | 3/2015 | Tung et al. |
| 8,987,443 B2 | 3/2015 | Liu |
| 8,993,582 B2 | 3/2015 | Zhou et al. |
| 9,000,161 B2 | 4/2015 | Zhou et al. |
| 9,023,840 B2 | 5/2015 | Yao et al. |
| 9,034,884 B2 | 5/2015 | Rodgers et al. |
| 9,079,912 B2 | 7/2015 | Rodgers et al. |
| 9,090,611 B2 | 7/2015 | Rodgers et al. |
| 9,181,271 B2 | 11/2015 | Li et al. |
| 9,206,187 B2 | 12/2015 | Rodgers et al. |
| 9,216,984 B2 | 12/2015 | Li |
| 9,221,845 B2 | 12/2015 | Cao |
| 9,290,506 B2 | 3/2016 | Zhou et al. |
| 9,334,274 B2 | 5/2016 | Rodgers |
| 9,359,358 B2 | 6/2016 | Rodgers |
| 9,376,439 B2 | 6/2016 | Rodgers |
| 9,487,521 B2 | 11/2016 | Zhou et al. |
| 9,498,467 B2 | 11/2016 | Leopold et al. |
| 9,464,088 B2 | 12/2016 | Huang |
| 9,611,269 B2 | 4/2017 | Yao et al. |
| 9,623,029 B2 | 4/2017 | Li et al. |
| 9,655,854 B2 | 5/2017 | Yeleswaram |
| 9,974,790 B2 | 5/2018 | Rodgers et al. |
| 9,999,619 B2 | 6/2018 | Huang et al. |
| 2002/0111353 A1 | 8/2002 | Ledeboer et al. |
| 2003/0064969 A1 | 4/2003 | Bhagwat et al. |
| 2003/0100756 A1 | 5/2003 | Adams et al. |
| 2003/0144309 A1 | 7/2003 | Choon-Moon |
| 2003/0165576 A1 | 9/2003 | Fujii et al. |
| 2004/0009222 A1 | 1/2004 | Chou et al. |
| 2004/0009983 A1 | 1/2004 | Cox et al. |
| 2004/0029857 A1 | 2/2004 | Hale et al. |
| 2004/0077654 A1 | 4/2004 | Bouillot |
| 2004/0099204 A1 | 5/2004 | Nestor |
| 2004/0198737 A1 | 10/2004 | Cox et al. |
| 2004/0204404 A1 | 10/2004 | Zelle |
| 2004/0214928 A1 | 10/2004 | Aronov |
| 2004/0235862 A1 | 11/2004 | Burns |
| 2005/0014966 A1 | 1/2005 | Tabe |
| 2005/0054568 A1 | 3/2005 | Ling |
| 2005/0153989 A1 | 7/2005 | Grotzfeld et al. |
| 2006/0004010 A1 | 1/2006 | Habashita et al. |
| 2006/0020011 A1 | 1/2006 | Wu et al. |
| 2006/0079511 A1 | 4/2006 | Liu et al. |
| 2006/0106020 A1 | 5/2006 | Rodgers et al. |
| 2006/0106027 A1 | 5/2006 | Furet et al. |
| 2006/0128803 A1 | 6/2006 | Klimko |
| 2006/0135537 A1 | 6/2006 | Knegtel et al. |
| 2006/0178393 A1 | 8/2006 | Pitts |
| 2006/0183761 A1 | 8/2006 | Ledeboer et al. |
| 2006/0183906 A1 | 8/2006 | Rodgers et al. |
| 2006/0223864 A1 | 10/2006 | Biju |
| 2006/0293311 A1 | 12/2006 | Li et al. |
| 2007/0135461 A1 | 6/2007 | Rodgers et al. |
| 2007/0135466 A1 | 6/2007 | Ledeboer et al. |
| 2007/0149506 A1 | 6/2007 | Arvanitis et al. |
| 2007/0149561 A1 | 6/2007 | Dhanak et al. |
| 2007/0191364 A1 | 8/2007 | Braun et al. |
| 2007/0191405 A1 | 8/2007 | Noronha |
| 2007/0208053 A1 | 9/2007 | Wang et al. |
| 2007/0225286 A1 | 9/2007 | Ren et al. |
| 2007/0259904 A1 | 11/2007 | Noronha |
| 2008/0021026 A1 | 1/2008 | Borchardt et al. |
| 2008/0085898 A1 | 4/2008 | Lu |
| 2008/0096852 A1 | 4/2008 | Yanni |
| 2008/0119496 A1 | 5/2008 | Ohlmeyer |
| 2008/0161346 A1 | 7/2008 | Cheng |
| 2008/0188500 A1 | 8/2008 | Arvanitis et al. |
| 2008/0194468 A1 | 8/2008 | Bodor |
| 2008/0207570 A1 | 8/2008 | Segura-Orsoni |
| 2008/0207584 A1 | 8/2008 | Habashita et al. |
| 2008/0280876 A1 | 11/2008 | Hobson et al. |
| 2008/0312258 A1 | 12/2008 | Rodgers et al. |
| 2008/0312259 A1 | 12/2008 | Rodgers et al. |
| 2009/0018156 A1 | 1/2009 | Tang et al. |
| 2009/0076070 A1 | 3/2009 | Harada et al. |
| 2009/0088445 A1 | 4/2009 | Ledeboer et al. |
| 2009/0131403 A1 | 5/2009 | Kusuda |
| 2009/0181959 A1 | 7/2009 | Rodgers et al. |
| 2009/0197869 A1 | 8/2009 | Arvanitis et al. |
| 2009/0203637 A1 | 8/2009 | Hocek et al. |
| 2009/0215766 A1 | 8/2009 | Rodgers et al. |
| 2009/0221608 A1 | 9/2009 | Cui et al. |
| 2009/0233903 A1 | 9/2009 | Rodgers et al. |
| 2009/0318405 A1 | 12/2009 | Li et al. |
| 2010/0022522 A1 | 1/2010 | Rodgers et al. |
| 2010/0069381 A1 | 3/2010 | Itoh et al. |
| 2010/0113416 A1 | 5/2010 | Friedman et al. |
| 2010/0190981 A1 | 7/2010 | Zhou et al. |
| 2010/0210627 A1 | 8/2010 | Mao et al. |
| 2010/0298334 A1 | 11/2010 | Rodgers et al. |
| 2010/0298355 A1 | 11/2010 | Li et al. |
| 2011/0059951 A1 | 3/2011 | Rodgers et al. |
| 2011/0082159 A1 | 4/2011 | Rodgers et al. |
| 2011/0086810 A1 | 4/2011 | Rodgers et al. |
| 2011/0086835 A1 | 4/2011 | Rodgers et al. |
| 2011/0201593 A1 | 8/2011 | Babu et al. |
| 2011/0207754 A1 | 8/2011 | Li et al. |
| 2011/0223210 A1 | 9/2011 | Rodgers et al. |
| 2011/0224157 A1 | 9/2011 | Rodgers et al. |
| 2011/0224190 A1 | 9/2011 | Huang et al. |
| 2011/0288107 A1 | 11/2011 | Rarikh et al. |
| 2012/0014989 A1 | 1/2012 | Rodgers |
| 2012/0077798 A1 | 3/2012 | Rodgers et al. |
| 2012/0149681 A1 | 6/2012 | Rodgers |
| 2012/0149682 A1 | 6/2012 | Rodgers et al. |
| 2012/0214825 A1 | 8/2012 | Vannucchi et al. |
| 2012/0225057 A1 | 9/2012 | Flynn |
| 2012/0252779 A1 | 10/2012 | Ramsden |
| 2012/0301464 A1 | 11/2012 | Friedman et al. |
| 2012/0329782 A1 | 12/2012 | Arvanitis et al. |
| 2013/0018034 A1 | 1/2013 | Yao et al. |
| 2013/0040973 A1 | 2/2013 | Vannucchi et al. |
| 2013/0045963 A1 | 2/2013 | Rodgers et al. |
| 2013/0060026 A1 | 3/2013 | Zhou et al. |
| 2013/0137681 A1 | 5/2013 | Rodgers et al. |

(56) References Cited

U.S. PATENT DOCUMENTS

| | | |
|---|---|---|
| 2013/0225556 A1 | 8/2013 | Rodgers et al. |
| 2013/0253190 A1 | 9/2013 | Zhou et al. |
| 2013/0253191 A1 | 9/2013 | Zhou et al. |
| 2013/0253193 A1 | 9/2013 | Zhou et al. |
| 2013/0274257 A1 | 10/2013 | Arvanitis et al. |
| 2013/0296299 A1 | 11/2013 | Rodgers et al. |
| 2014/0004516 A1 | 1/2014 | Sattler et al. |
| 2014/0005166 A1 | 1/2014 | Rodgers et al. |
| 2014/0005210 A1 | 1/2014 | Rodgers et al. |
| 2014/0018374 A1 | 1/2014 | Rodgers et al. |
| 2014/0031344 A1 | 1/2014 | Arvanitis et al. |
| 2014/0073657 A1 | 3/2014 | Li et al. |
| 2014/0094477 A1 | 4/2014 | Rodgers et al. |
| 2014/0121198 A1 | 5/2014 | Li et al. |
| 2014/0135350 A1 | 5/2014 | Ni et al. |
| 2014/0171409 A1 | 6/2014 | Yao et al. |
| 2014/0221379 A1 | 8/2014 | Rodgers et al. |
| 2014/0228346 A1 | 8/2014 | Rodgers et al. |
| 2014/0243360 A1 | 8/2014 | Rodgers et al. |
| 2014/0256941 A1 | 9/2014 | Liu et al. |
| 2014/0275031 A1 | 9/2014 | Huang et al. |
| 2014/0303196 A1 | 10/2014 | Rodgers et al. |
| 2014/0343030 A1 | 11/2014 | Li et al. |
| 2014/0378400 A1 | 12/2014 | Rodgers et al. |
| 2015/0065447 A1 | 3/2015 | Sandor |
| 2015/0065484 A1 | 3/2015 | Yeleswaram et al. |
| 2015/0087632 A1 | 3/2015 | Rodgers et al. |
| 2015/0087662 A1 | 3/2015 | Li et al. |
| 2015/0152117 A1 | 6/2015 | Gibbons |
| 2015/0164900 A1 | 6/2015 | Rodgers et al. |
| 2015/0183805 A1 | 7/2015 | Liu et al. |
| 2015/0225411 A1 | 8/2015 | Yao et al. |
| 2015/0225412 A1 | 8/2015 | Brameld |
| 2015/0238492 A1 | 8/2015 | Rodgers et al. |
| 2015/0246046 A1 | 9/2015 | Vaddi |
| 2015/0250790 A1 | 9/2015 | Parikh et al. |
| 2015/0315185 A1 | 11/2015 | Rodgers et al. |
| 2015/0342952 A1 | 12/2015 | Leopold |
| 2015/0344497 A1 | 12/2015 | Zhou et al. |
| 2016/0000795 A1 | 1/2016 | Scherle |
| 2016/0015695 A1 | 1/2016 | Li et al. |
| 2016/0024109 A1 | 1/2016 | Li |
| 2016/0067253 A1 | 3/2016 | Li et al. |
| 2016/0272648 A1 | 9/2016 | Rodgers et al. |
| 2016/0346286 A1 | 12/2016 | Rodgers et al. |
| 2016/0347734 A1 | 12/2016 | Liu et al. |
| 2017/0015674 A1 | 1/2017 | Zhou et al. |
| 2017/0071947 A1 | 3/2017 | Rodgers et al. |
| 2017/0087158 A1 | 3/2017 | Friedman et al. |
| 2017/0246157 A1 | 8/2017 | Huang et al. |
| 2017/0319487 A1 | 11/2017 | Yeleswaram et al. |
| 2018/0338978 A1 | 11/2018 | Rodgers et al. |
| 2018/0353499 A1 | 12/2018 | Huang et al. |

FOREIGN PATENT DOCUMENTS

| | | |
|---|---|---|
| DE | 30 36 390 | 5/1982 |
| EP | 0223420 | 5/1987 |
| EP | 0727217 | 8/1996 |
| EP | 0795556 | 9/1997 |
| JP | 07-010876 | 1/1995 |
| JP | 2003/155285 | 5/2003 |
| JP | 2006-502183 | 1/2006 |
| JP | 2006/518341 | 8/2006 |
| JP | 2008-508241 | 3/2008 |
| JP | 2008-545660 | 12/2008 |
| JP | 2009-504619 | 2/2009 |
| JP | 2010-529209 | 8/2010 |
| WO | WO 96/030343 | 10/1996 |
| WO | WO 97/002262 | 1/1997 |
| WO | WO 97/002266 | 1/1997 |
| WO | WO 97/036587 | 10/1997 |
| WO | WO 97/038664 | 10/1997 |
| WO | WO 97/045412 | 12/1997 |
| WO | WO 98/044797 | 10/1998 |
| WO | WO 98/051391 | 11/1998 |
| WO | WO 99/000654 | 1/1999 |
| WO | WO 99/062908 | 12/1999 |
| WO | WO 99/065908 | 12/1999 |
| WO | WO 99/065909 | 12/1999 |
| WO | WO 00/009495 | 2/2000 |
| WO | WO 00/051614 | 9/2000 |
| WO | WO 00/053595 | 9/2000 |
| WO | WO 00/063168 | 10/2000 |
| WO | WO 01/014402 | 3/2001 |
| WO | WO 01/027104 | 4/2001 |
| WO | WO 01/042246 | 6/2001 |
| WO | WO 01/064655 | 9/2001 |
| WO | WO 01/081345 | 11/2001 |
| WO | WO 2001/081346 | 11/2001 |
| WO | WO 01/098344 | 12/2001 |
| WO | WO 02/000196 | 1/2002 |
| WO | WO 02/000661 | 1/2002 |
| WO | WO 02/046184 | 6/2002 |
| WO | WO 02/055084 | 7/2002 |
| WO | WO 02/055496 | 7/2002 |
| WO | WO 02/060492 | 8/2002 |
| WO | WO 02/080926 | 10/2002 |
| WO | WO 02/092573 | 11/2002 |
| WO | WO 02/096909 | 12/2002 |
| WO | WO 03/000695 | 1/2003 |
| WO | WO 2003/000688 | 1/2003 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/092595 | 11/2003 |
| WO | WO 03/099771 | 12/2003 |
| WO | WO 03/099796 | 12/2003 |
| WO | WO 04/003026 | 1/2004 |
| WO | WO 04/005281 | 1/2004 |
| WO | WO 04/005282 | 1/2004 |
| WO | WO 04/026406 | 4/2004 |
| WO | WO 04/041814 | 5/2004 |
| WO | WO 04/046120 | 6/2004 |
| WO | WO 04/047843 | 6/2004 |
| WO | WO 04/056786 | 7/2004 |
| WO | WO 04/072063 | 8/2004 |
| WO | WO 04/080980 | 9/2004 |
| WO | WO 04/092154 | 10/2004 |
| WO | WO 04/099204 | 11/2004 |
| WO | WO 04/099205 | 11/2004 |
| WO | WO 05/005988 | 1/2005 |
| WO | WO 05/013986 | 2/2005 |
| WO | WO 05/020921 | 3/2005 |
| WO | WO 05/026129 | 3/2005 |
| WO | WO 05/028444 | 3/2005 |
| WO | WO 05/049033 | 6/2005 |
| WO | WO 05/051393 | 6/2005 |
| WO | WO 05/060972 | 7/2005 |
| WO | WO 05/061463 | 7/2005 |
| WO | WO 05/062795 | 7/2005 |
| WO | WO 05/089502 | 9/2005 |
| WO | WO 05/095400 | 10/2005 |
| WO | WO 05/105146 | 11/2005 |
| WO | WO 05/105814 | 11/2005 |
| WO | WO 05/105988 | 11/2005 |
| WO | WO 05/110410 | 11/2005 |
| WO | WO 05/117909 | 12/2005 |
| WO | WO 05/121130 | 12/2005 |
| WO | WO 05/123719 | 12/2005 |
| WO | WO 06/004984 | 1/2006 |
| WO | WO 06/013114 | 2/2006 |
| WO | WO 06/022459 | 3/2006 |
| WO | WO 06/039718 | 4/2006 |
| WO | WO 06/046023 | 5/2006 |
| WO | WO 06/046024 | 5/2006 |
| WO | WO 06/052913 | 5/2006 |
| WO | WO 06/056399 | 6/2006 |
| WO | WO 06/067445 | 6/2006 |
| WO | WO 06/069080 | 6/2006 |
| WO | WO 06/077499 | 7/2006 |
| WO | WO 06/096270 | 9/2006 |
| WO | WO 06/101783 | 9/2006 |

(56) References Cited

FOREIGN PATENT DOCUMENTS

| | | |
|---|---|---|
| WO | WO 06/108103 | 10/2006 |
| WO | WO 06/122806 | 11/2006 |
| WO | WO 06/127587 | 11/2006 |
| WO | WO 06/129199 | 12/2006 |
| WO | WO 06/136823 | 12/2006 |
| WO | WO 07/002433 | 1/2007 |
| WO | WO 07/025090 | 3/2007 |
| WO | WO 07/041130 | 4/2007 |
| WO | WO 07/043677 | 4/2007 |
| WO | WO 07/044894 | 4/2007 |
| WO | WO 2007/044050 | 4/2007 |
| WO | WO 07/049041 | 5/2007 |
| WO | WO 07/062459 | 6/2007 |
| WO | WO 07/070514 | 6/2007 |
| WO | WO 07/076423 | 7/2007 |
| WO | WO 07/077949 | 7/2007 |
| WO | WO 07/084557 | 7/2007 |
| WO | WO 07/090141 | 8/2007 |
| WO | WO 07/090748 | 8/2007 |
| WO | WO 07/116313 | 10/2007 |
| WO | WO 07/117494 | 10/2007 |
| WO | WO 07/129195 | 11/2007 |
| WO | WO 07/135461 | 11/2007 |
| WO | WO 07/140222 | 12/2007 |
| WO | WO 08/013925 | 1/2008 |
| WO | WO 08/028937 | 3/2008 |
| WO | WO 08/035376 | 3/2008 |
| WO | WO 08/043031 | 4/2008 |
| WO | WO 08/058126 | 5/2008 |
| WO | WO 08/064157 | 5/2008 |
| WO | WO 08/067119 | 6/2008 |
| WO | WO 08/077712 | 7/2008 |
| WO | WO 08/079291 | 7/2008 |
| WO | WO 08/079292 | 7/2008 |
| WO | WO 08/082198 | 7/2008 |
| WO | WO 08/082839 | 7/2008 |
| WO | WO 08/082840 | 7/2008 |
| WO | WO 08/106692 | 9/2008 |
| WO | WO 08/124323 | 10/2008 |
| WO | WO 08/139161 | 11/2008 |
| WO | WO 08/145681 | 12/2008 |
| WO | WO 08/145688 | 12/2008 |
| WO | WO 08/157207 | 12/2008 |
| WO | WO 08/157208 | 12/2008 |
| WO | WO 09/007839 | 1/2009 |
| WO | WO 09/016460 | 2/2009 |
| WO | WO 09/049028 | 4/2009 |
| WO | WO 09/064486 | 5/2009 |
| WO | WO 09/064835 | 5/2009 |
| WO | WO 09/071577 | 6/2009 |
| WO | WO 09/100130 | 8/2009 |
| WO | WO 09/109576 | 9/2009 |
| WO | WO 09/114512 | 9/2009 |
| WO | WO 09/115572 | 9/2009 |
| WO | WO 09/158687 | 12/2009 |
| WO | WO 10/000978 | 1/2010 |
| WO | WO 10/001169 | 1/2010 |
| WO | WO 10/020905 | 2/2010 |
| WO | WO 10/022076 | 2/2010 |
| WO | WO 10/022081 | 2/2010 |
| WO | WO 10/026121 | 3/2010 |
| WO | WO 10/026122 | 3/2010 |
| WO | WO 10/026124 | 3/2010 |
| WO | WO 10/039939 | 4/2010 |
| WO | WO 10/081692 | 7/2010 |
| WO | WO 10/083283 | 7/2010 |
| WO | WO 10/135621 | 11/2010 |
| WO | WO 10/135650 | 11/2010 |
| WO | WO 11/025685 | 3/2011 |
| WO | WO 11/028685 | 3/2011 |
| WO | WO 11/029802 | 3/2011 |
| WO | WO 11/031554 | 3/2011 |
| WO | WO 11/035900 | 3/2011 |
| WO | WO 11/044481 | 4/2011 |
| WO | WO 11/057784 | 5/2011 |
| WO | WO 11/069141 | 6/2011 |
| WO | WO 2011/066369 | 6/2011 |
| WO | WO 11/112662 | 9/2011 |
| WO | WO 11/130146 | 10/2011 |
| WO | WO 11/144338 | 11/2011 |
| WO | WO 11/146808 | 11/2011 |
| WO | WO 12/003457 | 1/2012 |
| WO | WO 2012/045010 | 4/2012 |
| WO | WO 12/068440 | 5/2012 |
| WO | WO 12/068450 | 5/2012 |
| WO | WO 2012/071612 | 6/2012 |
| WO | WO 12/177606 | 12/2012 |
| WO | WO 13/023119 | 2/2013 |
| WO | WO 13/026025 | 2/2013 |
| WO | WO 13/036611 | 3/2013 |
| WO | WO 13/173720 | 11/2013 |
| WO | WO 14/138168 | 9/2014 |
| WO | WO 2014/186706 | 11/2014 |
| WO | WO-2015184305 A1 * | 12/2015 ............... A61K 9/00 |
| WO | WO 2015/184087 | 4/2018 |

OTHER PUBLICATIONS

Mayo Clinic. "Pancreatic cancer." © 2014. Available at: < http://www.mayoclinic.com/health/pancreatic-cancer/DS00357 >. (Year: 2014).*

Lucet, Isabel, et al. "The structural basis of Janus kinase 2 inhibition by a potent and specific pan-Janus kinase inhibitor." Blood. (2006), vol. 107, No. 1, pp. 176-183. (Year: 2006).*

Mandal, A. "Cancer Classification." © 2014. Available from: < http://www.news-medical.net/health/Cancer-Classification.aspx >. (Year: 2014).*

American Cancer Society. "Breast Cancer." (2014), Accessed Nov. 9, 2018. Available from: < https://www.cancer.org/cancer/breast-cancer/risk-and-prevention.html > . (Year: 2014).*

NavigatingCancer.com. "List of Cancer Chemotherapy Drugs." (2013). Accessed Nov. 9, 2018. Available from: < https://www.navigatingcare.com/library/all/chemotherapy_drugs >. (Year: 2013).*

Mayo Clinic. "Pancreatic Cancer." (Apr. 10, 2012). Accessed Nov. 9, 2018. Available from: < https://www.mayoclinic.org/diseases-conditions/pancreatic-cancer/symptoms-causes/syc-20355421?p=1 > . (Year: 2012).*

UCSF Medical Center. "Liver Cancer." (Mar. 8, 2005), Accessed Nov. 9, 2018. Available from: < https://www.ucsfhealth.org/conditions/liver_cancer/ >. (Year: 2005).*

OrthoInfo. "Osteoporosis." (Feb. 2001). Accessed Dec. 15, 2018. Available from: < https://orthoinfo.aaos.org/en/diseases--conditions/osteoporosis/ > . (Year: 2001).*

Cleveland Clinic. "Lupus." (Feb. 2001). Accessed Dec. 15, 2018. Available from: < https://my.clevelandclinic.org/health/diseases/4875-lupus >. (Year: 2001).*

National Cancer Institute. "Cancer Types by Site." (Mar. 14, 2011). Accessed Dec. 8, 2018. Available from: < https://web.archive.org/web/20110314030905/https://training.seer.cancer.gov/disease/categories/site.html > . (Year: 2011).*

Mayo Clinic. "Heart Transplant." (2018). Accessed Dec. 8, 2018. Available from: < https://www.mayoclinic.org/tests-procedures/heart-transplant/about/pac-20384750 >. (Year: 2018).*

26th Annual JPMorgan Healthcare Conference presentation dated Jan. 8, 2008, 28 pages.

Abe et al., "Effective Methods for Introducing Some Aryl and Heteroaryl Substituent onto 1-Azaazulene Nuclei", Heterocycles, 2005, 66: 229-240.

Abelson et al., "Alternate reference values for tear film break-up time in normal and dry eye populations, Lacrimal Gland, Tear Film, and Dry Eye Syndromes 3 Part B", Adv Exp Med Biol, 2002, 506: 1121-1125.

Abelson et al., "Dry eye syndrome: diagnosis, clinical trials, and pharmaceutical treatment—'improving clinical trials'. Lacrimal Gland, Tear Film, and Dry Eye Syndromes 3 Part B", Adv Exp Med Biol, 2002, 506:1079-86.

Abstract of Chilean patent application No. 3496-06 published in Official Gazette of the Republic of Chile (Jun. 1, 2007) and publication (2 pages).

(56) References Cited

OTHER PUBLICATIONS

Ahmed et al., "Treatment of Pemphigus Vulgaris with Rituximab and Intravenous Immune Globulin," The New England Journal of Medicine, 2006, 1772-1779.
Aho et al., Expression of human pim family genes is selectively up-regulated by cytokines promoting T helper type 1, but not T helper type 2, cell differentiation, Immunology, 2005, 116: 82-88.
Albach et al., "Diagnosis of keratoconjunctivitis sicca in rheumatoid arthritis. The value of various tests", Ophthalmologe, Apr. 1994; 91(2):229-34—in German (with English abstract/summary contained therein).
Anderson et al., "Biochemical characterization of GSK1070916, a potent and selective inhibitor of Aurora B and Aurora C kinases with an extremely long residence time", Biochem. J., 2009, 420(2): 259-265.
Anonymous, "Ruxolitinib for Patients with Low or Intermediate-1 Risk Myelodysplastic Syndrome (MDS)," ClinicalTrials.gov archive, Aug. 2013, XP002739581, Retrieved from the Internet: URL: clinicaltrials.gov/archive/NCT01895842/2013_08_19 [retrieved on Apr. 30, 2015], 5 pages.
Bachmann et al., "The serine/threonine kinase Pim-1," The International Journal of Biochemistry and Cell Biology, 2005, 37: 726-730.
Bain, et al., "Chronic neutrophilic leukaemia," in: Swerdlow, et al., eds. WHO Classification of Tumors of Haematopoietic and Lymphoid Tissues (ed 4th). Lyon: IARC Press, 2008: 38-39.
Banker et al., "Modern Pharmaceuticals" Third Edition, 1996, 596.
Bambino et al., "Tear film and ocular surface tests in animal models of dry eye; uses and limitations," Experimental Eye Research, 2004, 79: 613-621.
Barr et al., "Corneal scarring in the Collaborative Longitudinal Evaluation of Keratoconus (CLEK) Study: baseline prevalence and repeatability of detection", Cornea, 1999, 18(1):34-46.
Baudouin et al., "Flow cytometry in impression cytology specimens. A new method for evaluation of conjunctival Inflammation," Invest Ophthalmol Vis Sci, 1997, 38: 1458-1464.
Baxter et al., "Acquired mutation of the tyrosine kinase JAK2 in human myeloproliferative disorders," Lancet., 2005, 365:1054-1061.
Baxter et al., "Reductive Amination of Carbonyl Compounds with Borohydride and Bornane Reducing Agents," Organic Reactions, 2002, 1-57.
Baytel et al., "The human Pim-2 proto-oncogene and its testicular expression," Biochimica et Biophysica Acta, 1998, 1442: 274-285.
Beck et al., "Brief Report: Alleviation of Systemic Manifestations of Castleman's Disease by Monoclonal Anti-Interleukin-6 Antibody," N. Engl. J. Med., 1994, 330(9):602-605.
Begley et al., "Use of the dry eye questionnaire to measure symptoms of ocular irritation in patients with aqueous tear deficient dry eye", Cornea, 2002, 21: 664-70.
Bell and Zalay, "Synthesis of Substituted 3-Amino[6, 5-b] triazinoindoles." Journal of Heterocyclic Chemistry, Oct. 1975, 12(5):1001-1004.
Bennett et al., "Proposals for the classification of the myelodysplastic syndromes," British Journal of Haematology, 1982, 51: 189-199.
Berge et al., "Pharmaceutical salts", J. Pharma. Science, 1977, 66(1): 1-19.
Beyer, "Uber die Synthese von 2-Methylmercapto-1,3,4-thiodiazinen und deren Umlagerung in Pyrazolderivate (The synthesis of 2-methylthio-1,3,4-thiadiazines and their rearrangement to pyrazole derivatives)", Chem. Berichte Jahrg., 92:2593-2599 (1959) (abstract provided).
Bhattacharya et al., "Polymorphism in Pharmaceutical Solids," Second Edition, 2009, 192:327-345.
Bhovi, et al., "1,3-Dipolar Cycloaddition Reaction: Synthesis and Antimicrobial, Activity of Some New 3-Ethoxycarbonyl-s-Methoxy-6-Bromo-2-Triazolylmethylindoles", Indian Journal of Heterocyclic Chemistry, Jul.-Sep. 2004, 14: 15-18.

Bioreversible Carriers in Drug Design, ed. Edward B. Roche, American Pharmaceutical Association and Pergamon Press, 1987 **Too Voluminous to Provide.
Blom, "Two-Pump at-Column-Dilution Configuration for Preparative Liquid Chromatography—Mass Spectrometry," J. Comb. Chem., 2002, 4: 295-301.
Blom et al., "Optimizing Preparative LC/MS Configurations and Methods for Parallel Synthesis Purification," J. Comb. Chem., 2003, 5: 670-683.
Blom et al., "Preparative LC-MS Purification: Improved Compound-Specific Method Optimization," J. Comb. Chem., 2004, 6: 874-883.
Blume-Jensen et al, "Oncogenic kinase signaling", Nature, 2001, 411(6835):355-365.
Bock et al. "Managing drug resistance in cancer: lessons from HIV therapy." Nature, Jul. 2012, 12: 494-501.
Bolen, "Nonreceptor tyrosine protein kinases", Oncogene, 1993, 8(8):2025-31.
Bollmth et al., "gp130-Mediated Stat3 Activation in Enterocytes Regulates Cell Survival and Cell-Cycle Progression during Colitis-Associated Tumorigenesis," Cancer Cell, 2009, 15:91-102.
Borie et al., "Combined Use of the Jak3 Inhibitor CP-690, 550 with Mycophenolate Mofetil to Prevent Kidney Allograft Rejection in Nonhuman Primates", Transplantation, Dec. 2005, 80(12):1756-64.
Bosworth, "JAK1/JAK2 Inhibitor Ruxolitinib Is a Rising Start," Clinical Oncology, Apr. 2011, 06:04, 3 pages.
Boudny et al., "JAK/STAT signaling pathways and cancer," Neoplasm, 2002, 49:349-355.
Bourcier et al., "Expression of CD40 and CD40 ligand in the human conjunctival epithelium", Invest Ophthalmol Vis Sci, 2000, 41:120-126.
Bowman et al. "STATs in oncogenesis", Oncogene, 2000, 19:2474-2488.
Brett et al., "Structural chemistry of polycyclic heteroaromatic compound. Part 4. Electronic structures of angular dithienopyridines," J Chem Soc, Perkin Trans 2, Jan. 1, 1994, 9:2045.
Brignole et al., "Expression of Fas-Fas Ligand Antigens and Apoptotic Marker AP02-7 by the Human Conjunctival Epithelium. Positive correlation with class II HLA DR expression in inflammatory Ocular Surface Disorders", Exp Eye Res, 1998, 67:687-697.
Brignole et al., "Flow cytometric analysis of inflammatory markers in conjunctival epithelial cells of patients with dry eyes," Invest Ophthalmol Vis Sci, 2000, 41:1356-1363.
Brignole et al., "Flow cytometric analysis of inflammatory markers in KCS: 6-month treatment with topical cyclosporin A," Invest Ophthalmol Vis Sci, 2001, 42:90-95.
Brignole et al., "Flow cytometry in conjunctival impression cytology: a new tool for exploring ocular surface pathologies," Exp Eye Res, 2004, 78:473-481.
Bromberg et al., "Inflammation and Cancer: IL-6 and STAT3 Complete the Link," Cancer Cell, 2009, 15:79-80.
Bron et al., "Grading of corneal and conjunctival staining in the context of other dry eye tests", Cornea, 2003, 22(7):640-50.
Bron et al., "Methodologies to Diagnose and Monitor Dry Eye Disease: Report of the Diagnostic Methodology Subcommittee of the International Dry Eye Workshop (2007)", The Ocular Surface, Apr. 2007, 5(2): 108-152.
Brunton et al., "Chemotherapy of Neoplastic Diseases," Goodman & Gillman's. The Pharmacological Basis of Therapeutics, 11th edition, 2008, 853-908.
Brunning et al., "Myelodysplastic syndromes/neoplasms, overview," WHO Classification of Tumours of Haematopoietic and Lymphoid Tissues, 4th edition, 2008, 88-103.
Burger et al., "Gp130 and ras mediated signaling in human plasma cell line IN/a-6: a cytokine-regulated tumor model for plasmacytoma", Hematol J., 2001, 2:42-53.
Burger et al., "Janus kinase inhibitor INCB20 has antiproliferative and apoptotic effects on human myeloma cells in vitro and in vivo", Mol. Cancer Ther., Jan. 2009, 8(1): 26-35.
Campas-Moya, "Ruxolitinib. Tyrosine-protein kinase JAK1/2 inhibitor, treatment of myelofibrosis, treatment of myeloproliferative neoplasms, treatment of psoriasis", Drugs of the Future, Jun. 2010, 35(6):457-465.

(56) References Cited

OTHER PUBLICATIONS

Candotti et al., "Structural and functional basis for JAK3-deficient severe combined immunodeficiency.", Blood, 1997, 90(10): 3996-4003.
Candotti et al., "Molecular aspects of primary immuno-deficiencies: lessons from cytokine and other signaling pathways.", J Clin Invest, May 2002, 109(10): 1261-9.
Carey and Sundberg, Advanced Organic Chemistry, Part B: Reactions and Synthesis, 4th ed., Kluwer Academic/Plenum Publishers:New York, 2001, 111-119.
Carey and Sundberg, Advanced Organic Chemistry, Part B: Reactions and Synthesis, Oxidations, 4th ed., Kluwer Academic/Plenum Publishers:New York, 2001, 747-757.
Cermak et al, "Is complete androgen insensitivity syndrome associated with alterations in the meibomian gland and ocular surface," Cornea, 2003, 22:516-521.
Cetkovic-Cvrlje et al., "Targeting JAK3 with JANEX-1 for prevention of autoimmune type 1 diabetes in NOD mice.", Clin Immunol, 2003, 106(3): 213-25.
Chalandon, "Targeting mutated protein tyrosine kinases and their signaling pathways in hematologic malignancies," Haematologica, 2005, 90(7):949-68.
Changelian et al., "Prevention of Organ Allograft Rejection by a Specific Janus Kinase 3 Inhibitor", Science, 2003, 302: 875-878.
Chari et al., "Complete Remission Achieved with Single Agent CNTO 328, an Anti-IL-6 Monoclonal Antibody, in Relapsed and Refractory Myeloma," *Clinical Lymphoma, Myeloma & Leukemia*, 2013, 13(3):333-337.
Chauhan et al, "Autoimmunity in Dry Eye due to resistance of Th17 to Treg Suppression", J. Immunology, 2009, 182(3):1247-52.
Chauhan et al., "A concise review on sustained drug delivery system and its opportunities," International Journal on Pharmtech Research, Mar. 2012, 2: 227-238.
Chemical encyclopedia publication "Soviet Encyclopedia," Moscow, 1988, 1:242-243.
Chen et al., "Blockade of interleukin-6 signaling augments regulatory T-cell reconstitution and attenuates the severity of graft-versus-host disease," Blood, Jul. 2009, 114(4): 891-900.
Chen et al., "Stat3 Activation in Human Endometrial and Cervical Cancer", British Journal of Cancer, 2007, 96: 591-599.
Chen et al., "Induction of myelodysplasia by myeloid-derived suppressor cells," J Clin Invest, Nov. 2013, 123(11):4595-611.
Cheson et al., "Report of an international working group to standardize response criteria for myelodysplastic syndromes," Blood, Dec. 2000, 96(12): 3671-4.
Chew et al., "An instrument for quantifying meibomian lipid on the lid margin: the Meibometer", Curr Eye Res, 1993, 12:247-254.
Chew et al., "The casual level of meibomian lipids in humans", Current Eye Research, 1993, 12:255-259.
Chinese Office Action in Chinese Application No. 201480024761.9, dated Oct. 8, 2016, 21 pages (English Translation).
Chinese Notice of Reexamination in Chinese Application No. 201080033675.6, dated May 10, 2016, 18 pages (English Translation).
Cho et al, "Review of the tear break-up time and a closer look at the tear break-up time of Hong Kong Chinese", Optom Vis Sci, 1993, 70(1):30-8.
Choi Ha-Soon et al., "Design and synthesis of 7H-pyrrolo[2,3-d]pyrimidines as focal adhesion kinase inhibitors. Part 1", Bioorg. & Med. Chem. Lett., 2006, 16(8):2173-2176.
Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002, 46(12) 3143-3150.
Chu-Moyer et al., "Preparation of the Four Regioisomeric 2-(Methylthio)oxazolopyridines: Useful Synthons for Elaboration to 2-(Amino substituted)oxazolopyridines", J. Org. Chem., 1995, 60(17): 5721-5725.
Cilloni et al., "Emerging drugs for chronic myeloid leukemia", Expert Opinion on Emerging Drugs, Jun. 2010, 15(2): 175-184.

Claessens et al., "In vitro proliferation and differentitation of erythyroid progenitors from patients with myelodysplastic syndromes: evidence for Fas-dependent apoptosis," Blood, Mar. 2002, 1594-1601.
Claridge et al., "Discovery of a novel and potent series of thieno[3,2-b]pyridine-based inhibitors of c-Met and VEGFR2 tyrosine kinases," Bioorganic & Medicinal Chemistry Letters, 2008, 2793-2798.
Clark et al., "Discovery and Development of Janus Kinase (JAK) inhibitors for Inflammatory Diseases," J Med Chem., 2014, A-P.
Clinical Trial NCT01787487 ('487 Trial), dated Feb. 7, 2013, 6 pages.
ClinicalTrials.gov, <http:clinicaltrials.gov/ct2/show/NCT00227591>, downloaded Dec. 6, 2016.
Coligan et al, Wiley Press; Methods in Molecular Biology: vol. 225, Inflammation Protocols., Winyard, P.G. and Willoughby, D.A., Humana Press (2003) **Too Voluminous to Provide.
Columbian Office Action in Columbian Application No. 12-213.010, dated Jun. 17, 2014, 20 pages.
Communication dated Jan. 22, 2009 for European Appln. No. 06839328.9 (5 pgs.).
Conklyn et al., "The JAK3 inhibitor CP-0690550 selectively reduces NK and CD8+ cell numbers in cynomolgus monkey blood following chronic oral dosing," Journal of Leukocyte Biology, Dec. 2004, 76: 1248-1255.
Costa Rican Office Action in CR Application No. 10065, dated Jul. 16, 2013, 8 pages.
Cottet and Schlosser, "Three Chloro(trifluoromethyl)pyridines as Model Substrates for Regioexhaustive Functionalization," Eur J Org Chem, 2004, 18:3793-3798.
Craig et al. "Tear lipid layer structure and stability following expression of the meibomian glands.", Ophthalmic Physiol Opt, 1995, 15(6):569-74.
Current Protocols in Immunology, vol. 3., Coligan, J.E. et al, Wiley Press (1988) **Too Voluminous to Provide.
Daniels et al., "Imatinib mesylate inhibits the profibrogenic activity of TGF-? and prevents bleomycinmediated lung fibrosis," J. Clin. Invest., Nov. 2004, 114(9):1308-1316.
Danjo et al., "Observation of precorneal tear film in patients with Sjogren's syndrome", Acta Ophthalmol Scand, 1995, 73:501-505.
De Paiva et al, "IL-17 disrupts corneal barrier following desiccating stress," Mucosal Immunol., 2009, 2(3):243-53.
De Vos et al., "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 2000, 109(4): 823-8.
Deng Jun et al, "Rh-catalyzed asymmetric hydrogenation of gamma-phthalimido-substituted esters: an efficient enantioselective synthesis of beta-aryl-gamma-amino acids", Org. Lett., 2007, 9(23):4825-4827.
Deuse et al., "Novel Immunosuppression: R348, a JAK3- and Syk-Inhibitor Attenuates Acute Cardiac Allograft Rejection," Transplantation, 2008, 85(6): 885-892.
Divkovic et al., "Hapten-protein binding: from theory to practical application in the in vitro prediction of skin sensitization," Contact Dermatitis, 2005, 189-200.
Doane, "An instrument for in vivo tear film interferometry", Optom Vis Sci, 1989, 66: 383-8.
Doleschall et al., "Thermal and Acid Catalysed Degradations of 3-alkylthio-6,7-dihydro[1.2.4]triazino[1,6-c]quinazolin-5-ium-1-olates," Tetrahedron, 1974, 30:3997-4012.
Dorwald, "Side Reactions in Organic Synthesis: A Guide to Successful Synthesis Design," Wiley-VCH, 2005, Chapter 1, 32 pages.
Dudley et al. "A VEGF/JAK2/STAT5 axis may partially mediate endothelial cell tolerance to hypoxia", Biochem. J., 2005, 390(Pt 2):427-36.
Eghtedar et al., "Phase 2 study of the JAK kinase inhibitor ruxolitinib in patients with refractory leukemias, including postmyeloproliferative neoplasm acute myeloid leukemia," Blood, May 2012, 119(20): 4614-4618.

(56) References Cited

OTHER PUBLICATIONS

Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract/poster 509.
Einmahl et al., "Therapeutic applications of viscous and injectable poly(ortho esters)," Adv. Drug. Deliv. Rev., 2001, 53:45-73.
Eliason et al., "Staining of the conjunctiva and conjunctival tear film," Br J Ophthalmol, 1990, 74:519-22.
Elliott et al., "WHO-defined chronic neutrophilic leukemia: a long-term analysis of 12 cases and a critical review of the literature," Leukemia, 2005, 19:313-317.
Expert Scientific Group on Phase One Clinical Trials Final Report, Nov. 30, 2006, pp. C1, C35-C38.
Saettone and Salminen, "Ocular inserts for topical delivery", Advanced Drug Delivery Reviews, 1995, 16:95-106.
Farrell et al., "A classification for dry eyes following comparison of tear thinning time with Schirmer tear test," Acta Ophthalmol (Copenh), 1992, 70(3):357-60.
Farrell et al., "A clinical procedure to predict the value of temporary occlusion therapy in keratoconjunctivitis sicca," Ophthal Physiol Opt, 2003, 23:1-8.
Farris, "Tear osmolarity—a new gold standard?" Adv Exp Med Biol, 1994, 350:495-503.
Fayad et al., "Interleukin-6 and interleukin-10 levels in chronic lymphocytic leukemia: correlation with phenotypic characteristics and outcome," Blood, Jan. 2001, 97(1): 256-263.
Fenaux et al., "A randomized phase 3 study of lenalidomide versus placebo in RBC transfusion-dependent patients with Low-/Intermediate-1-risk myelodysplastic syndromes with del5q," Blood, Oct. 2011, 118(14): 3765-76.
Fenaux et al., "Efficacy of azacitidine compared with that of conventional care regimens in the treatment of higher-risk myelodysplastic syndromes: a randomised, open-label, phase III study," Lancet Oncol, Mar. 2009, 10: 223-32.
Fiskus et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov. 1, 2010 p. 349, XP002667216, ISSN: 0002-7863 (1 page).
Fleischman et al., "The CSF3R T618I mutation causes a lethal neutrophilic neoplasia in mice that is responsive to therapeutic JAK inhibition," Blood, Nov. 2013, 122: 3628-3632.
Flex et al., "Somatically acquired JAK1 mutations in adult acute lymphoblastic leukemia", J. Exp Med., 2008, 205:751-8.
Fonseca et al., "Interleukin-6 as a key player in systemic inflammation and joint destruction", Autoimmunity Reviews, 2009, 8:538-42.
Forbes et al., "Synthesis and evaluation of a series of aryl [e] fused pyrazolo [4,3-c]pyridines with potential anxiolytic activity," J Medicinal Chem., Jan. 1, 1990, 33(9):2640-2645.
Foucar (Am J Olin Pathol 2009;132:281-289).
Fridman et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).
Fridman et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman et al., "Preclinical evaluation of local JAK1 and JAK2 inhibition in cutaneous inflammation", Journal of Investigative Dermatology, Sep. 2011, 131(9): 1838-1844.
Fridman et al., "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285 (1 page).
Fridman et al., "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman et al., "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009 (1 page).
Froberg et al., "Demonstration of clonality in neutrophils using FISH in a case of chronic neutrophilic leukemia," Leukemia, 1998, 12:623-626.
Fujihara et al., "Evaluation of human conjunctival epithelium by a combination of brush cytology and flow cytometry: an approach to the quantitative technique", Diagn Cytopathol, 1997, 17:456-60.
Fujii et al., "Aberrant expression of serine/threonine kinase Pim-3 in hepatocellular carcinoma development and its role in the proliferation of human hepatoma cell lines" International Journal of Cancer, 2005, 114: 209-218.
Fukagawa et al., "Histological evaluation of brush cytology of rabbit conjunctiva", Nippon Ganka Gakkai Zasshi, 1993, 97:1173-8 (contains English abstract within the article).
Gaertner, "Cyclization of 1-Alkylamino-3-halo-2-alkanols to 1-Alkyl-3-azetidinols," J. Org. Chem., 1967, 32: 2972-76.
Gaestel et al., "Targeting innate immunity protein kinase signalling in inflammation," Nat Rev Drug Discov., Jun. 2009, 8(6):480-99.
Ghelardi et al., "A Mucoadhesive Polymer Extracted from Tamarind Seed Improves the Intraocular Penetration and Efficacy of Rufloxacin in Topical Treatment of Experimental Bacterial Keratitis", Antimicrob. Agents Chemother., 2004, 48:3396-3401.
Gilchrist et al., "5H-2-Pyridines from 2-Bromocyclopentene-1-carboxaldehyde," Tetrahedron, Jan. 1, 1995, 9119-9126.
Glasson et al., "Differences in clinical parameters and tear film of tolerant and intolerant contact lens wearers," Invest Ophthalmol Vis Sci, 2003, 44:5116-5124.
Glattfeld, "Improvements in the Preparation of DL-Threonic and DL-Erythronic Acids", J. Am. Chem. Soc., 1940, 62:974-977.
Gobbels et al., "Tear secretion in dry eyes as assessed by objective fluorophotometry.," Ger J Ophthalmol, 1992, 1:350-353.
Golding et al., "X-ray and scanning electron microscopic analysis of the structural composition of tear ferns", Cornea, Jan. 1994, 13(1):58-66.
Gomtsyan et al, "Design, synthesis, and structure-activity relationship of 6-alkynylpyrimidines as potent adenosine kinase inhibitors," J. Med. Chem., 2002, 45(17):3639-3648.
Goodman et al., "IL-6 Signaling in Psoriasis Prevents Immune Suppression by Regulatory T Cells," J. Immunol., Sep. 2009, 183: 3170-3176.
Gooseman et al., "The intramolecular b-fluorine . . . ammonium interaction in 4- and 8-membered rings", Chem. Commun, 2006, 30:3190-3192.
Gorre et al., "Clinical Resistance to STI-571 Cancer Therapy Caused by BCR-ABL Gene Mutation or Amplification." Science, 2001, 293:876-880.
Gotlieb, Alice, Presentation at the 2008 American Academy of Dermatology, 66th Annual Meeting, San Antonio, TX. Feb. 1, 2008, symposium-303 (12 pp.).
Goto et al., "Color mapping of tear lipid layer thickness distribution from the image analysis in DR-1 tear lipid layer interference images," ARVO abstract, 2004, 2 pages.
Goto et al., "Computer-synthesis of an interference color chart of human tear lipid layer by a colorimetric approach," Invest Ophthalmol Vis Sci, 2003, 44:4693-7.
Goto et al., "Differentiation of lipid tear deficiency dry eye by kinetic analysis of tear interference images,",Arch Ophthalmol, 2003, 121:173-80.
Goto et al., "Evaluation of the tear film stability after laser in situ keratomileusis using the tear film stability analysis system," Am J Ophthalmol, Jan. 2004, 137(1):116-20.

(56) References Cited

OTHER PUBLICATIONS

Goto et al., "Tear Film Stability Analysis System: Introducing a new application for videokeratography", Cornea, Nov. 2004, 23(8):S65-S70.
Goto et al., "Kinetic analysis of tear interference images in aqueous tear deficiency dry eye before and after punctal occlusion," Invest Ophthalmol Vis Sci, 2003, 44:1897-905.
Gottlieb, "Psoriasis: Emerging Therapeutic Strategies," Nat Rev Drug Disc., Jan. 2005, 4:19-34.
Grabbe et al., "Immunoregulatory mechanisms involved in elicitation of allergic-contact hypersensitivity," Immunol Today, Jan. 1998, 19(1):37-44 (only 1 page provide and marked "best available copy").
Green and Wuts, P.G.M.. Protective Groups in Organic Synthesis, 3rd. Ed., Wiley & Sons, Inc., New York (1999) **Too Voluminous to Provide.
Wuts and Greene, Protective Groups in Organic Synthesis, 4th ed., John Wiley & Sons: New Jersey, (2007) ** Too Voluminous to Provide.
Greenberg, "The Role of Hemopoietic Growth Factors in the Treatment of Myelodysplastic Syndromes," International Journal of Pediatric Hematology/Oncology, 1997, 4(3): 231-238.
Greenberg, "The myelodysplastic syndromes" in Hoffman, et al, eds. Hematology: Basic Principles and Practice (3rd ed.), Churchill Livingston; 2000:1106-1129.
Greene et al., Greene's Protective Groups in Organic Synthesis, 2007, 4th Edition, 54-55.
Gregory et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, 2003, 58, 1101-1113.
Grossman, et al., "Interleukin 6 is expressed in high levels in psoriatic skin and stimulates proliferation of cultured human keratinocytes," Proc. Natl. Acad., Sci. USA, Aug. 1989, 86: 6367-6371.
Guillon, "Tear film photography and contact lens wear", J Br Contact Lens Assoc, 1982;5:84-7.
Gura, "Systems for Identifying New Drugs Are Often Faulty," Science, Nov. 1997, 278(5340): 1041-1042.
Guschin et al, "A major role for the protein tyrosine kinase JAK1 in the JAK/STAT signal transduction pathway in response to interleukin-6", Embo 3 14:1421-1429 (1995).
Hamze' et al., "Synthesis of Various 3-Substituted 1,2,4-Oxadiazole-Containing Chiral β3-and r-Amino Acids from Fmoc-Protected Asparlic Acid," J. Org. Chem., 2003, 68(19), pp. 7316-7321.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Harris et al., "World Health Organization classification of neoplastic diseases of the hematopoietic and lymphoid tissues: report of the Clinical Advisory Committee meeting-Airlie House, Virginia, Nov. 1997," J Clin Oncol, 1999, 17:3835-3849.
Harris et al., "Alkyl 4-Chlorobenzoyloxycarbamates as Highly Effective Nitrogen Source Reagents for the Base-Free, Intermolecular Aminohydroxylation Reaction," J. Org. Chem., 2011, 76:358-372.
Heine et al., "The JAK-inhibitor ruxolitinib impairs dendritic cell function in vitro and in vivo," Blood, 2013, 122(7): 1192-1202.
Helal et al., "Stereoselective Synthesis of cis-1,3-Disubstituted Cyclobutyl Kinase Inhibitors," Organic Letters, (2004), 6(11), pp. 1853-1856.
Hernandez et al., "Clinical, hematological and cytogenetic characteristics of atypical chronic myeloid leukemia," Ann. Oncol., Apr. 2000, 11(4): 441-444.
Hickenbottom "Reactions of organic compounds," State Scientific-Technical Publishing Association, Chemical Literature Section, Moscow, 1939, pp. 360-362.
Higuchi et al., "Pro-drugs as Novel Delivery Systems," vol. 14 of the A.C.S. Symposium Series (1975)* too voluminous to provide.
Holly et al., "Lacrimation kinetics in Humans as determined by a novel technique", in Holly FJ (ed). The preocular tear film. Lubbock TX, Lubbock Dry Eye Institute, 1986, pp. 76-88).
Hong, et al., "Total Synthesis of Onnamide A", J. Am. Chem. Soc., 113:9693-94 (1991).
Huang, "Inhibition of STAT3 activity with AG490 decreases the invasion of human pancreatic cancer cells in vitro", Cancer Sci. 97(12):1417-23 (2006).
Huttel, et al., "Lithium pyrazole compounds", Liebigs Ann. Chem. Bd., 625:55-65 (1959) (abstract provided).
Hyung-Bae et al., "CP-690550, a Janus Kinase Inhibitor, Suppresses CD4+ T-Cell-Mediated Acute Graft-Versus-Host Disease by Inhibiting the Interferon-Y Pathway," *Transplantation*, 2010, 90(8):825-835.
International Preliminary Report on Patentability (with Written Opinion) dated Jun. 18, 2008 for International Appln. No. PCT/US2006/047369 (10 pgs.).
International Preliminary Report on Patentability (with Written Opinion) dated Mar. 6, 2012 for International Appln. No. PCT/US2010/047252 (7 pgs.).
International Preliminary Report on Patentability (with Written Opinion) dated Nov. 22, 2011 for International Appln. No. PCT/US2010/035728 (8 pgs.).
International Preliminary Report on Patentability (with Written Opinion) dated Nov. 22, 2011 for International Appln. No. PCT/US2010/035783 (5 pgs.).
International Preliminary Report on Patentability for International Appln. No. PCT/US2008/066662 dated Dec. 17, 2009 (7 pgs.).
International Preliminary Report on Patentability for PCT/US2008/66658 dated Dec. 17, 2009 (7 pages).
International Preliminary Report on Patentability for PCT/US2009/036635 dated Sep. 14, 2010 (6 pages).
International Preliminary Report on Patentability for PCT/US2009/059203 dated Apr. 5, 2011 (6 pages).
International Preliminary Report on Patentability for PCT/US2010/021003 dated Jul. 19, 2011(11 pages).
International Preliminary Report on Patentability for PCT/US2010/052011 dated Apr. 11, 2012 (4 pages).
International Preliminary Report on Patentability for PCT/US2011/025433 dated Aug. 21, 2012 (7 pages).
International Preliminary Report on Patentability for PCT/US2011/027665 dated Sep. 11, 2012 (7 pages).
International Preliminary Report on Patentability for PCT/US2011/037291 dated Nov. 27, 2012 (7 pages).
International Preliminary Report on Patentability for PCT/US2011/061351 dated May 30, 2013 (7 pages).
International Preliminary Report on Patentability for PCT/US2011/061374 dated May 30, 2013 (5 pages).
International Preliminary Report on Patentability for PCT/US2012/043099 dated Dec. 23, 2013, 6 pages.
International Preliminary Report on Patentability for PCT/US2012/050210 dated Feb. 11, 2014, 8 pages.
International Preliminary Report on Patentability for PCT/US2012/051439 dated Feb. 27, 2014, 7 pages.
International Preliminary Report on Patentability for PCT/US2012/053921 dated Mar. 20, 2014, 8 pages.
International Preliminary Report on Patentability for PCT/US2013/041601, dated Nov. 18, 2014, 7 pages.
International Preliminary Report on Patentability in International Application No. PCT/US2014/051678, dated Mar. 3, 2016, 15 pages.
International Preliminary Report on Patentability in International Application No. PCT/US2015/028224, dated Nov. 10, 2016, 7 pages.
International Preliminary Report on Patentability in International Application No. PCT/US2014/049940, dated Feb. 18, 2016, 9 pages.

(56) References Cited

OTHER PUBLICATIONS

International Search Report and the Written Opinion, PCT/US2012/051439, dated Nov. 30, 2012 (15 pages).
International Search Report and the Written Opinion, PCT/US2012/053921, dated Nov. 7, 2012 (19 pages).
International Search Report and Written Opinion dated Feb. 9, 2010 for International Appln. No. PCT/US2009/059203 (10 pages).
International Search Report and Written Opinion for International Appln. No. PCT/US2005/046207 dated May 15, 2007 (6 pages).
International Search Report and Written Opinion for International Appln. No. PCT/US2008/066662 dated Dec. 23, 2008 (11 pgs.).
International Search Report and Written Opinion for International Appln. No. PCT/US2009/036635 dated Jun. 3, 2009 14 pages.
International Search Report and Written Opinion for PCT/US2006/047369, 16 pages (dated Apr. 24, 2007).
International Search Report and Written Opinion for PCT/US2008/083319, 29 pages dated Mar. 13, 2009.
International Search Report and Written Opinion for PCT/US2011/025433, 12 pages (dated Jul. 20, 2011).
International Search Report and Written Opinion for PCT/US2011/027665 dated Jun. 27, 2011 (14 pages).
International Search Report and Written Opinion for PCT/US2011/037291, 11 pages (dated Apr. 19, 2012).
International Search Report and Written Opinion for PCT/US2011/061351 dated Feb. 17, 2012 (12 pages).
International Search Report and Written Opinion for PCT/US2011/061374 dated Mar. 27, 2012 (10 pages).
International Search Report and Written Opinion for PCT/US2012/025581, 16 pages (dated Apr. 26 2012).
International Search Report and Written Opinion for PCT/US2012/043099, 11 pages (dated Sep. 13, 2012).
International Search Report and Written Opinion for PCT/US2012/050252 dated Jan. 2, 2013, 17 pages.
International Search Report and Written Opinion in International Application No. PCT/US2013/067794, dated Dec. 17, 2013, 14 pages.
International Search Report and Written Opinion in International Application No. PCT/US2014/020554, dated Jul. 16, 2014, 17 pages.
International Search Report and Written Opinion in International Application No. PCT/US2014/049940, dated Nov. 4, 2014, 13 pages.
International Search Report and Written Opinion in International Application No. PCT/US2014/051678, dated Feb. 11, 2015, 22 pages.
International Search Report and Written Opinion in International Application No. PCT/US2015/017963, dated Jun. 5, 2015, 13 pages.
International Search Report and Written Opinion in International Application No. PCT/US2015/033254, dated Oct. 7, 2015, 12 pages.
International Search Report for PCT/US2008/66658 dated Dec. 23, 2008 (4 pages).
International Search Report for PCT/US2010/021003 dated Aug. 16, 2010 (8 pages).
International Search Report for PCT/US2010/035728 dated Jul. 8, 2010 (3 pages).
International Search Report for PCT/US2010/035783 dated Aug. 23, 2010 (4 pages).
International Search Report for PCT/US2010/047252 dated Nov. 17, 2010 (4 pages).
International Search Report for PCT/US2010/052011 dated Nov. 30, 2010 (3 pages).
International Search Report in International Application No. PCT/US2013/041601, dated Sep. 3, 2013, 3 pages.
International Search Report and Written Opinion in International Application No. PCT/US2015/028224, dated Jul. 15, 2015, 9 pages.

Iranpoor, "A Rapid and Facile Conversion of Primary Amides and Aldoximes to Nitriles and Ketoximes to Amides with Triphenylphosphine and N-Chlorosuccinimide," G Syn., 2002, Commun 32:2535-41.
Ishizaki et al., "Pharmacological Properties of Y-27632, a Specific Inhibitor of Rho-Associated Kinases", Molecular Pharmacology, 2000, 57, 976-983.
Itagaki et al, "Expedient Synthesis of Potent Cannabinoid Receptor Agonist (-)-CP55,940", Organic Letters, 2005, 7(19): 4181-4183.
Jädersten et al., "Long-term outcome of treatment of anemia in MDS with erythropoietin and G-CSF," Blood, Aug. 2005, 106(3): 803-11.
James et al., "A unique clonal JAK2 mutation leading to constitutive signalling causes polycythaemia vera", Nature, 434 (7037):1144-8 (2005).
Janes et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.
Japanese Office Action in Japanese Application No. 2015-219637, dated Oct. 4, 2016, 6 pages.
Japanese Office Action in Japanese Application No. 2013-540049, dated Aug. 11, 2015, 3 pages (English Translation).
Japanese Office Action in Japanese Application No. 2015-042933, dated Feb. 2, 2016, 6 pages (English Translation).
Japanese Office Action in Japanese Application No. 2015-241393, dated Sep. 27, 2016, 4 pages (English Translation).
Japanese Office Action in Japanese Application No. 2017-000685, dated Jan. 31, 2017, 7 pages (with English translation).
Jee et al., "Overview: animal models of osteopenia and osteoporosis", J Musculoskel. Neuron, Interact., 1(3):193-207 (2001).
Jester et al., "In vivo biomicroscopy and photography of meibomian glands in a rabbit model of meibomian gland dysfunction", Invest Ophthalmol Vis Sci, 1982;22:660-7.
Johnson et al., "The effect of instilled fluorescein solution volume on the values and repeatability of TBUT measurements", Cornea, 2005;24:811-7.
Kaddis et al., "Second-Line Treatment for Pancreatic Cancer," Journal of the Pancreas, Jul. 2014, XP055147286, Retrieved from the Internet: URL: http://www.serena.unina.it/index.php/jop/article/viewFile/2691/2737 [retrieved on Oct. 17, 2014].
Kaercher, "Ocular symptoms and signs in patients with ectodermal dysplasia syddromes", Graefe's Arch Clin Exp Ophthalmol, 2004;495-500.
Kamb, "What's wrong with our cancer models?," Nature Reviews, Feb. 2005, 161-165.
Kantarjian et al., "Decitabine improves patient outcomes in myelodysplastic syndromes: results of phase III randomized study," Cancer, Apr. 2006, 106(8): 1794-803.
Kaushansky, "Lineage-Specific Hematopoietic Growth Factors," NEJM, 2006, 354:2034-45.
Kawamura et al., "Molecular cloning of L-JAK, a Janus family protein-tyrosine kinase expressed in natural killer cells and activated leukocytes," Proc Natl Acad Sci USA, 1994, 91(14): 6374-8.
Kharas et al., "ABL Oncogenes and Phosphoinositide 3-Kinase: Mechanism of Activation and Downstream Effectors," Cancer Res., Mar. 2005, 65(6):2047-2053.
Killedar et al., "Early pathogenic events associated with Sjogren's syndrome (SjS)-like disease of the NOD mouse using microarray analysis," Lab Invest, Dec. 2006, 86(12): 1243-1260.
Kim et al., "Zinc-Modified Cyanoborohydride as a Selective Reducing Agent," J. Org. Chem., 1985, 50: 1927-1932.
Kuster, "Kinase Inhibitors," Methods and Protocols, 2012, 46 pages.
King-Smith et al., "Three interferometric methods for measuring the thickness of layers of the tear film," Optom Vis Sci, 1999, 76:19-32.
Kiss, "Recent developments on JAK2 inhibitors: A patent review", Expert Opinion on Therapeutic Patents, Apr. 2010, 20(4):471-495.
Kojima et al., "A new noninvasive tear stability analysis system for the assessment of dry eyes", Invest Ophthalmol Vis Sci, 2004, 45(5):1369-74.
Kola, "Can the pharmaceutical industry reduce attrition rates?" Nature Reviews Drug Discovery, 2004, 3:711-715.

(56) References Cited

OTHER PUBLICATIONS

Komuro et al., "Assessment of meibomian gland function by a newly developed laser meibometer", Adv Exp Med Biol, 2002, 506:517-520.
Korb et al., "The effect of two novel lubricant eye drops on tear film lipid layer thickness in subjects with dry eye symptoms", Optom Vis Sci, 2005, 82: 594-601.
Korb et al., "Increase in tear film lipid layer thickness following treatment of meibomian gland dysfunction", Adv Exp Med Biol, 1994, 350:293-8.
Korolev et al., "Pd-EDTA as an efficient catalyst for Suzuk-Miyaura reactions in water", Tet. Lett., 2005, 46: 5751-5754.
Kortylewski et al., "Regulation of the IL-23 and IL-12 balance by Stat3 signaling in the tumor microenvironment", Cancer Cell, 2009, 15:114-123.
Kontzias et al., "Jakinibs: a new class of kinase inhibitors in cancer and autoimmune disease," Curr. Opin. Pharm., 2012, 12: 464-470.
Kruh et al., "The complete coding sequence of arg defines the Abelson subfamily of cytoplasmic tyrosine kinases.", Proc. Natl. Acad. Sci., Aug. 1990, 87:5802-5806.
Kubinyi, "QSAR: Hansch Analysis and Related Approaches," Methods and Principles in Medicinal Chemistry, Manhold, R. ed. Weinheim, NY, 1993, 42 pages.
Kudelacz et al. "The JAK-3 inhibitor CP-690550 is a potent anti-inflammatory agent in a murine model of pulmonary eosinophilia", European Journal of Pharmacology, 2008, 582: 154-161.
Kumar, "Kinase drug discovery approaches in chronic myeloproliferative disorders", Oncogene, Jun. 2009, 28(24): 2305-23.
Kuo et al., "Pd-EDTA as an efficient catalyst for Suzuki-Miyaura reactions in water", Chem Commun, 2007, 301-3.
Kuppens et al., "Basal tear turnover and topical timolol in glaucoma patients and healthy controls by Fluorophotometry", Invest Ophthalmol Vis Sci, 1992, 33:3442-3448.
Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118-2122.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Lai et al., "Mechanistic Study on the Inactivation of General Acyl-CoA Dehydrogenase by a Metabolite of Hypoglycin A," J. Am. Chem. Soc., 1991, 113: 7388-7397.
Lam et al, "Tear Cytokine Profiles in Dysfunctional Tear Syndrome", Am J Ophthalmol., 2009, 147(2):198-205.
Larock, "Comprehensive Organic Transformations", Wiley-VCH, 2nd Ed. (1999) pp. 1949-1950, 1958-1959, 1976, and 1983-1985.
Larson, "Myelodysplasia: when to treat and how," Best Pract Res Clin Haematol, 2006, 19(2): 293-300.
Lasho et al., "Chronic neutrophilic leukemia with concurrent CSF3R and SETBP1 mutations: single colony clonality studies, in vitro sensitivity to JAK inhibitors and lack of treatment response to ruxolitnib," Leukemia, 2014, 3 pages.
Lawrence "Skin inflammatory disorders," In In Vivo Models of Inflammation, 2006, 85-120.
Leaf, Clifton, Health Administrator vol. XVII, 2005, 1:172-183.
Lemp "Report of National Eye Institute/Industry Workshop on clinical trials in dry eyes," CLAO J, 1995, 21:221-232.
Lemp et al., "Corneal desiccation despite normal tear volume", Ann Ophthalmol, 1970 (2) pages:258-261 & 284.
Lemp et al., "The Definition and Classification of Dry Eye Disease: Report of the Definition and Classification Subcommittee of the International Dry Eye WorkShop", The Ocular Surface, 5(2), 75-92 Apr. 2007.
Letter translation of Office Action, Chilean Application No. 3496-2006 as received from the foreign associate (dated Jul. 5, 2010) (4 pages).
Levine et al., "Activating mutation in the tyrosine kinase JAK2 in polycythemia vera, essential thrombocythemia, and myeloid metaplasia with myelofibrosis", Cancer Cell, 2005, 7:387-397.
Levitzki, "Tyrosine kinases as targets for cancer therapy", Eur. J. Cancer, 2002, 38(suppl. 5):S11-S18.
Levy et al. "INCB018424 A Selective Janus Kinase 1/2 Inhibitor Presentation at the 50th American Society of Hematology Annual Meeting (ASH)," Dec. 8, 2008, 27 pages.
Li et al., "The synthesis and the antitumor activity of 5,7-disubstituted pyrazolo [1,5-a] pyrimidines," Chinese J Med Chem., Feb. 28, 2007, 17(1):18-22.
Li et al., "Pim-3, a proto-oncogene with serine/threonine kinase activity, is aberrantly expressed in human pancreatic cancer and phosphorylates Bad-mediated apoptosis in human pancreatic cell lines," Cancer Research, 2006, 66(13): 6741-7.
Liesveld and Lichtman, Chapter 88. "Myelodysplastic Syndromes (Clonal Cytopenias and Oligoblastic Myelogenous Leukemia)", in Prchal et al, eds. Williams Hematology. 8th ed., New York: McGraw-Hill; 2010.
Lima and Barreiro, "Bioisosterism: a useful strategy for molecular modification and drug design," Curr Med Chem., 2005, 12(1):23-49.
Lin, "Constitutive Activation of JAK3/STAT3 in Colon Carcinoma Tumors and Cell Lines," Am J Pathol., 2005, 167(4):969-80.
Lin et al., "Enantioselective synthesis of Janus kinase inhibitor INCB018424 via an organocatalytic aza-Michael reaction," Organic Letters, 2009, 11(9): 1999-2002.
Ling et al., "Knockdown of STAT3 Expression by RNA Interference Inhibits the Induction of Breast Tumors in Immunocompetent Mice," Cancer Res, Apr. 2005 65:2532.
List et al., "Efficacy of lenalidomide in myelodysplastic syndromes," N Engl J Med, Feb. 2005, 352(6): 549-57.
Liu et al., "Combined Inhibition of Janus Kinase 1/2 for the Treatment of JAK2V617F-Driven Neoplasms: Selective Effects on Mutant Cells and Improvements in Measures of Disease Severity," Clin Cancer Res, 2009, 15(22):6891-6900.
Lübbert et al., "Cytogenic responses in high-risk myelodysplastic syndrome following low-dose treatment with the DNA methylation inhibitor 5-aza-2'-deoxycytidine," Br J Haematol, Aug. 2001, 114(2):349-57.
Lübbert et al., "Low-dose decitabine versus best supportive care in elderly patients with intermediate- or high-risk myelodysplastic syndrome (MDS) ineligible for intensive chemotherapy: final results of the randomized phase III study of the European Organisation for Research and Treatment of Cancer Leukemia Group and the German MDS Study Group," J Clin Oncol, May 2011, 29(15): 1987-96.
Lucet et al. "The structural basis of Janus kinas 2 inhibition by a potent and specific pan-Janus . kinase inhibitor," Blood, 2006, 107(1):176-183.
Macchi et al., "Mutations of Jak-3 gene in patients with autosomal severe combined immune deficiency (SCID)", Nature, 1995, 377:65-8.
Madden et al., "Comparative study of two non-invasive tear film stability techniques," Curr Eye Res, 1994, 13(4):263-9.
Madhusudan et al., "Tyrosine kinase inhibitors in cancer therapy," Clin Biochem., 2004, 37(7):618-35.
Maffioli et al., "Mild and Reversible Dehydration of Primary Amides with PdC12 in Aqueous Acetonitrile", Organic Letters, 2005, 7(23): 5237-39.
Main et al, "High throughput synthesis of diverse 2,5-disubstituted indoles using titanium carbenoids bearing boronate functionality", Tetrahedron, 2007, 64(5):901-914.
Mainstone et al., "Tear meniscus measurement in the diagnosis of dry eye", Curr Eye Res, 1996, 15:653-661.
Malaysian Examination Report in Malaysian Application No. PI2013002970, dated May 31, 2016, 4 pages.
Mancini, M. et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.
Mandal "Cancer Classification," 2014. Available from: <http://www.news-medical.net/health/Cancer-Classification.aspx, 6 pages.

(56) References Cited

OTHER PUBLICATIONS

Manjula et al., "Rapid Method of Converting Primary Amides to Nitriles and Nitriles to Primary Amides by ZnCl2 using Microwaves under Different Reaction Conditions", Syn. Commun, 2007, 37:1545-50.
Manning et al., "The Protein Kinase Complement of the Human Genome," Science, 2002, 298(5600):1912-16 and 1933-34.
Mao et al., "Advances in research of tyrosine kinases inhibitor of vascular endothelial growth factor receptor," Chinese J New Drugs, Dec. 31, 2008, 17(7):544-550.
March, Jerry, Advanced Organic Chemistry: Reactions, Mechanisms, and Structure, 3rd ed., John Wiley & Sons:New York, pp. 845-855 (1985).
Marelli et al., "Tumor targeting via integrin ligands," Frontiers in Oncology, 2013, 1-12.
Marquardt et al., "Modification of tear film break-up time test for increased reliability" in Holly ed. The Preocular Tear Film in Health, Disease and Contact Lens Wear. Lubbock, Texas: Dry Eye Institute, 1986:57-63.
Maruyama et al., "Effect of environmental conditions on tear dynamics in soft contact lens wearers," Invest Ophthalmol Vis Sci, 2004, 45(8):2563-8.
Mascarenhas et al., "Ruxolitinib: The First FDA Approved Therapy for the Treatment of Myelofibrosis," Clinical Cancer Research, Jun. 2012, 18(11): 3008-3014.
Matano et al., "Deletion of the long arm of chormosome 20 in a patient with chronic neutrophilic leukemia: cytogenetic findings in chronic neutrophilic leukemia," Am. J. Hematol., Jan. 1997, 54(1): 72-5.
Mathers et al., "Assessment of the tear film with tandem scanning confocal microscopy", Cornea, 1997;16:162-8.
Mathers et al., "Tear film changes associated with normal aging", Cornea, 1996; 15:229-334.
Mathers et al., "Tear flow and evaporation in patients with and without dry eye", Ophthalmology, 1996, 103:664-669.
Mathers et al., "Video imaging of the meibomian gland", Arch Ophthalmol, 1994, 112:448-9.
Mathers, "Evaporation from the ocular surface", Exp Eye Res, 2004, 78:389-394.
Maxson et al., "Oncogenic CSF3R Mutations in Chronic Neutrophilic Leukemia and Atypical CML," *N. Engl. J. Med.*, 2013, 368(19):1781-1790.
Mayo Clinic. Available at: < http://www.mayoclinic.com/health/pancreatic-cancer/DS00357 >. 2 pages, retrieved from the Internet Apr. 3, 2013.
Mayo Clinic. Available at: < http://www.mayoclinic.com/health/prostate-cancer-prevention/MC00027 >. 3 pages, retrieved from the Internet Apr. 3, 2013.
Mayo Clinic. Available at: <http://www.mayoclinic.com/health/crohns-disease/DS00104/DSECTION=treatments-and-drugs> 6 pages, retrieved from the Internet May 27, 2013.
Mayo Clinic. Available at: <http://www.mayoclinic.com/health/multiple-sclerosis/DS00188/DSECTION=treatments-and-drugs>. 3 pages, retrieved from the Internet May 27, 2013.
Mayo Clinic. Available at: <http://www.mayoclinic.com/health/myasthenia-gravis/DS00375> 2 pages, retrieved from the Internet May 27, 2013.
Mayo Clinic. Available at: <http://www.mayoclinic.com/health/rheumatoid-arthritis/DS00020/DSECTION=treatments-and-drugs> 3 pages, retrieved from the Internet Jun. 26, 2013.
Mayo Clinic. Available at: <http://www.mayoclinic.org/diseases-conditions/type-1-diabetes/basics/prevention> 2014, 9 pages.
McMillan, "The systemic inflammation-based Glasgow Prognostic Score: a decade of experience in patients with cancer," Cancer Treat Rev, Aug. 2013, 39(5): 534-40.
McNamara et al., "Fluorometry in contact lens research: The next step," Optom Vis Sci, 1998, 75:316-322.
MD Anderson Cancer Center. "Leukemia Prevention and Screening," 2014, 2 pages.
MD Anderson Cancer Center. "Myeloproliferative Disease Prevention and Screening," 2014, 2 pages.
Mengher et al., "Non-invasive tear film break-up time: sensitivity and specificity", Acta Ophthalmol (Copenh), 1986, 64(4):441-4.
Mesa et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).
Mesa et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, Nov. 2011, 117(21): 4869-4877.
Mesa et al., "Emerging drugs for the therapy of primary and post essential thrombocythemia, post polycythemia vera myelofibrosis", Expert Opinion on Emerging Drugs England, 2009, 14(3): 471-479.
Methods in Molecular Biology: vol. 225, Inflammation Protocols., Winyard, P.G. and Willoughby, D.A., Humana Press, 2003 **Too Voluminous to Provide.
Meydan et al., "Inhibition of acute lymphoblastic leukaemia by a Jak-2 inhibitor", Nature, Feb. 1996, 379(6566):645-8.
Meyer et al., "Anti-inflammatory activity and neutrophil reductions mediated by the JAK1/JAK3 CP-690,550, in rat adjuvant-induced arthritis," Journal of Inflammation, 2010, 1-12.
Miethchen, "Micelle-activated reactions. I. Micelle-activated iodination and partial dehalogenation of pyrazoles and 1,2,4-triazoles", Journal F. prakt. Chemie, Band 331, Heft 5, S. 799-805 (1989) (1 page abstract also provided).
Milici et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).
Minegishi et al., "Human Tyrosine Kinase 2 Deficiency Reveals Its Requisite Roles in Multiple Cytokine Signals Involved in Innate and Acquired Immunity", Immunity, 2006, 25:745-55.
Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol., Sep. 2010, 85(3):192-9 Epub Jun. 2, 2010.
Mishima et al., "Determination of tear volume and tear flow", Invest Ophthalmol, 1966, 5:264-276.
Mishima, "Some physiological aspects of the precomeal tear film", Arch Ophthalmol, 1965, 73:233-241.
Mitsunobu, "The Use of Diethyl Azodicarboxylate and Triphenylphosphine in Synthesis and Transformation of Natural Products." Synthesis, 1981, (1): 1-28.
Miyata, et al., "Stereospecific nucleophilic addition reactions to olefins.", J. Org. Chem., 1991, 56:6556-6564.
Miyaura et al., "Palladium-Catalyzed Cross-Coupling Reactions of Organoboron Compounds," Chem. Rev., 1995, 95: 2457-2483.
Miyoshi et al., "Interleukin-8 concentrations in conjunctival epithelium brush cytology samples correlate with neutrophil, eosinophil infiltration, and corneal damage", Cornea, 2001, 20:743-7.
Molldrem et al., "Antithymocyte globulin for patients with myelodysplastic syndrome," Br J Haematol, Dec. 1997, 99(3): 699-705.
Moreland et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).
Moriarty et al., "The synthesis and SAR of 2-amino-pyrrolo[2,3-d]pyrimidines: A new class of Aurora-A kinase inhibitors", Bioorganic and Medicinal Chemistry Letters, 2006, 16(22), 5778-5783.
Mosby's Dictionary of Medicine, Nursing, & Health Professions, sicca complex, 2009, Elsevier, printed from http://www.credoreference.com/entry/ehsmosbymed/sicca_complex, 2 pages.
Mullighan et al, "JAK mutations in high-risk childhood acute lymphoblastic leukemia", Proc Natl Acad Sci USA, 2009, 106:9414-8.

(56) References Cited

OTHER PUBLICATIONS

Mundle et al., "Evidence for Involvement of Tumor Necrosis Factor-α in Apoptotic Death of Bone Marrow Cells in Myelodysplastic Syndromes," Am J Hematol, 1999, 60:36-47.
Naka, "The paradigm of IL-6: from basic science to medicine", Arthritis Res., 2002, 4 Suppl 3:S233-42.
Nakagawara, "Trk receptor tyrosine kinases: A bridge between cancer and neural development." Cancer Letters, 2001, 169:107-114.
Nally et al., "Ocular discomfort and tear film break-up time in dry eye patients: A correlation," Invest Ophthalmol Vis Sci, 2000, 41:4:1436 (Poster Presentation).
Naqvi et al., "A potential role of ruxolitinib in leukemia", Expert Opinion on Investigational Drugs, Aug. 2011, 20(8): 1159-1166.
National Cancer Institute, "FDA Approval for Ruxolitinib Phosphate", http://www.cancer.gov/cancertopics/druginfo/fda-ruxolitinibphosphate posted Nov. 18, 2011 (3 pages).
Naus et al., "6-(Het)aryl-7-Deazapurine Ribonucleosides as Novel Potent Cytostatic Agents", J. Med. Chem., 2010, 53(1):460-470.
Neidle Cancer Drug Design and Discovery, (Elsevier/Academic Press, 2008) 427-431.
Nelson et al., "Tear film osmolality determination: an evaluation of potential errors in measurement," Curr Eye Res, 1986, 5(9):677-81.
Neubauer et al., "Jak2 Deficiency Defines an Essential Developmental Checkpoint in Definitive Hematopoiesis", Cell, 1998, 93(3): 397-409.
Neuner et al., "Increased IL-6 Production by Monocytes and Keratinocytes in Patients with Psoriasis," J. Invest. Dermatol., 1991, 97: 27-33.
Nicholoff et al., "Recent Insights into the immunopathogenesis of psoriasis provide new therapeutic opportunities", J. Clin. Invest., 2004, 113: 1664-1675.
Nichols et al., "The lack of association between signs and symptoms in patients with dry eye disease", Cornea, 2004, 23(8):762-770.
Nichols et al., "The repeatability of clinical measurements of dry eye", Cornea, 2004, 23(3):272-85.
Nishimoto et. al., "Improvement in Castleman's disease by humanized anti-interleukin-6 receptor antibody theraphy," Blood, 2000, 95(1):56-61.
Nishio et al., "Tyrosine kinase-dependent modulation by interferon-α of the ATP-sensitive K+ current in rabbit ventricular myocytes", FEBS Letters, 1999, 445: 87-91.
Nitta et al., "Peptide-Titanium Complex as Catalyst for Asymmetric Addition of Hydrogen Cyanide to Aldehyde", J. Am. Chem. Soc., 1992, 114: 7969-75.
Norman, "Selective JAK1 inhibitor and selective Tyk2 inhibitor patents," *Expert Opinion*, Informa Healthcare. 2012, available at: <http://informahealthcare.com/dol/pdfplus/10.1517/13543776.2012.723693>.
Norn, "Quantitative tear ferning. Clinical investigations", Acta Ophthalmol (Copenh), 1994, 72(3):369-72.
Notice of Allowance and Fee(s) Due dated Sep. 21, 2007 in connection with U.S. Appl. No. 11/313,394 (6 pages).
Notice of Hearing and Preliminary Report for EP Patent 1966202, dated Mar. 18, 2013 (7 pages).
Office Action (Non-final) dated Aug. 22, 2007 in connection with U.S. Appl. No. 11/115,702 (9 pages).
Office Action (Non-final) dated Dec. 3, 2007 in connection with U.S. Appl. No. 11/524,641 (13 pages).
Office Action (Non-final) dated Feb. 25, 2009 for U.S. Appl. No. 12/137,892 (13 pgs.).
Office Action (Final) dated Feb. 7, 2008 for U.S. Appl. No. 11/115,702 (5 pages).
Office Action (Final) dated Jan. 29, 2014 in U.S. Appl. No. 13/043,986, 10 pages.
Office Action (Final) dated Nov. 30, 2009 for U.S. Appl. No. 12/137,892 (9 pgs.).
Office Action (Non-final) dated Apr. 20, 2007 in connection with U.S. Appl. No. 11/313,394 (16 pages).

Office Action in U.S. Appl. No. 14/186,338, dated May 5, 2014, 18 pages.
Office Action received for European Application No. 06 839 328.9 (dated Jan. 22, 2009) (5 pages).
Office Action received for Japanese Application No. 2008-545733 dated Oct. 11, 2011 (5 pages).
Office Action received for New Zealand Application No. 569015 dated Feb. 24, 2010 (2 pages).
Office Action received for Singapore Application No. 2008-04386-1 (dated Aug. 24, 2010).
Office Action received for Vietnamese Patent Application No. 1-2011-03188 dated Mar. 8, 2012 as translated by foreign associate (10 pages).
Office Action, Canadian Patent Office, Application No. 2,632,466, dated May 8, 2012 (3 pages).
Office Action, China, Patent Application No. 201080033308.6 dated Aug. 2, 2013, 10 pages.
Office Action, Eurasian Patent Office dated Feb. 5, 2010.
Office Action, European Patent Office, Application No. 06 839 328.9 dated Oct. 21, 2010.
Office Action, European Patent Office, dated Nov. 6, 2009.
Office Action, Mexico, Patent Appl. No. MX/a/2008/007635 as received from foreign associate dated Jun. 15, 2010 (1 page).
Office Action, Mexico, Patent Appl. No. MX/a/2008/007635 as received from foreign associate dated Nov. 13, 2009 (4 pages).
Office Action/Examination Report received for Pakistan Application No. 211/2009 dated Jan. 18, 2010 (1 page).
Oguz et al., "The height and radius of the tear meniscus and methods for examining these parameters", Cornea, 2000, 19:497-500.
Opposition for EP Patent 1966202, filed on Jun. 21, 2012 (30 pages).
Opposition for India Patent Application No. 2365/KOLNP/2008 dated Nov. 12, 2012 (received by Applicants from Indian associate on Apr. 17, 2013) 37 pages.
Opposition, Costa Rica, translation from Foreign Associate Dated Jun. 13, 2012, 6 pages.
Opposition, Costa Rica, translation from Foreign Associate Dated Nov. 20, 2013, 9 pages.
Opposition, Ecuador Patent Office, mailed Nov. 18, 2008 1 page letter from Foreign Associate enclosing the translation (5 pages) of the Opposition.
Ortmann et al., "Janus kinases and signal transducers and activators of transcription: their roles in cytokine signaling, development and immunoregulation," Arthritis Res, 2000, 2(1): 16-32.
Ostojic et al., "Ruxolitinib: a new JAK1/2 inhibitor that offers promising options for treatment of myelofibrosis," Future Oncology, 2011, 7(9): 1035-1043.
Ostojic et al., "Ruxolifinib for the treatment of myelofibrosis," Drugs of Today, Nov. 2011, 47(11):817-827.
Ousler et al., "Factors that influence the inter-blink interval (IBI) as measured by the ocular protection index (OPI)", Invest Ophthalmol Vis Sci 2001; 43: E-abstract 56 (Poster presentation) ARVO (2002) 2 pages, downloaded from http://abstracts.iov.s.org/cgi/content/abstract/43/12/56?maxtoshow on Aug. 14, 2009.
Palmer et al., "Multiple roles of ephrins in morphogenesis, neuronal networking, and brain function," Genes & Dev., 2003, 17:1429-1450.
Panteli et al., "Serum interleukin (IL)-1, IL-2, sIL-2Ra, IL-6 and thrombopoietin levels in patients with chronic myeloproliferative diseases," British Journal of Haematology, 2005, 130: 709-715.
Pardanani, "JAK2 inhibitor therapy in myeloproliferative disorders: rationale, preclinical studies and ongoing clinical trials JAK2 inhibitor therapy in MPD," Leukemia, Jan. 2008, 22: 23-30.
Pardanani et al., "CSF3R T618I is a highly prevalent and specific mutation in chronic neutrophilic leukemia," Leukemia, 2013, 27: 1870-1873.
Parganas et al., "Jak2 is Essential for Signaling through a Variety of Cytokine Receptors," Cell, 1998, 93(3): 385-95.
Park et al., "Homogeneous Proximity Tyrosine Kinase Assays: Scintillation Proximity Assay versus Homogeneous Time-Resolved Fluorescence", Analytical Biochemistry, 1999, 269: 94-104.
Parks, "Tofacitinib and Other Kinase Inhibitors Offer New Approach to Treating Rheumatoid Arthritis," Rheumatologist, Jun. 2013, pp.

(56) References Cited

OTHER PUBLICATIONS 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.
Patani et al., "Bioisosterism: A Rational Approach in Drug Design", Chem. Rev., 1996, 96: 3147-3176.
Patrick, "An Introduction to medicinal chemistry" *Oxford University Press Inc.*, New York, 1995 (31 pages) (cited in Opposition from India dated Nov 12, 2012.
Pearce et al., "Spatial location studies on the chemical composition of human tear ferns", Ophthalmic Physiol Opt, 2000, 20(4):306-13.
Pearce et al., "An improved fluorophotometric method for tear turnover assessment", Optom Vis Sci, 2001, 78(1):30-36.
Pedranzini et al., "Pyridone 6, A Pan-Janus-Activated Kinase Inhibitor, Induces Growth Inhibition of Multiple Myeloma Cells," Cancer Res., 2006, 66(19):9714-9721.
Pensyl et al., "The repeatability of tear mucus ferning grading", Optom Vis Sci, 1998, 75(8):600-4.
Pernis et al., "JAK-STAT signaling in asthma." J Clin Invest, 2002, 109(10): 1279-83.
Peters et al., "Functional Significance of Tie2 Signaling in the Adult Vasculature", 2004, ©The Endocrine Society (21 pages).
Pflugfelder et al., "Evaluation of subjective assessments and objective diagnostic tests for diagnosing tear-film disorders known to cause ocular irritation," Cornea, 1998, 17(1):38-56.
Pillonel "Evaluation of phenylaminopyrimidines as antifungal protein kinase inhibitors," Pest Management Science, Wiley & Sons, Jun. 2005, 61: 1069-1076.
Pirard et al., "Classification of Kinase Inhibitors Using BCUT Descriptors", J. Chem. Inf. Comput. Sci., 2000, 40: 1431-1440.
Pisella et al., "Flow cytometric analysis of conjunctival epithelium in ocular rosacea and keratoconjunctivitis sicca," Ophthalmology, 2000, 107:1841-1849.
Pisella et al., "Conjunctival proinflammatory and proapoptotic effects of latanoprost, preserved timolol and unpreserved timolol: an ex vivo and in vitro study." Invest Ophthalmol Vis Sci, 2004, 45:1360-1368.
Phillipines Examination Report in Phillipines Application No. 1-2013-501001, dated Mar. 23, 2017, 3 pages.
Portnaya et. al., "Azomethine dyes. IV. Indoaniline dyes derived from heterocyclic N-substituted 1-hydroxy-2-naphthamide," Ts Vses Nauchn Issled Kinofotoinst, 1960, Issue 40, 106-8 (with English abstract 20 pages total).
Prchal et al, eds. Williams Hematology. 8th ed., New York: McGraw-Hill; 2010 **Too Voluminous to Provide.
Press Release dated Sep. 18, 2008: "Incyte's Topical JAK Inhibitor Demonstrates Positive Proof-of-Concept Results in Patients with Mild to Moderate Psoriasis" (4 pages).
Prezent et al., "Boron chelates as intermediates in the synthesis of new functionalized pyridines and pyrimidines from a, a-dioxoketene aminals", Proceedings of the International Conference on the Chemistry of Boron, vol. 11 (2003) (abstract only—1 page).
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Punwani, Naresh, et al. "Efficacy and safety of topical INCB018424, a selective Janus kinase 1 & 2 (JAK1&2) inhibitor in psoriasis." Journal of the American Academy of Dermatology. vol. 60. No. 3. 360 Park Avenue South, New York, NY 10010-1710 USA: Mosby-Elsevier, 2009.
Quesada et al, "One-pot conversion of activated alcohols into 1,1-dibromoalkenes and terminal alkynes using tandem oxidation processes with manganese dioxide", Tetrahedron, 2006, 62: 6673-6680.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957, 115(15):3109-3117.
Ravin, "Preformulation", Remington's Pharmaceutical Sciences, 17th ed., Mack Publishing Company, Easton, Pa., 1985, Chapter 76, 1409-1423.
Raza et al., "Apoptosis in bone marrow biopsy samples involving stromal and hematopoietic cells in 50 patients with myelodysplastic syndromes," Blood, Jul. 1995, 86(1): 268-76.
Raza et al., "Phase 2 Study of lenalidomide in transfusion-dependent, low-risk, and intermediate-1 risk myelodysplastic syndromes with karyotypes other than deletion 5q," Blood, Jan. 2008, 111(1): 86-93.
Raza et al., "Novel insights into the biology of myelodyplastic syndromes: excessive apoptosis and the role of cytokines," Int J Hematol, 1996, 63:265-278.
Raza et al., "The Myelodysplastic Syndromes in 1996: Complex Stem Cell Disorders Confounded by Dual Actions of Cytokines," Leuk Res, 1996, 20:881-890.
Ren et al., "Compounds and Compositions as Protein Kinase Inhibitors," U.S. Appl. No. 60/578,491, filed Jun. 10, 2004 (56 pages).
Response and Amendment dated Aug. 25, 2009 to non-final Office Action for U.S. Appl. No. 12/137,892 (34 pgs.).
Response and Amendment in Reply to Action dated Apr. 20, 2007 filed Jul. 17, 2007 for U.S. Appl. No. 11/313,394 (39 pages).
Response to Action of Aug. 22, 2007 dated Nov. 19, 2007, U.S. Appl. No. 11/115,702 (7 pages).
Response to Restriction Requirement dated May 29, 2007, U.S. Appl. No. 11/115,702 (8 pages).
Restriction Requirement dated Mar. 6, 2007 in connection with U.S. Appl. No. 11/115,702 (8 pages).
Reuters, "Jakafi (ruxolitinib) improved advanced pancreas cancer outcomes in mid-stage trial," Internet Citation, Aug. 21, 2013, pp. 1-2, XP002717211, Retrieved from Internet: URL: http://www.curetoday.com/index.cfm/fuseaction/news.showNewsArticle/id/13/news_id/3785 [retrieved on Nov. 29, 2013].
Riese et al., "Inhibition of JAK kinases in patients with rheumatoid arthritis: scientific rationale and clinical outcomes," Best Practice & Research Clinical Rheumatology, 2010, 513-526.
Roberts et al., "Trends in the Risks and Benefits to Patients With Cancer Participating in Phase 1 Clinical Trials," JAMA, 2004, 292(17):2130-2140.
Robin et al., "In vivo transillumination biomicroscopy and photography of meibomian gland dysfunction," Opthalmology, 1985, 92:1423-6.
Rodig et al., "Disruption of the Jak1 gene demonstrates obligatory and nonredundant roles of the Jaks in cytokine-induced biologic responses." Cell, 1998, 93(3): 373-83.
Rolando et al., "Tear mucus crystallization in children with cystic fibrosis", Ophthalmologica, 1988, 197(4):202-6.
Rolando et al., "Tear mucus ferning test in keratoconjunctivitis sicca", Holly FJ, Lamberts DW, MacKeen DL (eds.): The preocular tear film in health, disease, and contact lens wear,. 1st Intern Tear Film Symposium. Lubbock (Texas, USA), Dry Eye Institute, 1986, 203-210.
Rolando et al., "The effect of hyperosmolarity on tear mucus ferning", Fortschr Ophthalmol, 1986, 83:644-646.
Rolando et al., "The Ocular Surface and Tear Film and Their Dysfunction in Dry Eye Disease," Survey of Ophthalmology, Mar. 2001, 45(Supplement 2): S203-S210.
Rolando, "Tear mucus ferning test in normal and keratoconjunctivitis sicca eyes," Chibret Int J Ophthalmol, 1984, 2(4):32-41.
Rollison et al., "Epidemiology of myelodysplastic syndromes and chronic myeloproliferative disorders in the United States, 2001-2004, using data from the NAACCR and SEER programs," Blood, Jul. 2008, 112(1): 45-52.
Roudebush et al., "Pharmacologic manipulation of a four day marine delayed type hyper sensitivity model", Agents Actions, 1993, 38(1-2):116-21.
Rousvoal et al. "Janus kinase 3 inhibition with CP-690,550 prevents allograft vasculopathy", Transpl Int., 2006, 19(12):1014-21.

(56) References Cited

OTHER PUBLICATIONS

Saemann et al., "Prevention of CD40-triggered dendritic cell maturation and induction of T-cell hyporeactivity by targeting of Janus kinase 3," Am J Transplant, 2003, 3(11): 1341-9.
Saemann et al., "Suppression of early T-cell-receptor-triggered cellular activation by the Janus kinase 3 inhibitor MHI-P-154," Transplantation, 2003, 75(11): 1864-1872.
Saettone et al., "Ocular inserts for topical delivery," Advanced Drug Delivery Reviews, 1995, 16: 95-106.
Samanta et al., "Janus kinase 2: a critical target in chronic myelogenous leukemia," Cancer Res., Jul. 2006, 66(13):6468-72.
Santini et al., "Hepcidin Levels and Their Determinants in Different Types of Myelodysplastic Syndromes," PLoS One, 2011, 6(8): e23109, pp. 1-8.
Sawada et al, "Increased Lipophilicity and Subsequent Cell Partitioning Decrease Passive Transcellular Diffusion of Novel, Highly Lipophilic Antioxidants", The Journal of Pharmacology and Experimental Therapeutics, 1999, 288(3):1317-1326, p. 1321, compound 26.
Schiffer, "Clinical issues in the management of patients with myelodysplasia," Hematology Am Soc Hematol Educ Program, 2006, 205-10.
Schiffer, "Myelodysplasia: the good, the fair and the ugly," Best Pract Res Clin Haematol, Mar. 2007, 20(1): 49-55.
Schindler et al., "Hormones and Signaling: Cytokines and STAT Signaling," Adv Pharmacol., 2000, 47:113-74.
Schmidt et al., "Rituximab in autoimmune bullous diseases: mixed responses and adverse effects," British Journal of Dermatology, 2007, 352-356.
Schrader et al., "Animal Models of Dry Eye," Developmental Ophthalmology, 2008, 41: 298-312.
Scott et al., "Jaks, STATs, Cytokines, and Sepsis." Clin Diagn Lab Immunol, 2002, 9(6): 1153-9.
Search Report in TW Application No. 100117866, dated Dec. 2014, 1 page.
Seefeld et al, "Discovery of 5-pyrrolopyridinyl-2-thiophenecarboxamides as potent AKT kinase," Bioorganic & Medicinal Chemistry Letters, 2009, 19(8):2244-2248.
Seela et al., "Synthesis of Pyrrolo[2,3-d]pyrimidine 2', 3'-Dideoxyribenucleosides Related to 2',3'-Dideoxyadenosine and 2',3'-Dideoxgtuanosine and Inhibitory Activity of 5'-Triphosphates on HIV-1 Reverse Transcriptase", Helvetica Chimica Acta, 1991, 74(3), 554-64.
Seki, "STAT3 and MAPK in human lung cancer tissues and suppression of oncogenic growth by JAB and dominant negative STAT3", Int J Oncol., 2004, 24(4):931-4.
Seto et al., "Enhanced Th2 cell-mediated allergic inflammation in Tyk2-deficient mice." J Immunol, 2003, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell, Aug. 2002, 2:117-125.
Shi et al., "The pharmacokinetics, pharmacodynamics, and safety of orally dosed INCB018424 phosphate in healthy volunteers", Journal of Clinical Pharmacology, Dec. 2011, 51(12): 1644-1654.
Shimazaki et al., "Meibomian gland dysfunction in patients with Sjogren syndrome", Ophthalmology, 1998, 105(8):1485-8.
Silverman et al., "Further analysis of trials with azacitidine in patients with myelodysplastic syndrome: studies 8421, 8921, and 9221 by the Cancer and Leukemia Group B," J Clin Oncol, Aug. 2006, 24(24): 3895-903.
Silverman et al., "Randomized controlled trial of azacitidine in patients with the myelodysplastic syndrome: a study of the cancer and leukemia group B," J Clin Oncol, May 2002, 20(10): 2429-40.
Sloand et al., "Factors affecting response and survival in patients with myelodysplasia treated with immunosuppressive therapy," J Clin Oncol, May 2008, 26(15): 2505-11.
Smith et al, "Basic pathogenic mechanisms operating in experimental model acute anterior uveitis," Immunology and Cell Biology, 1998, 76: 497-512.

Smolen et al, "Effect of interleukin-6 receptor inhibition with tocilizumab in patients with rheumatoid arthritis (OPTION study): a double-blind, placebo-controlled, randomized trial", Lancet, 2008, 371:987.
Sonbol et al., "Comprehensive review of JAK inhibitors in myeloproliferative neoplasms," Therapeutic Advances in Hematology, 2013, 4(1): 15-35.
Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.
Spoerl et al., "Activity of therapeutic JAK 1/2 blockade in graft-versus-host disease," *Blood*, 2014, 123(24): 3832-3842.
Sriram et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodegeneration", J. Biol. Chem., 2004, 279(19):19936-47.
Staerk et. al., "JAK1 and Tyk2 activation by the homologous polycythemia vera JAK2 V617F mutation: cross-talk with IGF1 receptor", J Biol Chem., 2005, 280:41893-41899.
State Intellectual Property Office, PR China, Office Action, dated Sep. 3, 2010 Pat. Appl. No. 200680052750.7 (8 pages).
Steensma et al., "The JAK2 V617F activating tyrosine kinase mutation is an infrequent event in both "atypical" myeloproliferative disorders and mylodysplastic syndromes," Blood, Aug. 2005, 106(4): 1207-9.
Stirewalt et al., "Predictors of relapse and overall survival in Philadelphia chromosome-positive acute lymphoblastic leukemia after transplantation", Biol Blood Marrow Transplant., Mar. 2003, 9(3):206-12.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).
STN Search, Oct. 20, 2009 (601 pages).
STN Search, Sep. 20, 2009 (864 pages).
Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.
Sullivan et al., "4th International Conference on the Lacrimal Gland, Tear Film & Ocular Surface and Dry Eye Syndromes, Nov. 20, 2004" (2 pages).
Symington et al., "The relationship of serum IL-6 levels to acute graft-versus-host disease and hepatorenal disease after human bone marrow transplantation," Transplantation, 1992, 54(3): 457-462 (Abstract only).
Takahashi et al., "Solvent-Free Reaction Using Phosphonium Salts: Chlorination of Hydroxyheteroaromatics and dehydration of Primary Amides", Heterocycles, 2006, 68: 1973-1979.
Takano et al., "Inflammatory cells in brush cytology samples correlate with the severity of corneal lesions in atopic keratoconjunctivitis", Br J Ophthalmol, 2004, 88:1504-5.
Takemoto et al., "Proliferation of adult T cell leukemia/lymphoma cells is associated with the constitutive activation of JAK/STAT proteins." Proc Natl Acad Sci USA, 1997, 94(25): 13897-902.
Tamura et al., "Involvement of Human Interleukin 6 in Experimental Cachexia Induced by a Human Uterine Cervical Carcinoma Xenograft," Clin. Cancer Res., Nov. 1995, 1: 1353-1358.
Tan et al, "Racemization processes at a quaternary carbon center in the context of the asymmetric Michael reaction", Tetrahedron Lett., 2001, 42(30):5021-5023.
Tang et al., "Knowledge-based design of 7-azaindoles as selective B-Raf inhibitors", Bioorganic & Medicinal Chemistry Letters, 2008, 18(16):4610-4614.
Tasian et al., "Understanding the biology of CRLF2-overexpressing acute lymphoblastic leukemia", Critical Reviews in Oncogenesis, 2011, 16(1): 13-24.
Tefferi et al. "The Clinical Phenotype of Myelofibrosis Encompasses a Chronic Inflammatory State that is Favorably Altered by

(56) References Cited

OTHER PUBLICATIONS

INCB018424, A Selective Inhibitor of JAK1/2" Poster #2804 at the American Society of Hematology Annual Meeting (ASH), Dec. 7, 2008, (18 pages).
Tefferi, "Primary myelofibrosis: 2012 update on diagnosis, risk stratification, and management," American Journal of Hematology, Dec. 2011, 86(12): 1017-1026.
Tefferi et al., "Serious adverse events during ruxolitinib treatment discontinuation in patients with myelofibrosis", Mayo Clinic Proceedings, Dec. 2011, 86(12): 1188-1191.
Textbook of Clinical Trials 264 (D. Machin et al., eds., 2nd ed., 2006).
Thompson et al., "Photochemical Preparation of a Pyridone Containing Tetracycle: A Jak Protein Kinase Inhibitor", Bioorganic & Medicinal Chemistry Letters, 2002, 12: 1219-1223.
Tiffany et al., Meniscectomy using the Tearscope-plus (ARVO abstract). Invest Ophthalmol Vis Sci, 2001,42: s37 (1 page).
Tiffany, "Refractive index of meibomian and other lipids", Curr Eye Res, 1986, 5:887-9.
Ting et al., "The Synthesis of substituted bipiperidine amide compounds as CCR3 antagonists", Bioorg. Med. Chem. Lett., 2005, 15(5): 1375-1378.
Toyonaga, "Blockade of constitutively activated Janus kinase/signal transducer and activator of transcription-3 pathway inhibits growth of human pancreatic cancer", Cancer Lett., 2003, 201(1):107-16.
Trikha et al., "Targeted anti-interleukin-6 monoclonal antibody therapy for cancer: a review of the rationale and clinical evidence," Clinical Cancer Research, 2003, 9: 4653-4665.
Tsubota et al., "Brush cytology for the evaluation of dry-eye", Nippon Ganka Gakkai Zasshi, 1990, 94:224-30 (English Abstract).
Tsubota et al., "Conjunctival brush cytology", Acta Cytol, 1990, 34(2):233-5.
Tsubota et al., "Detection by brush cytology of mast cells and eosinophils in allergic and vernal conjunctivitis," Cornea, 1991, 10(6):525-31.
Ueda et al., "1,2-Benzisoxazol-3-yl Diphenyl Phosphate: A New, Reactive Activating Agent for the Synthesis of Amides, Esters, and Peptides via Condensation", J. Org. Chem., 1985, 50:760-763.
Vaillant et al., "Turbidity of pulpy fruit juice: A key factor for predicting cross-flow microfiltration performance," J Membrane Sci., 2008, 325:404-412.
Van Best et al., "Measurement of basal tear turnover using a standardized protocol", Graefe's Arch Clin Exp Ophthahnol, 1995, 233:1-7.
Van Bijsterveld, "Diagnostic tests in the sicca syndrome", Arch Ophthalmol, 1969, 82:10-14.
Van Rhee et al., "Anti-Interleukin-6 Monoclonal man's Disease," J. Clin. Oncol., 2010, 28(23):3701-3708.
Vanhoutte, "Selective JAK1 Inhibition in the Treatment of Rheumatoid Arthritis: Proof of Concept with GLPG0634," Arthritis Rheum, 2012, 64.10: S1051-1.
Vannucchi et al., "The mTOR Inhibitor, RAD001, Inhibits the Growth of Cells From Patients with Myeloproliferative Neoplasms", Blood: ASH Annual Meeting Abstracts, 51$^{st}$ Annual Meeting of the American Society of Hematology, 2009, 114(22), 2 pages.
Vannucchi et al., "Inhibitors of PI3K/Akt and/or mTOR Inhibit the Growth of Cells of Myeloproliferative Neoplasms and Synergize with JAK2 Inhibitor and Interferon", Blood, 2011, 118(21): 1638-1639, XP008150742ASH Annual Meeting Abstract 3835 American Society of Hematology.
Vannucchi et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, 2009, 114(22), 2 pages.
Vardiman et al., "Atypical chronic myeloid leukaemia, BCR-ABL1 negative," in: Swerdlow, et al., WHO Classification of Tumors of Haematopoietic and Lymphoid Tissues (ed 4th). Lyon: IARC Press; 2008:80-81.

Vardiman et al., "The World Health Organization (WHO) classification of the myeloid neoplasms," Blood, 2002, 100:2292-2302.
Vardiman et al., "The 2008 revision of the World Health Organization (WHO) Classification of myeloid neoplasms and acute leukemia: rationale and important changes," Blood, 2009, 114:937-951.
Vasilevsky et al., "Ethyl Vinyl Ether—an Agent for Protection of the Pyrazole NH-Fragment. A Convenient Method for the Preparation of N-Unsubstituted 6Alkynylpyrazoles", Heterocycles, 2003, 60(4):879-886.
Venugopal et al., "Special clinical concerns/problems in the management of MDS and secondary acute myeloid leukemias," Cancer Treat Res, 2001, 108: 257-65.
Verma et al., "Jak family of kinases in cancer", Cancer and Metastasis Reviews, 2003, 22(4): 423-434, DOI: 10.1023/A:1023805715476.
Verstovsek, "Therapeutic Potential of JAK2 Inhibitors", Hematology Am Soc Hematol Educ Program, 2009:636-42.
Verstovsek, et al., Blood (ASH Annual Meeting Abstracts) 2007 110: Abstract 558.
Verstovsek, et al., Blood (ASH Annual Meeting Abstracts) 2009 114: Abstract 311.
Verstovsek, et al., Blood (ASH Annual Meeting Abstracts) 2010 116: Abstract 313.
Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).
Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).
Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).
Verstovsek, Srdan et al., "Characterization of JAKS V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor, INCB018424, "50th ASH Annual Meeting and Exposition, Abstract No. 2802 (2008).
Vitali et al. "The European Community Study Group on diagnostic criteria for Sjogren's syndrome. Sensitivity and specificity of tests for ocular and oral involvement in Sjogren's syndrome," Ann Rheum Dis, 1994, 53(10): 637-47.
Wagh et al., "Polymers used in ocular dosage form and drug delivery systems", Asian J. Pharm., Jan. 2008, 12-17.
Wang and Deisboeck, "Mathematical modeling in cancer drug discovery," Drug Discovery Today, 2014, 145-150.
WebMD. "Diabetes Health Center." Available at: < http://diabetes.webmd.com/guide/diabetestreatment_care >. 3 pages, retrieved from the Internet May 28, 2013.
Webster's New World Medical Dictionary, Sjogren's syndrome, 2003, Wiley Publishing, printed fro http://www.credoreference.com/entry/webstermed/sjogren_s_syndrome, 2 pages.
Weiss et al., "Evaluation of a Series of Naphthamides as Potent, Orally Active Vascular Endothelial Growth Factor Receptor-2 Tyrosine Kinase Inhibitors", J. Med Chem., 2008, 51:1668-1680.
Welch et al., "An approach to a more standardized method of evaluating tear film break-up time", Invest Ophthalmol Vis Sci, 2003, 2485/B324 (abstract only—2 pages).
White et al., "Human basic tear fluid osmolality. I. Importance of sample collection strategy", Acta Ophthalmol (Copenh), Aug. 1993, 71(4):524-9.

(56) References Cited

OTHER PUBLICATIONS

Wilks, "The JAK kinases: Not just another kinase drug discovery target," Seminars in Cell & Developmental Biology, 2008, 319-328.
Williams and Ibrahim, "Carbodiimide Chemistry: Recent Advances", Chem. Rev., 1981, 81:589-636.
Williams et al., "Dissecting Specificity in the Janus Kinases: The Structures of JAK-Specific Inhibitors Complexed to the JAK1 and JAK2 Protein Tyrosine Kinase Domains," Journal of Molecular Biology, 2009, 219-232.
Williams, et al. "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
Wolf et al., "Burger's Medicinal Chemistry and Drug Discovery", 5th Ed. Part I, 1995, 975-977.
Wu et al., One-Pot Two-Step Microwave-Assisted Reaction in Construction 4,5-Disubstituted Pyrazolopyrimidines Organic Letters, 2003, 5(20): 3587-3590.
Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.
Yamamura et al., "Circulating interleukin-6 levels are elevated in adult T-cell leukaemia/lymphoma patients and correlate with adverse clinical features and survival," Br. J. Haematol., 1998, 100: 129-134.
Yamaoka et al., "Janus kinase (JAK) inhibitors in rheumatoid arthritis", Current Rheumatology Reviews, Nov. 2011, 7(4): 306-312.
Yang et al., "Constitutive NF-KB activation confers interleukin 6 (IL6) independence and resistance to dexamethasone and Janus kinase inhibitor INCB018424 in murine plasmacytoma cells", Journal of Biological Chemistry, Aug. 2011, 286(32):27988-27997.
Yao et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 2008, 58(11):3485-3497.
Yao, et al., "Glucocorticoid Excess in Mice Results in Early Activation of Osteoclastogenesis and Adipogenesis and Prolonged Suppression of Osteogenesis", Arthritis and Rheumatism, 2008, 58(6), 1674-1686.
Yokoi et al., "A newly developed video-meibography system featuring a newly designed probe", Jpn J Ophthalmol, 2007, 51: 53-6.
Yokoi et al., "Assessment of meibomian gland function in dry eye using meibometry", Arch Ophthalmol, 1999, 117:723-9.
Yokoi et al., "Correlation of tear lipid layer interference patterns with the diagnosis and severity of dry eye", Am J Ophthalmol, 1996, 122:818-24.
Yokoi et al., "Non-invasive methods of assessing the tear film", Exp Eye Res, 2004, 78:399-407.
Younes et al., "Phase I Study of a Novel Oral Janus Kinase 2 Inhibitor, SB1518, in Patients With Relapsed Lymphoma: Evidence of Clinical and Biologic Activity in Multiple Lymphoma Subtypes," J. Clin. Oncol., 2012, 30(33):4161-4167.
Yu et al., "Role of Janus Kinase/Signal Transducers and Activators of Transcription in the Pathogenesis of Pancreatitis and Pancreatic Cancer," Gut and Liver, Oct. 2012, 6(4): 417-422.
Yu et al., "Constitutive activation of the Janus kinase-STAT pathway in T lymphoma overexpressing the Lck protein tyrosine kinase," J Immunol., 1997, 159(11):5206-10.
Zaidi et al., "Dermatology in Clinical Practice," Springer, 2010, 157 pages.
Zheng et al., "Discovery of INC13108201PF-4178903, a potent, selective, and orally bioavailable dual CCR2 and CCR5 antagonist", Bioorganic & Medicinal Chemistry Letters, 2011, 21: 1442-45.
Zoppellaro et al., "A Multifunctional High-Spin Biradical Pyrazolylbipyridine-bisnitronylnitroxide", Org. Lett., 2004, 6(26):4929-4932.
Zou et al., "Signaling Pathways Activated by Oncogenic Forms of Abl Tyrosine Kinase." Journal of Biological Chemistry, 1999, 274(26):18141-18144.
Australian Office Action in Australian Application No. 2016204689, dated Mar. 22, 2017, 4 pages.
Eurasian Office Action in Eurasian Application No. 201291310, dated Mar. 9, 2017, 4 pages (English Translation).
Eurasian Search Report in Eurasian Application No. 201200132, dated Sep. 1, 2016, 6 pages (English Translation).
European Search Report in European Application No. 16197502.4, dated Mar. 20, 2017, 15 pages.
Korean Office Action in Korean Application No. 10-2012-7033308, dated Mar. 21, 2017, 6 pages (English Translation Only).
Arber et al., "The 2016 revision to the World Health Organization classification of myeloid neoplasms and acute leukemia," Blood, May 2016, 2391-2405.
Bondoux et al., "Palladium-catalyzed C-C coupling: efficient preparation of new 5-thio-B-D-xylopyranosides as oral venous antithrombotic drugs," Tetrahedron Letters, 2009, 50(27): 3872-3876.
Cazzola et al., "Myelodysplastic/Myeloproliferative Neoplasms," American Society of Hematology (ASH Education Book), 2011, 264-272.
Gurram et al., "C-C Cross-Coupling Reactions of )6-Alkyl-2-Haloinosine Derivatives and a One-Pot Cross-Coupling/)6-Deprotection Procedure," Chem Asian J., Aug. 2012, 7(8): 1853-1861.
Patel et al., "Formulation and Evaluation of Controlled Release Matrix Tablet of a Model Antibiotic Drug," Am. J. PharmTech. Res., 2012 2(2): 681-694.
Namour et al., "Once-daily High Dose Regimens of GLPG0634 in Healthy Volunteers are Safe and Provide Continuous Inhibition of JAK1 but not JAK2," ACR/ARHP Annual Meeting 12, Nov. 9-14, 2012, Abstract Number: 1331.
Scott et al., "Jaks, STATs, Cytokines, and Sepsis," British Journal of Haematology, Mar. 2010, 148(6): 944-947.
Winfield, Pharmaceutical Practice, Ophthalmic Products-pH adjustment, Churchill Livingstone, 2004, 264-271.
Japanese Office Action in Japanese Application No. 2015-561582, dated Feb. 13, 2018, 9 pages (English Translation).
European Communication pursuant to Article 94(3) EPC in European Application No. 14753182.6, dated Nov. 6, 2017, 10 pages.
Chinese Office Action in Chinese Application No. 201480052299.3, dated Jan. 25, 2018, 13 pages.
Taiwanese Office Action in Taiwanese Application No. 103126987, dated Dec. 28, 2017, 9 pages (English Translation).
Canadian Office Action in Canadian Application No. 2,738,520, dated Jul. 16, 2018, 7 pages.
Cervantes et al., "Three-year efficacy, safety, and survival findings from COMFORT-II, a phase 3 study comparing ruxolitinib with best available therapy for mylefibrosis," Blood, Dec. 12, 2013, 122(25):4047-4053.
Chinese Office Action in Chinese Application No. 201610989522.8, dated Jun. 4, 2018, 19 pages.
ClinicalTrials.gov, "Topical Ruxolitinib for the Treatment of Vitiligo," Retrieved on Dec. 19, 2018, retrieved from URL <clinicaltrials.gov/ct2/show/NCT02809976>, 6 pages.
ClinicalTrials.gov, "A Study to Evaluate the Safety and Efficacy of INCB018424 Phosphate Cream Applied Topically to Adults With Atopic Dermatitis," Retrieved on Dec. 19, 2018, retrieved from URL <https://clinicaltrials.gov/ct2/show/NCT03011892>, 7 pages.
Ecuador Examination Report in Ecuador Application No. SP-08-8540, dated Jun. 13, 2017, 30 pages.
Eurasian Office Action in Eurasian Application No. 201691745, dated Mar. 20, 2019, 4 pages.
European Communication pursuant to Article 94(3) EPC in European Application No. 14753182.6, dated Sep. 10, 2018, 7 pages.
European Extended Search Report in European Application No. 18191992.9, dated Jan. 18, 2019, 10 pages.
Furqan et al., "Dysregulation of JAK-STAT pathway in hematological malignancies and JAK inhibitors for clinical application," Biomarker Research 2013, 1(1):1-10.
Hengge et al., "Adverse Effects of Topical Glucocorticosteroids," J Am Acad Dermatol., Jan. 2006, 54(1):1-15.

(56) References Cited

OTHER PUBLICATIONS

Indian Office Action in Indian Application No. 2177/DELNP/2014, dated May 8, 2018, 4 pages.

Japanese Office Action in Japanese Application No. 2017-246-134, dated Oct. 16, 2018, 12 pages.

Kim et al., Abstract #1956, "A Phase 2, Randomized, Dose-Ranging, Vehicle-and Active-Controlled Study to Evaluate the Safety and Efficacy of Ruxolitinib Cream in Adult Patients with Atopic Dermatitis," Presentation, Presented at the 27th European Academy of Dermatology and Venereology Congress, Sep. 12-16, 2018, Paris, France, 11 pages.

Kim et al., "Clinical significances of preoperative serum interleukin-6 and C-reactive protein level in operable gastric cancer," BMC Cancer, May 20, 2009, 9(155):1-9.

O'shea et al., "Janus Kinase Inhibitors in Autoimmune Diseases," Ann Theum Dis., Apr. 2013, 72(Suppl 2):iii111-iii115.

Office Action Received for New Zealand Application No. 748000, dated Dec. 24, 2018, 2 pages.

Press Release dated Sep. 13, 2018: "Incyte Announces Positive Data from Phase 2b Trial of Ruxolitinib Cream in Patients with Atopic Dermatitis" (2 pages).

Product Monograph, "Jakavi," Prepared Jun. 15, 2012, Last revised, Sep. 28, 2018, 51 pages.

Roy et al., "Formulation and design of sustained release matrix tablets of metformin hydrochloride: Influence of hypromellose and polyacrylate polymers," Int J Appl Basic Med Res., Jan. 2013, 3(1):55-63.

Srdan et al., "Safety and Efficacy of INCB018424, a JAK1 and JAK2 Inhibitor, in Myelfibrosis," The New England Journal of Medicine, Sep. 16, 2010, 363:1117-1127.

Stahl et al., "Topical Administration," Handbook of Pharmaceutical Salts, 22(43):110.

Verstovsek et al., "Efficacy, safety and survival with ruxolitinib in patients with mylefibrosis:resuts of a median 2-year follow-up of COMFORT-I," Haematologica, 2013, 98(12):1865-1871.

Patel et al., "Formulation and Evaluation of Controlled Release Matrix Tablet of a Model Antibiotic Drug," Am. J. PharmTech. Res., 2012 2(2).

\* cited by examiner

AZETIDINYL PHENYL, PYRIDYL OR PYRAZINYL CARBOXAMIDE DERIVATIVES AS JAK INHIBITORS

This application is a continuation of Ser. No. 14/697,236, filed Apr. 27, 2015, which is a continuation of Ser. No. 14/186,338, filed Feb. 21, 2014, which is a continuation of Ser. No. 13/526,957, filed Jun. 19, 2012, now U.S. Pat. No. 8,691,807, which claims the benefit of priority of U.S. Provisional Application Nos. 61/498,942, filed Jun. 20, 2011, and 61/591,094, filed Jan. 26, 2012, each of which is incorporated herein by reference in its entirety.

TECHNICAL FIELD

The present invention provides azetidinyl phenyl, pyridyl, or pyrazinyl carboxamide derivatives, as well as their compositions and methods of use that inhibit the activity of Janus kinases (JAKs) and are useful in the treatment of diseases related to the activity of JAK including, for example, inflammatory disorders, autoimmune disorders, cancer, and other diseases.

BACKGROUND

Protein kinases (PKs) regulate diverse biological processes including cell growth, survival, differentiation, organ formation, morphogenesis, neovascularization, tissue repair, and regeneration, among others. Protein kinases also play specialized roles in a host of human diseases including cancer. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs). There are four known mammalian JAKs: JAK1 (Janus kinase-1), JAK2, JAK3 (also known as Janus kinase, leukocyte; JAKL; and L-JAK), and TYK2 (protein-tyrosine kinase 2).

Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus erythematosus, thyroiditis, myocarditis), and illnesses such as scleroderma and osteoarthritis (Ortmann, R. A., T. Cheng, et al. (2000) *Arthritis Res* 2(1): 16-32).

Deficiencies in expression of JAKs are associated with many disease states. For example, JAK1-/- mice are runted at birth, fail to nurse, and die perinatally (Rodig, S. J., M. A. Meraz, et al. (1998) *Cell* 93(3): 373-83). JAK2-/- mouse embryos are anemic and die around day 12.5 postcoitum due to the absence of definitive erythropoiesis.

The JAK/STAT pathway, and in particular all four JAKs, are believed to play a role in the pathogenesis of asthmatic response, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Activation of JAK/STAT in cancers may occur by cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm*. 49:349-355, 2002). Activation of STAT signaling, as well as other pathways downstream of JAKs (e.g., Akt), has been correlated with poor prognosis in many cancer types (Bowman, T., et al. *Oncogene* 19:2474-2488, 2000). Elevated levels of circulating cytokines that signal through JAK/STAT play a causal role in cachexia and/or chronic fatigue. As such, JAK inhibition may be beneficial to cancer patients for reasons that extend beyond potential anti-tumor activity.

JAK2 tyrosine kinase can be beneficial for patients with myeloproliferative disorders, e.g., polycythemia vera (PV), essential thrombocythemia (ET), myeloid metaplasia with myelofibrosis (MMM) (Levin, et al., *Cancer Cell*, vol. 7, 2005: 387-397). Inhibition of the JAK2V617F kinase decreases proliferation of hematopoietic cells, suggesting JAK2 as a potential target for pharmacologic inhibition in patients with PV, ET, and MMM.

Inhibition of the JAKs may benefit patients suffering from skin immune disorders such as psoriasis, and skin sensitization. The maintenance of psoriasis is believed to depend on a number of inflammatory cytokines in addition to various chemokines and growth factors (JCI, 113:1664-1675), many of which signal through JAKs (*Adv Pharmacol*. 2000; 47:113-74).

Thus, new or improved agents which inhibit kinases such as JAKs are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases, diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics. The compounds of the invention, as well as its compositions and methods described herein are directed toward these needs and other ends.

SUMMARY

The present invention provides, inter alia, compounds of Formula I:

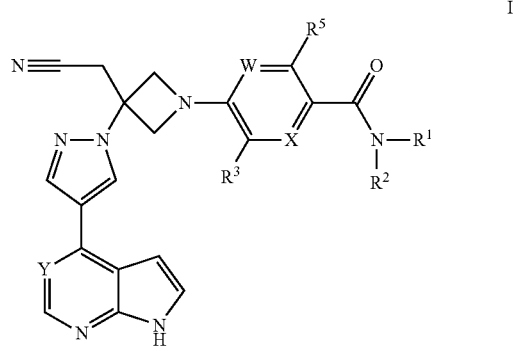

or pharmaceutically acceptable salts thereof; wherein the variables are defined infra.

The present invention further provides compositions comprising a compound of Formula I, or a pharmaceutically acceptable salt thereof, and a pharmaceutically acceptable carrier.

The present invention further provides methods of modulating an activity of JAK1 comprising contacting JAK1 with a compound of Formula I, or a pharmaceutically acceptable salt thereof.

The present invention further provides methods of treating a disease or a disorder associated with abnormal kinase expression or activity in a patient by administering to a patient a therapeutically effective amount of a compound of Formula I, or a pharmaceutically acceptable salt thereof.

The present invention further provides methods of treating an autoimmune disease, a cancer, a myeloproliferative disorder, an inflammatory disease, a bone resorption disease, or organ transplant rejection in a patient in need thereof, comprising administering to said patient a therapeutically effective amount of a compound of Formula I, or a pharmaceutically acceptable salt thereof.

The present invention also provides compounds of Formula I, or pharmaceutically acceptable salts thereof, as described herein for use in treatment of autoimmune diseases, cancer, myeloproliferative disorders, inflammatory diseases, a bone resorption disease, or organ transplant rejection.

The present invention further provides compounds of Formula I as described herein, or pharmaceutically acceptable salts thereof, for use in modulating JAK1.

The present invention also provides uses of compounds of Formula I as described herein, or pharmaceutically acceptable salts thereof, for the preparation of medicaments for use in methods of modulating JAK1.

The details of one or more embodiments of the invention are set forth in the description below. Other features, objects, and advantages of the invention will be apparent from the description and claims.

DETAILED DESCRIPTION

The present invention provides, inter alia, a compound of Formula I:

or a pharmaceutically acceptable salt thereof; wherein:
X is N or $CR^4$;
W is N or $CR^6$;
Y is N or $CR^7$;
$R^1$ is $C_{1-6}$ alkyl, $C_{1-6}$ haloalkyl, $C_{3-6}$ cycloalkyl, $C_{3-6}$ cycloalkyl-$C_{1-3}$ alkyl, 4-6 membered heterocycloalkyl, or 4-6 membered heterocycloalkyl-$C_{1-3}$ alkyl; wherein said $C_{1-6}$ alkyl, $C_{3-6}$ cycloalkyl, $C_{3-6}$ cycloalkyl-$C_{1-3}$ alkyl, 4-6 membered heterocycloalkyl, and 4-6 membered heterocycloalkyl-$C_{1-3}$ alkyl are each optionally substituted with 1, 2, or 3 substituents independently selected from fluoro, —OH, —O($C_{1-3}$ alkyl), —CN, —$CF_3$, $C_{1-3}$ alkyl, —$NH_2$, —NH($C_{1-3}$ alkyl), —N($C_{1-3}$ alkyl)$_2$, —C(O)N($C_{1-3}$ alkyl)$_2$, —C(O)NH($C_{1-3}$ alkyl), —C(O)$NH_2$, —C(O)O($C_{1-3}$ alkyl), —S(O)$_2$($C_{1-3}$ alkyl), —S(O)$_2$($C_{3-6}$ cycloalkyl), —C(O)($C_{3-6}$ cycloalkyl), and —C(O)($C_{1-3}$ alkyl);
$R^2$ is H or $C_{1-3}$ alkyl; wherein said $C_{1-3}$ alkyl is optionally substituted by 1, 2, or 3 substituents independently selected from fluoro, —OH, —O($C_{1-3}$ alkyl), —CN, —$CF_3$, $NH_2$, —NH($C_{1-3}$ alkyl), and —N($C_{1-3}$ alkyl)$_2$; or
$R^1$ and $R^2$ together with the nitrogen atom to which they are attached form a 4-, 5- or 6-membered heterocycloalkyl ring; which is optionally substituted with 1, 2, or 3 substitutents independently selected from fluoro, —OH, —O($C_{1-3}$ alkyl), —CN, $C_{1-3}$ alkyl, $C_{1-3}$ haloalkyl, —$NH_2$, —NH($C_{1-3}$ alkyl), —N($C_{1-3}$ alkyl)$_2$, and —$CH_2CN$;
$R^3$ is H, F, Cl, —CN, $C_{1-3}$ alkyl, —$OCF_3$, —$CF_3$, or —O($C_{1-3}$ alkyl);
$R^4$ is H, F, Cl, —CN, $C_{1-3}$ alkyl, or —O($C_{1-3}$ alkyl);
$R^5$ is H, F, Cl, —CN, $C_{1-3}$ alkyl, or —O($C_{1-3}$ alkyl);
$R^6$ is H, F, Cl, —CN, or $C_{1-3}$ alkyl; and
$R^7$ is H, F, Cl, —CN, $C_{1-3}$ alkyl, —$CH_2CN$, —C(O)N($C_{1-3}$ alkyl)$_2$, —C(O)NH($C_{1-3}$ alkyl), or —C(O)$NH_2$.

In some embodiments, Y is N.
In some embodiments, Y is $CR^7$.
In some embodiments, $R^7$ is H.
In some embodiments, X is N.
In some embodiments, X is $CR^4$.
In some embodiments, $R^4$ is H or F.
In some embodiments, W is N.
In some embodiments, W is $CR^6$.
In some embodiments, $R^6$ is H, F, or Cl.
In some embodiments, $R^5$ is H or F.
In some embodiments, $R^6$ is H or F.
In some embodiments, $R^6$ is H.
In some embodiments, $R^2$ is H or methyl.
In some embodiments, $R^2$ is H.
In some embodiments, $R^2$ is methyl.
In some embodiments, $R^1$ is $C_{1-6}$ alkyl, $C_{1-6}$ haloalkyl, $C_{3-6}$ cycloalkyl, $C_{3-6}$ cycloalkyl-$C_{1-3}$ alkyl, 5-6 membered heterocycloalkyl, or 5-6 membered heterocycloalkyl-$C_{1-3}$ alkyl, wherein said $C_{1-6}$ alkyl, $C_{3-6}$ cycloalkyl, $C_{3-6}$ cycloalkyl-$C_{1-3}$ alkyl, 5-6 membered heterocycloalkyl, and 5-6 membered heterocycloalkyl-$C_{1-3}$ alkyl are each optionally substituted with 1, 2, or 3 substituents independently selected from fluoro, —$CF_3$, and methyl.

In some embodiments, $R^1$ is isopropyl, ethyl, 1-methylpropyl, 2,2,2-trifluoro-1-methylethyl, 1-cyclopropylethyl, 1-cyclohexylethyl, cyclopropyl, 1-trifluoromethylcyclopropyl, 3,3-difluorocyclobutyl, 1-(1-methylpiperidin-4-yl)ethyl, 1-cyclopropyl-2,2,2-trifluoroethyl, 2,2,2-trifluoroethyl, or 2,2-difluoroethyl.

In some embodiments, $R^1$ is isopropyl, ethyl, 1-methylpropyl, 2,2,2-trifluoro-1-methylethyl, 1-cyclopropylethyl, 1-cyclohexylethyl, cyclopropyl, 1-trifluoromethylcyclopropyl, 3,3-difluorocyclobutyl, or 1-(1-methylpiperidin-4-yl)ethyl.

In some embodiments, $R^1$ is isopropyl.
In some embodiments, $R^1$ is ethyl.
In some embodiments, $R^1$ is 1-methylpropyl.
In some embodiments, $R^1$ is 2,2,2-trifluoro-1-methylethyl.

In some embodiments, R¹ is 1-trifluoromethylcyclopropyl.

In some embodiments, R¹ is 1-cyclopropyl-2,2,2-trifluoroethyl.

In some embodiments, R¹ is 2,2,2-trifluoroethyl.

In some embodiments, R¹ is 2,2-difluoroethyl.

In one embodiment (a):

X is N or CR⁴;
W is N or CR⁶;
Y is N or CR⁷;
R¹ is $C_{1-6}$ alkyl, $C_{1-6}$ haloalkyl, $C_{3-6}$ cycloalkyl, $C_{3-6}$ cycloalkyl-$C_{1-3}$ alkyl, 4-6 membered heterocycloalkyl, or 4-6 membered heterocycloalkyl-$C_{1-3}$ alkyl; wherein said $C_{1-6}$ alkyl, $C_{3-6}$ cycloalkyl, $C_{3-6}$ cycloalkyl-$C_{1-3}$ alkyl, 4-6 membered heterocycloalkyl, or 4-6 membered heterocycloalkyl-$C_{1-3}$ alkyl are each optionally substituted with 1, 2, or 3 substituents independently selected from fluoro, —OH, —O($C_{1-3}$ alkyl), —CN, —CF₃, $C_{1-3}$ alkyl, —NH₂, —NH($C_{1-3}$ alkyl), —N($C_{1-3}$ alkyl)₂, —C(O)N($C_{1-3}$ alkyl)₂, —C(O)NH($C_{1-3}$ alkyl), —C(O)NH₂, —C(O)O($C_{1-3}$ alkyl), —S(O)₂($C_{1-3}$ alkyl), —S(O)₂($C_{3-6}$ cycloalkyl), —C(O)($C_{3-6}$ cycloalkyl), and —C(O)($C_{1-3}$ alkyl);
R² is H or $C_{1-3}$ alkyl; wherein said $C_{1-3}$ alkyl is optionally substituted by 1, 2, or 3 substituents independently selected from fluoro, —OH, —O($C_{1-3}$ alkyl), —CN, —CF₃, NH₂, —NH($C_{1-3}$ alkyl), and —N($C_{1-3}$ alkyl)₂; or
R³ is H, F, Cl, —CN, $C_{1-3}$ alkyl, —OCF₃, —CF₃, or —O($C_{1-3}$ alkyl);
R⁴ is H, F, Cl, —CN, $C_{1-3}$ alkyl, or —O($C_{1-3}$ alkyl);
R⁵ is H, F, Cl, —CN, $C_{1-3}$ alkyl, or —O($C_{1-3}$ alkyl);
R⁶ is H, F, Cl, —CN, or $C_{1-3}$ alkyl; and
R⁷ is H, F, Cl, —CN, $C_{1-3}$ alkyl, or —CH₂CN.

In another embodiment (b):

X is N or CR⁴;
W is N or CR⁶;
Y is N or CR⁷;
R¹ is $C_{1-6}$ alkyl, $C_{1-6}$ haloalkyl, $C_{3-6}$ cycloalkyl, $C_{3-6}$ cycloalkyl-$C_{1-3}$ alkyl, 5-6 membered heterocycloalkyl, or 5-6 membered heterocycloalkyl-$C_{1-3}$ alkyl, wherein said $C_{1-6}$ alkyl, $C_{3-6}$ cycloalkyl, $C_{3-6}$ cycloalkyl-$C_{1-3}$ alkyl, 4-6 membered heterocycloalkyl, or 4-6 membered heterocycloalkyl-$C_{1-3}$ alkyl are each optionally substituted with 1, 2, or 3 substituents independently selected from fluoro, —OH, —O($C_{1-3}$ alkyl), —CN, —CF₃, $C_{1-3}$ alkyl, —NH₂, —NH($C_{1-3}$ alkyl), and —N($C_{1-3}$ alkyl)₂;
R² is H or methyl;
R³ is H, F, Cl, or methyl;
R⁴ is H, F, Cl, or methyl;
R⁵ is H, F, Cl, or methyl;
R⁶ is H, F, Cl, or methyl; and
R⁷ is H.

In another embodiment (c):

X is N or CR⁴;
W is N or CR⁶;
Y is N or CR⁷;
R¹ is $C_{1-6}$ alkyl, $C_{1-6}$ haloalkyl, $C_{3-6}$ cycloalkyl, $C_{3-6}$ cycloalkyl-$C_{1-3}$ alkyl, 5-6 membered heterocycloalkyl, or 5-6 membered heterocycloalkyl-$C_{1-3}$ alkyl, wherein said $C_{1-6}$ alkyl, $C_{3-6}$ cycloalkyl, $C_{3-6}$ cycloalkyl-$C_{1-3}$ alkyl, 4-6 membered heterocycloalkyl, or 4-6 membered heterocycloalkyl-$C_{1-3}$ alkyl are each optionally substituted with 1, 2, or 3 substituents independently selected from fluoro, —CF₃, and methyl;
R² is H or methyl;
R³ is H, F, or Cl;
R⁴ is H or F;
R⁵ is H or F;

R⁶ is H; and
R⁷ is H.

In some embodiments, the compound is a compound of Formula II:

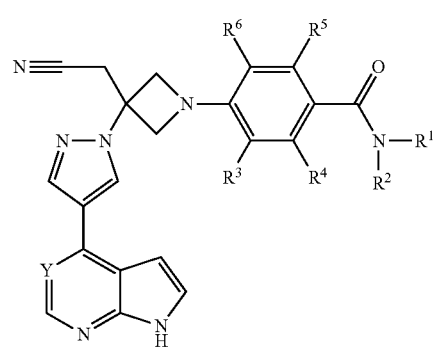

or a pharmaceutically acceptable salt thereof.

In some embodiments, the compound is a compound of Formula III:

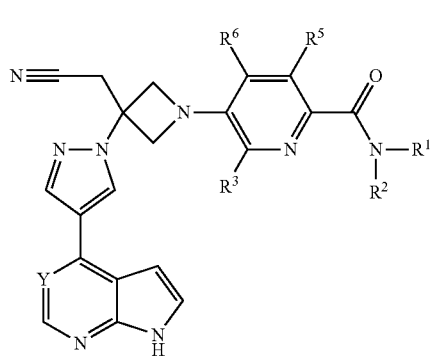

or a pharmaceutically acceptable salt thereof.

In some embodiments, the compound is a compound of Formula IV:

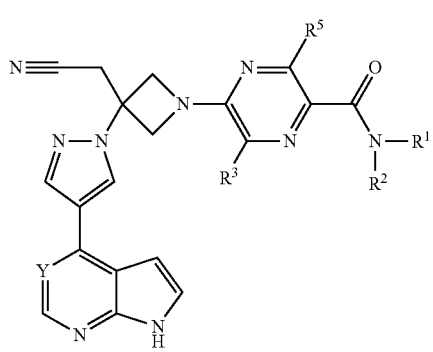

or a pharmaceutically acceptable salt thereof.

In some embodiments, the compound is a compound of Formula IIa:

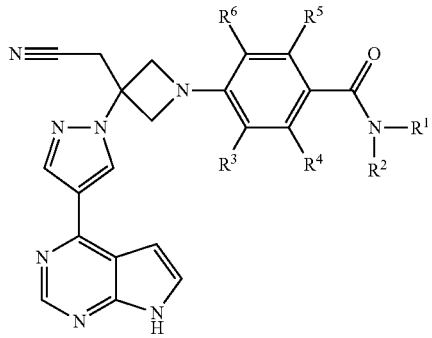

IIa or a pharmaceutically acceptable salt thereof.

In some embodiments, the compound is a compound of Formula IIb:

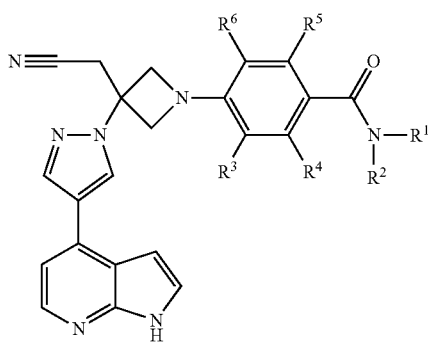

IIb or a pharmaceutically acceptable salt thereof.

In some embodiments, the compound is a compound of Formula IIIa:

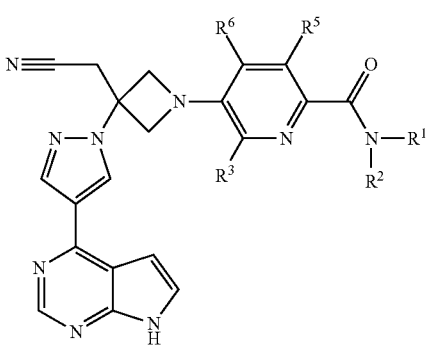

IIIa or a pharmaceutically acceptable salt thereof.

In some embodiments, the compound is a compound of Formula IIIb:

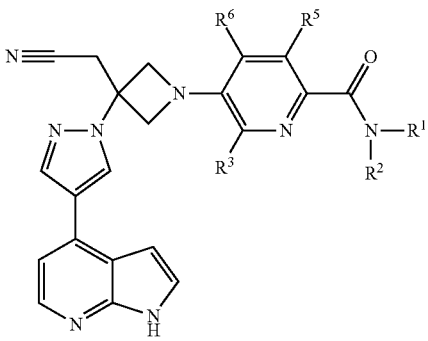

IIIb or a pharmaceutically acceptable salt thereof.

In some embodiments, the compound is a compound of Formula IVa:

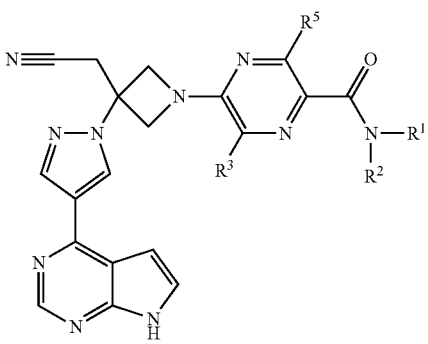

IVa or a pharmaceutically acceptable salt thereof.

In some embodiments, the compound is a compound of Formula IVb:

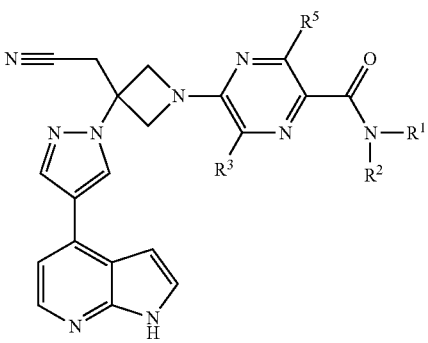

IVb or a pharmaceutically acceptable salt thereof.

In some embodiments, the compound has Formula II, wherein Y, $R^1$, $R^2$, $R^3$, $R^4$, $R^5$, $R^6$ are defined as in embodiment (a).

In some embodiments, the compound has Formula III, wherein Y, $R^1$, $R^2$, $R^3$, $R^5$, $R^6$ are defined as in embodiment (a).

In some embodiments, the compound has Formula IV, wherein Y, $R^1$, $R^2$, $R^3$, and $R^5$ are defined as in embodiment (a).

In some embodiments, the compound has Formula II, wherein Y, $R^1$, $R^2$, $R^3$, $R^4$, $R^5$, $R^6$ are defined as in embodiment (b).

In some embodiments, the compound has Formula III, wherein Y, $R^1$, $R^2$, $R^3$, $R^5$, $R^6$ are defined as in embodiment (b).

In some embodiments, the compound has Formula IV, wherein Y, $R^1$, $R^2$, $R^3$, and $R^5$ are defined as in embodiment (b).

In some embodiments, the compound has Formula II, wherein Y, $R^1$, $R^2$, $R^3$, $R^4$, $R^5$, $R^6$ are defined as in embodiment (c).

In some embodiments, the compound has Formula III, wherein Y, $R^1$, $R^2$, $R^3$, $R^5$, $R^6$ are defined as in embodiment (c).

In some embodiments, the compound has Formula IV, wherein Y, $R^1$, $R^2$, $R^3$, and $R^5$ are defined as in embodiment (c).

In some embodiments, the compound has Formula IIa, wherein $R^1$, $R^2$, $R^3$, $R^4$, $R^5$, $R^6$ are defined as in embodiment (a).

In some embodiments, the compound has Formula IIa, wherein $R^1$, $R^2$, $R^3$, $R^4$, $R^5$, $R^6$ are defined as in embodiment (b).

In some embodiments, the compound has Formula IIa, wherein $R^1$, $R^2$, $R^3$, $R^4$, $R^5$, $R^6$ are defined as in embodiment (c).

In some embodiments, the compound has Formula IIIa, wherein $R^1$, $R^2$, $R^3$, $R^5$, $R^6$ are defined as in embodiment (a).

In some embodiments, the compound has Formula IIIa, wherein $R^1$, $R^2$, $R^3$, $R^5$, $R^6$ are defined as in embodiment (b).

In some embodiments, the compound has Formula IIIa, wherein $R^1$, $R^2$, $R^3$, $R^5$, $R^6$ are defined as in embodiment (c).

In some embodiments, the compound has Formula IVa, wherein $R^1$, $R^2$, $R^3$, and $R^5$ are defined as in embodiment (a).

In some embodiments, the compound has Formula IVa, wherein $R^1$, $R^2$, $R^3$, and $R^5$ are defined as in embodiment (b).

In some embodiments, the compound has Formula IVa, wherein $R^1$, $R^2$, $R^3$, and $R^5$ are defined as in embodiment (c).

In some embodiments, the compound has Formula IIb, wherein $R^1$, $R^2$, $R^3$, $R^4$, $R^5$, $R^6$ are defined as in embodiment (a).

In some embodiments, the compound has Formula IIb, wherein $R^1$, $R^2$, $R^3$, $R^4$, $R^5$, $R^6$ are defined as in embodiment (b).

In some embodiments, the compound has Formula IIb, wherein $R^1$, $R^2$, $R^3$, $R^4$, $R^5$, $R^6$ are defined as in embodiment (c).

In some embodiments, the compound has Formula IIIb, wherein $R^1$, $R^2$, $R^3$, $R^5$, $R^6$ are defined as in embodiment (a).

In some embodiments, the compound has Formula IIIb, wherein $R^1$, $R^2$, $R^3$, $R^5$, $R^6$ are defined as in embodiment (b).

In some embodiments, the compound has Formula IIIb, wherein $R^1$, $R^2$, $R^3$, $R^5$, $R^6$ are defined as in embodiment (c).

In some embodiments, the compound has Formula IVa, wherein $R^1$, $R^2$, $R^3$, and $R^5$ are defined as in embodiment (a).

In some embodiments, the compound has Formula IVa, wherein $R^1$, $R^2$, $R^3$, and $R^5$ are defined as in embodiment (b).

In some embodiments, the compound has Formula IVa, wherein $R^1$, $R^2$, $R^3$, and $R^5$ are defined as in embodiment (c).

In some embodiments, the compound is selected from:

4-{3-(Cyanomethyl)-3-[4-(1H-pyrrolo[2,3-b]pyridin-4-yl)-1H-pyrazol-1-yl]azetidin-1-yl}-N-isopropylbenzamide;

5-{3-(Cyanomethyl)-3-[4-(1H-pyrrolo[2,3-b]pyridin-4-yl)-1H-pyrazol-1-yl]azetidin-1-yl}-N-[(1S)-1-cyclopropylethyl]pyridine-2-carboxamide;

4-{3-(Cyanomethyl)-3-[4-(7H-pyrrolo[2,3-d]pyrimidin-4-yl)-1H-pyrazol-1-yl]azetidin-1-yl}-3-fluoro-N-isopropylbenzamide;

4-{3-(Cyanomethyl)-3-[4-(7H-pyrrolo[2,3-d]pyrimidin-4-yl)-1H-pyrazol-1-yl]azetidin-1-yl}-N-[(1R)-1-cyclopropylethyl]-3-fluorobenzamide;

4-{3-(Cyanomethyl)-3-[4-(7H-pyrrolo[2,3-d]pyrimidin-4-yl)-1H-pyrazol-1-yl]azetidin-1-yl}-N-[(1S)-1-cyclopropylethyl]-3-fluorobenzamide;

4-{3-(Cyanomethyl)-3-[4-(7H-pyrrolo[2,3-d]pyrimidin-4-yl)-1H-pyrazol-1-yl]azetidin-1-yl}-2,5-difluoro-N-isopropylbenzamide;

4-{3-(Cyanomethyl)-3-[4-(7H-pyrrolo[2,3-d]pyrimidin-4-yl)-1H-pyrazol-1-yl]azetidin-1-yl}-N-cyclopropyl-3-fluoro-N-methylbenzamide;

5-Chloro-4-{3-(cyanomethyl)-3-[4-(7H-pyrrolo[2,3-d]pyrimidin-4-yl)-1H-pyrazol-1-yl]azetidin-1-yl}-2-fluoro-N-isopropylbenzamide;

5-{3-(Cyanomethyl)-3-[4-(7H-pyrrolo[2,3-d]pyrimidin-4-yl)-1H-pyrazol-1-yl]azetidin-1-yl}-N-isopropylpyridine-2-carboxamide;

4-{3-(Cyanomethyl)-3-[4-(7H-pyrrolo[2,3-d]pyrimidin-4-yl)-1H-pyrazol-1-yl]azetidin-1-yl}-3-fluoro-N-[(1S)-2,2,2-trifluoro-1-methylethyl]benzamide;

5-{3-(Cyanomethyl)-3-[4-(7H-pyrrolo[2,3-d]pyrimidin-4-yl)-1H-pyrazol-1-yl]azetidin-1-yl}-N-[(1S)-1-cyclopropylethyl]pyridine-2-carboxamide;

5-{3-(Cyanomethyl)-3-[4-(7H-pyrrolo[2,3-d]pyrimidin-4-yl)-1H-pyrazol-1-yl]azetidin-1-yl}-N-(3,3-difluorocyclobutyl)pyridine-2-carboxamide;

4-{3-(Cyanomethyl)-3-[4-(7H-pyrrolo[2,3-d]pyrimidin-4-yl)-1H-pyrazol-1-yl]azetidin-1-yl}-N-isopropylbenzamide;

4-{3-(Cyanomethyl)-3-[4-(7H-pyrrolo[2,3-d]pyrimidin-4-yl)-1H-pyrazol-1-yl]azetidin-1-yl}-2-fluoro-N-isopropylbenzamide;

4-{3-(Cyanomethyl)-3-[4-(7H-pyrrolo[2,3-d]pyrimidin-4-yl)-1H-pyrazol-1-yl]azetidin-1-yl}-N-[(1S)-1-cyclohexylethyl]-2-fluorobenzamide;

4-{3-(Cyanomethyl)-3-[4-(7H-pyrrolo[2,3-d]pyrimidin-4-yl)-1H-pyrazol-1-yl]azetidin-1-yl}-3-fluoro-N-[(1R)-2,2,2-trifluoro-1-methylethyl]benzamide;

5-{3-(Cyanomethyl)-3-[4-(7H-pyrrolo[2,3-d]pyrimidin-4-yl)-1H-pyrazol-1-yl]azetidin-1-yl}-N-[1-(trifluoromethyl)cyclopropyl]pyridine-2-carboxamide;

5-{3-(Cyanomethyl)-3-[4-(7H-pyrrolo[2,3-d]pyrimidin-4-yl)-1H-pyrazol-1-yl]azetidin-1-yl}-N-isopropylpyrazine-2-carboxamide;

4-{3-(Cyanomethyl)-3-[4-(7H-pyrrolo[2,3-d]pyrimidin-4-yl)-1H-pyrazol-1-yl]azetidin-1-yl}-N-[1-(1-methylpiperidin-4-yl)ethyl]benzamide;

4-{3-(Cyanomethyl)-3-[4-(7H-pyrrolo[2,3-d]pyrimidin-4-yl)-1H-pyrazol-1-yl]azetidin-1-yl}-N-[(1R)-1-cyclopropylethyl]-2,5-difluorobenzamide;

5-Chloro-4-{3-(cyanomethyl)-3-[4-(7H-pyrrolo[2,3-d]pyrimidin-4-yl)-1H-pyrazol-1-yl]azetidin-1-yl}-N-[(1R)-1-cyclopropylethyl]-2-fluorobenzamide;

4-{3-(Cyanomethyl)-3-[4-(7H-pyrrolo[2,3-d]pyrimidin-4-yl)-1H-pyrazol-1-yl]azetidin-1-yl}-2-fluoro-N-[(1S)-2,2,2-trifluoro-1-methylethyl]benzamide;

4-{3-(Cyanomethyl)-3-[4-(7H-pyrrolo[2,3-d]pyrimidin-4-yl)-1H-pyrazol-1-yl]azetidin-1-yl}-N-[(1R)-2,2,2-trifluoro-1-methylethyl]benzamide;

5-{3-(Cyanomethyl)-3-[4-(7H-pyrrolo[2,3-d]pyrimidin-4-yl)-1H-pyrazol-1-yl]azetidin-1-yl}-N-ethylpyridine-2-carboxamide;

4-{3-(Cyanomethyl)-3-[4-(7H-pyrrolo[2,3-d]pyrimidin-4-yl)-1H-pyrazol-1-yl]azetidin-1-yl}-N-[(1R)-1-methylpropyl]benzamide; and 4-{3-(Cyanomethyl)-3-[4-(7H-pyrrolo[2,3-d]pyrimidin-4-yl)-1H-pyrazol-1-yl]azetidin-1-yl}-N-(2,2,2-trifluoro-1-methylethyl)benzamide;

or a pharmaceutically acceptable salt thereof.

In some embodiments, the compound is selected from:

4-{3-(Cyanomethyl)-3-[4-(1H-pyrrolo[2,3-b]pyridin-4-yl)-1H-pyrazol-1-yl]azetidin-1-yl}-3-fluoro-N-isopropylbenzamide;

4-{3-(Cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide;

4-{3-(Cyanomethyl)-3-[4-(7H-pyrrolo[2,3-d]pyrimidin-4-yl)-1H-pyrazol-1-yl]azetidin-1-yl}-2,5-difluoro-N-[(1R)-2,2,2-trifluoro-1-methylethyl]benzamide;

5-{3-(Cyanomethyl)-3-[4-(7H-pyrrolo[2,3-d]pyrimidin-4-yl)-1H-pyrazol-1-yl]azetidin-1-yl}-N-[(1R)-2,2,2-trifluoro-1-methylethyl]pyrazine-2-carboxamide;

5-{3-(Cyanomethyl)-3-[4-(7H-pyrrolo[2,3-d]pyrimidin-4-yl)-1H-pyrazol-1-yl]azetidin-1-yl}-N-[(1S)-2,2,2-trifluoro-1-methylethyl]pyrazine-2-carboxamide;

5-{3-(Cyanomethyl)-3-[4-(7H-pyrrolo[2,3-d]pyrimidin-4-yl)-1H-pyrazol-1-yl]azetidin-1-yl}-N-[(1S)-1-cyclopropyl-2,2,2-trifluoroethyl]pyrazine-2-carboxamide;

5-{3-(Cyanomethyl)-3-[4-(7H-pyrrolo[2,3-d]pyrimidin-4-yl)-1H-pyrazol-1-yl]azetidin-1-yl}-N-[1-(trifluoromethyl)cyclopropyl]pyrazine-2-carboxamide;

5-{3-(Cyanomethyl)-3-[4-(1H-pyrrolo[2,3-b]pyridin-4-yl)-1H-pyrazol-1-yl]azetidin-1-yl}-N-isopropylpyrazine-2-carboxamide;

5-{3-(Cyanomethyl)-3-[4-(1H-pyrrolo[2,3-b]pyridin-4-yl)-1H-pyrazol-1-yl]azetidin-1-yl}-N-[(1S)-2,2,2-trifluoro-1-methylethyl]pyrazine-2-carboxamide;

5-{3-(Cyanomethyl)-3-[4-(1H-pyrrolo[2,3-b]pyridin-4-yl)-1H-pyrazol-1-yl]azetidin-1-yl}-N-(2,2,2-trifluoroethyl)pyrazine-2-carboxamide;

4-{3-(Cyanomethyl)-3-[4-(7H-pyrrolo[2,3-d]pyrimidin-4-yl)-1H-pyrazol-1-yl]azetidin-1-yl}-N-(2,2-difluoroethyl)-2,5-difluorobenzamide;

4-{3-(Cyanomethyl)-3-[4-(7H-pyrrolo[2,3-d]pyrimidin-4-yl)-1H-pyrazol-1-yl]azetidin-1-yl}-N-[(1S)-1-cyclopropyl-2,2,2-trifluoroethyl]benzamide;

4-{3-(Cyanomethyl)-3-[4-(7H-pyrrolo[2,3-d]pyrimidin-4-yl)-1H-pyrazol-1-yl]azetidin-1-yl}-N-[(1R)-1-cyclopropylethyl]-2-fluorobenzamide;

5-{3-(Cyanomethyl)-3-[4-(1H-pyrrolo[2,3-b]pyridin-4-yl)-1H-pyrazol-1-yl]azetidin-1-yl}-N-[1-(trifluoromethyl)cyclopropyl]pyridine-2-carboxamide;

5-{3-(Cyanomethyl)-3-[4-(1H-pyrrolo[2,3-b]pyridin-4-yl)-1H-pyrazol-1-yl]azetidin-1-yl}-N-[(1S)-1-cyclopropylethyl]pyrazine-2-carboxamide;

5-{3-(Cyanomethyl)-3-[4-(1H-pyrrolo[2,3-b]pyridin-4-yl)-1H-pyrazol-1-yl]azetidin-1-yl}-N-[(1S)-1-cyclopropyl-2,2,2-trifluoroethyl]pyrazine-2-carboxamide; or a pharmaceutically acceptable salt thereof.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

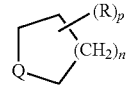

then it is to be understood that substituent R can occur p number of times on the ring, and R can be a different moiety at each occurrence. It is to be understood that each R group may replace any hydrogen atom attached to a ring atom, including one or both of the $(CH_2)_n$ hydrogen atoms. Further, in the above example, should the variable Q be defined to include hydrogens, such as when Q is said to be $CH_2$, NH, etc., any floating substituent such as R in the above example, can replace a hydrogen of the Q variable as well as a hydrogen in any other non-variable component of the ring.

As used herein, the phrase "optionally substituted" means unsubstituted or substituted. As used herein, the term "substituted" means that a hydrogen atom is removed and replaced by a substituent. It is to be understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 6, 1 to 4 or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like.

As used herein, "halo" or "halogen", employed alone or in combination with other terms, includes fluoro, chloro, bromo, and iodo.

As used herein, the term "$C_{n-m}$ haloalkyl", employed alone or in combination with other terms, refers to an $C_{n-m}$ alkyl group having up to {2(n to m)+1} halogen atoms which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like. In some embodiments, the haloalkyl group is a fluoroalkyl group.

As used herein, the term "$C_{n-m}$ cycloalkyl", employed alone or in combination with other terms, refers to a non-aromatic cyclic hydrocarbon including cyclized alkyl and alkenyl groups, and which has n to m ring member carbon atoms. Cycloalkyl groups can include mono- or bicyclic (e.g., having two fused or bridged rings) ring systems. One or more ring-forming carbon atoms of a cycloalkyl group can be optionally substituted by oxo. Cycloalkyl groups also include cycloalkylidenes. In some embodiments, the cycloalkyl group has 3, 4, 5, or 6 ring members. In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Example cycloalkyl groups include cyclopropyl, cyclobutyl, cyclopentyl, cyclohexyl, cyclopentenyl, cyclohexenyl, cyclohexadienyl, norbornyl, norpinyl, bicyclo[2.1.1]hexanyl, bicyclo[1.1.1]pentanyl, and the like.

As used herein, the term "$C_{n-m}$ cycloalkyl-$C_{o-p}$ alkyl", employed alone or in combination with other terms, refers to a group of formula -alkylene-cycloalkyl, wherein the cycloalkyl portion has n to m carbon atoms and the alkylene portion has o to p carbon atoms. In some embodiments, the alkylene portion has 1 to 3, 1 to 2, or 1 carbon atom(s). In some embodiments, the alkylene portion is methylene or ethylene. In some embodiments, the alkylene portion is methylene. In some embodiments, the cycloalkyl portion has 3 to 6 ring members, 3 to 5 ring members, 3 to 4 ring members, or 3 ring members. In some embodiments, the cycloalkyl group is monocyclic or bicyclic. In some embodiments, the cycloalkyl portion is monocyclic. In some embodiments, the cycloalkyl portion is a $C_{3-6}$ monocyclic cycloalkyl group.

As used herein, the term "4-6 membered heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur oxygen and phosphorus, and which has 4, 5, or 6 ring members. Heterocycloalkyl groups can include mono- or bicyclic (e.g., having two fused or bridged rings) ring systems. In some embodiments, the heterocycloalkyl group is a monocyclic group having 1, 2, or 3 heteroatoms independently selected from nitrogen, sulfur and oxygen. In some embodiments, the heterocycloalkyl group is a 4- to 6-membered ring, a 5- to 6-membered ring, a 6-membered ring, a 5-membered ring, or a 4-membered ring. One or more carbon atoms or hetereoatoms in the ring(s) of the heterocycloalkyl group can be oxidized to form a carbonyl, an N-oxide, or a sulfonyl group (or other oxidized linkage), or a nitrogen atom can be quaternized. Examples of heterocycloalkyl groups include azetidine, pyrrolidine, piperidine, piperazine, morpholine, thiomorpholine, and pyran. In some embodiments, the 4-6 membered heterocycloalkyl is azetidine, pyrrolidine, or piperidine.

As used herein, the term "4-6 membered heterocycloalkyl-$C_{n-m}$ alkyl", employed alone or in combination with other terms, refers to a group of formula -alkylene-heterocycloalkyl, wherein the heterocycloalkyl portion has 4, 5, or 6 ring members and the alkylene portion has n to m carbon atoms. In some embodiments, the alkylene portion has 1 to 3, 1 to 2, or 1 carbon atom(s). In some embodiments, the alkylene portion is methylene. In some embodiments, the heterocycloalkyl portion has 4 to 6 ring members, 5 to 6 ring members, or 5 ring members. In some embodiments, the heterocycloalkyl group is monocyclic or bicyclic. In some embodiments, the heterocycloalkyl portion is monocyclic. In some embodiments, the heterocycloalkyl portion is a 4-6 membered monocyclic heterocycloalkyl group.

As used herein, the appearance of the term "bicyclic" before the name of a moiety indicates that the moiety has two fused rings.

As used herein, the appearance of the term "monocyclic" before the name of a moiety indicates that the moiety has a single ring.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art. Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. In some embodiments, 1, 2, or 3 $CH_2$ groups in the azetidine ring of Formula I are replaced by a CHD or CD$_2$ group. In some embodiments, 1, 2, or 3 CH$_2$ or CH groups in the piperidine ring of Formula I are replaced by a CHD, CD$_2$ or CD group, respectively. In some embodiments, 1, 2, 3, 4, or 5 CH$_2$ or CH groups in the piperidine ring of Formula I are replaced by a CHD, CD$_2$ or CD group, respectively.

The term, "compound," as used herein is meant to include all stereoisomers, geometric iosomers, tautomers, and isotopes of the structures depicted.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. In some embodiments, the compounds described herein include the N-oxide forms.

Synthesis

Compounds of the invention, including salts and N-oxides thereof, can be prepared using known organic synthesis techniques and can be synthesized according to any of numerous possible synthetic routes, such as those in the Schemes below. The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2007), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

A series of arylamide derivatives 13 (Y can be N, CH or CR$^7$; W can be N or CR$^6$, and X can be N or CR$^4$) can be prepared according to the procedure outlined in Scheme 1. Protected bicyclo-hetero compound 2 can be achieved by reaction of the corresponding bicyclo-hetero compound 1 with (2-(chloromethoxy)ethyl)trimethylsilane (SEMCl) in the presence of the suitable base such as NaH in DMF. Suzuki coupling of the bicyclo-hetero compound 2 with suitable boronic acid 3 produces the corresponding compound 4. The protecting group (PG) in compound 4 can be removed to give the compound 5 by hydrogenation in the presence of palladium on carbon in the case of PG=Cbz or in the case of PG=Boc by treatment with acid such as, but not limited to, trifluoroacetic acid (TFA) or HCl in a suitable solvent such as, but not limited to, dichloromethane (DCM), methanol, dioxane, or combination of two solvents, or with base such as sodium carbonate or potassium carbonate in hot methanol. Michael addition of 5 with α,β-unsaturated nitrile 6 can afford the adduct 7. Removal of the Boc group in 7 yields the amine derivative 8 which can be converted to the corresponding aryl ester 10 by reaction with halo-substituted arylacid ester 9 in the presence of the suitable catalyst such as, but not limited to, BINAP [2,2'-bis(diphenylphosphino)-1,1'binaphthalene], Tol-BINAP [2,2'-bis(di-p-tolylphosphino)-1,1'binaphthalene], Xanthpos [4,5-bis(diphenylphosphino)-9,9-dimethylxanthene]. The aryl ester 10 can be hydrolyzed to the corresponding acid 11 by using an alkali such as lithium hydroxide, sodium hydroxide or potassium hydroxide. Coupling of the acid 11 with an appropriate amine can yield an arylamide 12 by using a coupling reagent such as but not limited to, BOP, PyOP, HATU, HBTU, EDC, or CDI. Removal of the protecting group SEM in 12 to afford the arylamide derivative 13 can be achieved by treatment with an acid such as BF$_3$, or TFA, and following by treatment with an amine such as ethylenediamine or ammonia.

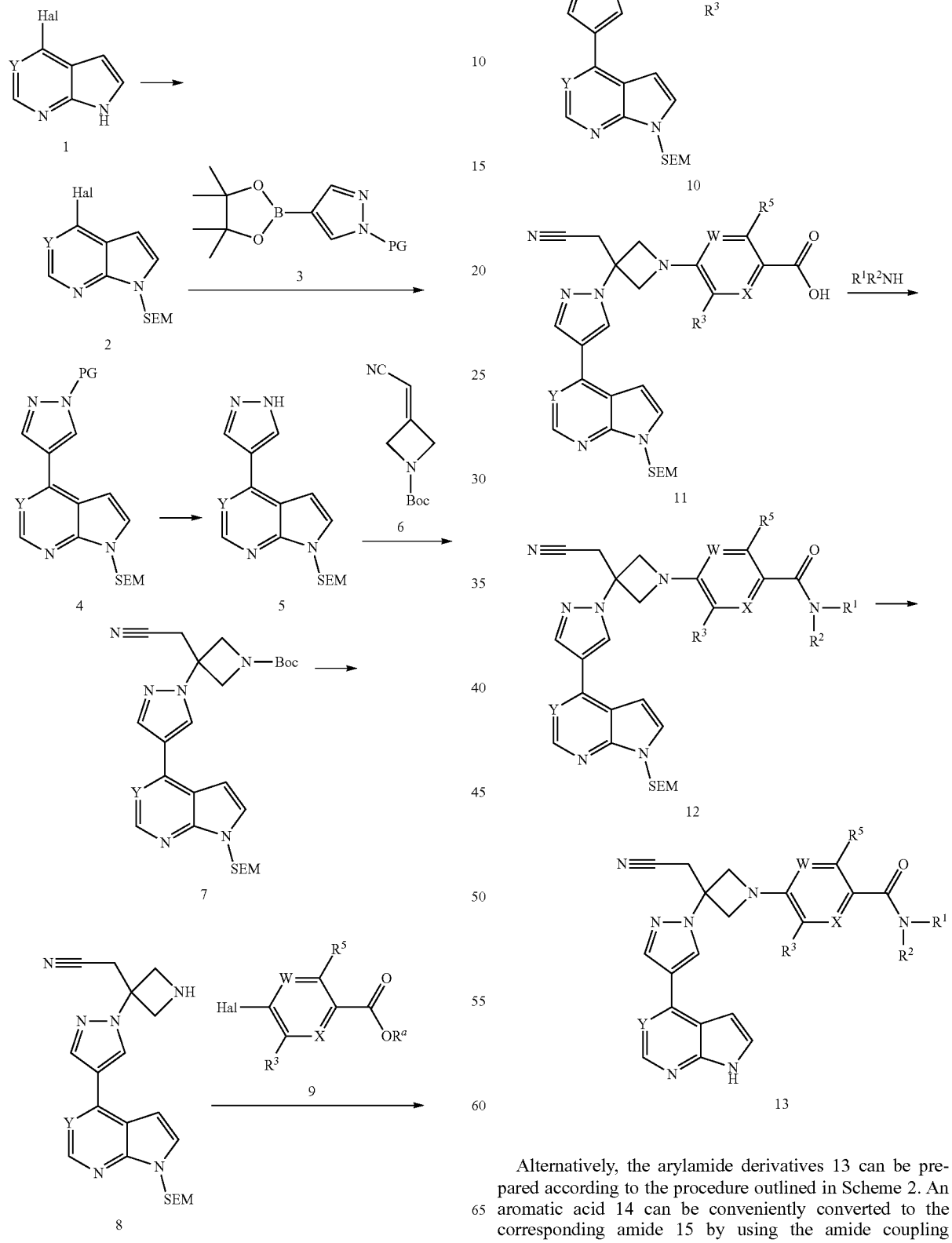

Alternatively, the arylamide derivatives 13 can be prepared according to the procedure outlined in Scheme 2. An aromatic acid 14 can be conveniently converted to the corresponding amide 15 by using the amide coupling reagent such as BOP, PyOP, HATU, HBTU, EDC, or CDI.

Aromatic amination of 8 with the amide 15 to produce 12 can be archived similar to those described above in the presence of the suitable catalyst such as, but not limited to, BINAP [2,2'-bis(diphenylphosphino)-1,1'-binaphthalene], Tol-BINAP [2,2'-bis(di-p-tolylphosphino)-1,1'binaphthalene], Xantphos [4,5-bis(diphenylphosphino)-9,9-dimethylxanthene]. Removal of the protecting group SEM in 12 can afford the arylamide 13 as described above.

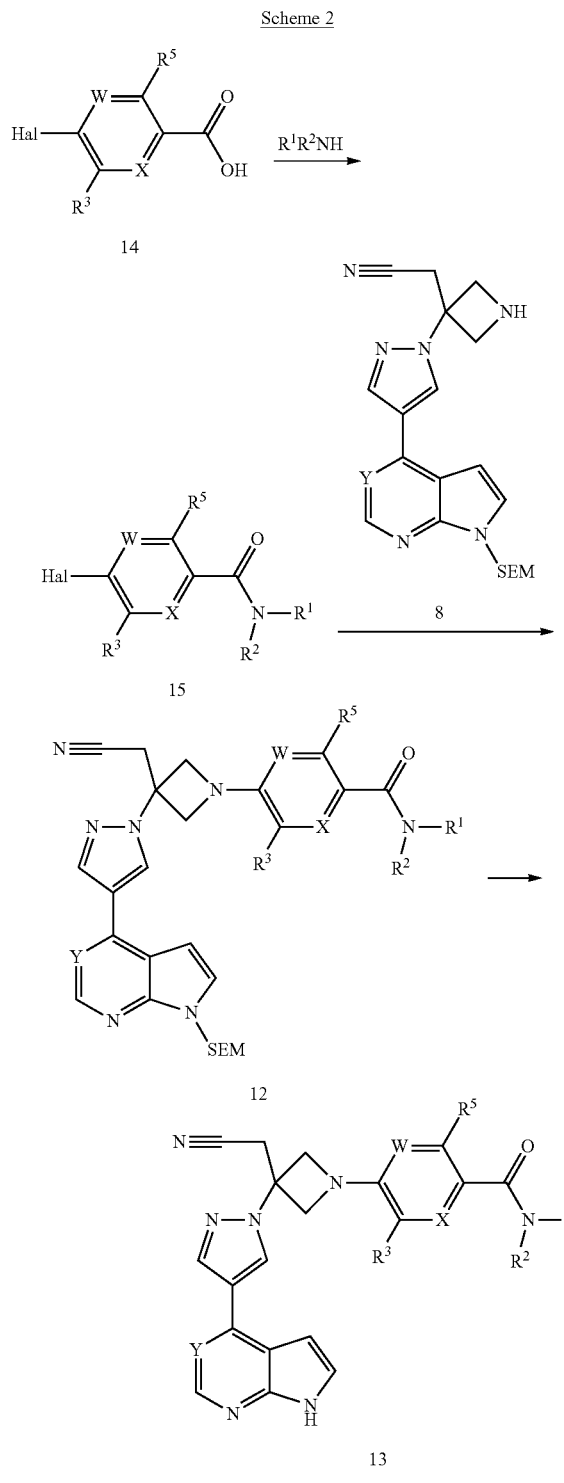

A series of aryl ester derivatives 10 can be prepared according to the methods outlined in Scheme 3. Replacement of the leaving group Hal (Hal can be halogen, OTs or OTf) in 9 by 3-hydroazetidine to produce compound 16 can be achieved under thermal conditions in a suitable solvent such as, but not limited to, DMSO, dioxane, DMF, or NMP in the presence of a base such as potassium carbonate, cesium carbonate, or sodium carbonate; or under copper-catalyzed Ullmann type N-arylation reaction conditions by using copper(I) iodide and potassium carbonate; or under palladium-catalyzed C—N bond forming reaction conditions using Xantphos [4,5-bis(diphenylphosphino)-9,9-dimetnylxanthene], BINAP [2,2'-bis(diphenylphosphino)-1,1'-binaphthyl], or P(o-Tol)3 [tri(o-tolyl)phosphine] as the ligand and potassium carbonate or cesium carbonate or potassium tert-butoxide as the base. α,β-Unsaturated nitrile 18 can be obtained by Wittig's reaction of diethyl cyanomethylphosphonate with the ketone 17 which can be given by Swern oxidation of 16. Michael addition of 5 with α,β-unsaturated nitrile 18 can afford the adduct 10.

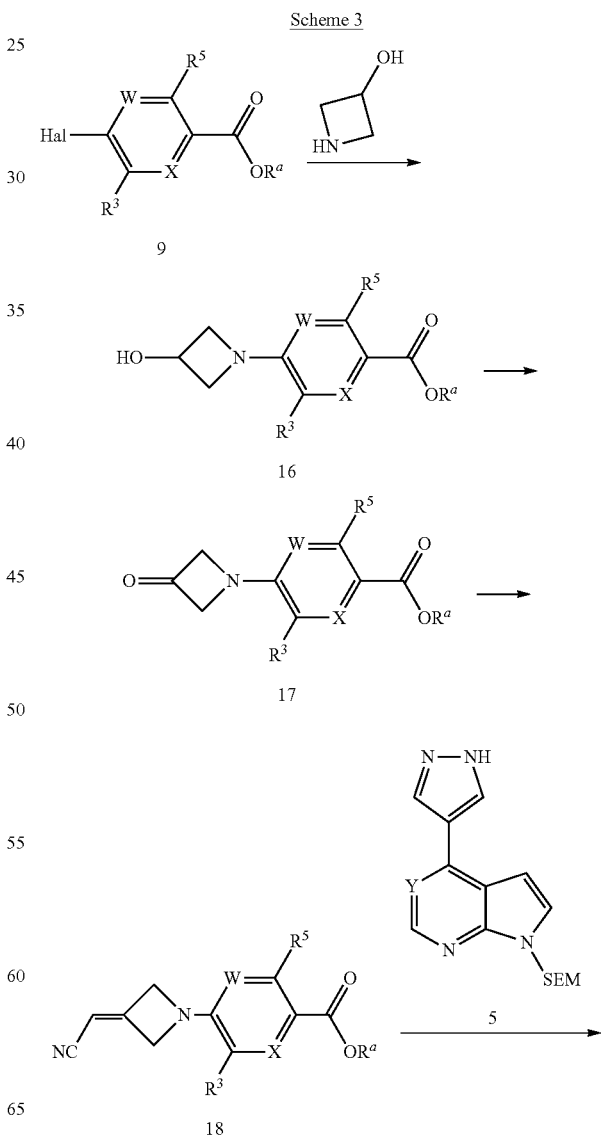

21

-continued

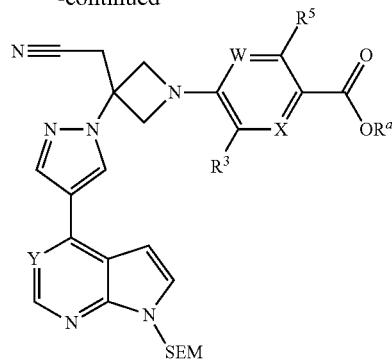

10

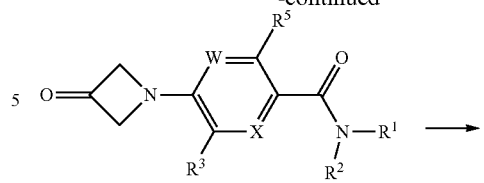

22

-continued

21

22

12

Similarly, a series of aryl amide derivatives 12 can be prepared according to the procedures outlined in Scheme 4. The aryl ester 16 can be hydrolyzed to the corresponding acid 19 by using an alkali such as lithium hydroxide, sodium hydroxide or potassium hydroxide. The acid 19 can be transferred to the arylamide 20 by reaction with an appropriate amine in the presence of a suitable coupling reagent such as, but not limited to, BOP, PyOP, HATU, HBTU, EDC, or CDI. Swern oxidation of 20 can produce the corresponding ketone 21 which can be converted to the α,β-unsaturated nitrile 22 by Wittig's reaction with diethyl cyanomethylphosphonate. Michael addition of 5 with α,β-unsaturated nitrile 21 can afford the adduct 12.

Scheme 4

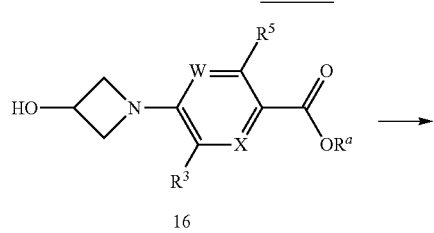

16

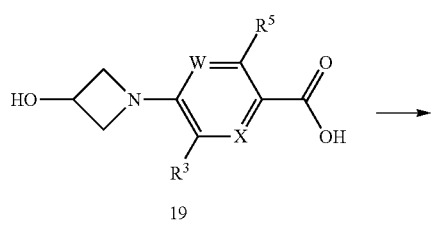

19

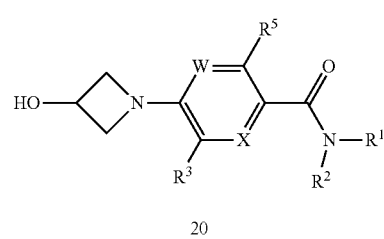

20

Methods

Compounds of the invention are JAK inhibitors, and the majority of the compounds of the invention, are JAK1 selective inhibitors. A JAK1 selective inhibitor is a compound that inhibits JAK1 activity preferentially over other Janus kinases. For example, the compounds of the invention preferentially inhibit JAK1 over one or more of JAK2, JAK3, and TYK2. In some embodiments, the compounds inhibit JAK1 preferentially over JAK2 (e.g., have a JAK1/JAK2 IC$_{50}$ ratio >1) as calculated by measuring IC$_{50}$ at 1 mM ATP (e.g., see Example A). In some embodiments, the compounds are greater than about 10-fold more selective for JAK1 over JAK2, as calculated by measuring IC$_{50}$ at 1 mM ATP. In some embodiments, the compounds are greater than about 15-fold selective for JAK1 over JAK2, as calculated by measuring IC$_{50}$ at 1 mM ATP. In some embodiments, the compounds are greater than about 20-fold selective for JAK1 over JAK2, as calculated by measuring IC$_{50}$ at 1 mM ATP.

JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, J. E. et al., Autoimmunity Reviews, 8:538-42, 2009). Because IL-6 signals, at least in part, through JAK1, antagonizing IL-6 directly or indirectly through JAK1 inhibition is expected to provide clinical benefit (Guschin, D., N., et al Embo J 14:1421, 1995; Smolen, J. S., et al. Lancet 371:987, 2008). Moreover, in some cancers JAK1 is mutated resulting in constitutive undesirable tumor cell growth and survival (Mullighan C G, Proc Natl Acad Sci USA. 106: 9414-8, 2009; Flex E., et al. J Exp Med. 205:751-8, 2008). In other autoimmune diseases and cancers elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Selective inhibitors of JAK1, relative to other JAK kinases, may have multiple therapeutic advantages over less selective inhibitors. With respect to selectivity against JAK2, a number of important cytokines and growth factors signal through JAK2 including, for example, erythropoietin (Epo) and thrombopoietin (Tpo) (Parganas E, et al. Cell. 93:385-95, 1998). Epo is a key growth factor for red blood cells production; hence a paucity of Epo-dependent signaling can result in reduced numbers of red blood cells and anemia (Kaushansky K, NEJM 354:2034-45, 2006). Tpo, another example of a JAK2-dependent growth factor, plays a central role in controlling the proliferation and maturation of megakaryocytes—the cells from which platelets are produced (Kaushansky K, NEJM 354:2034-45, 2006). As such, reduced Tpo signaling would decrease megakaryocyte numbers (megakaryocytopenia) and lower circulating platelet counts (thrombocytopenia). This can result in undesirable and/or uncontrollable bleeding. Reduced inhibition of other JAKs, such as JAK3 and Tyk2, may also be desirable as humans lacking functional version of these kinases have been shown to suffer from numerous maladies such as severe-combined immunodeficiency or hyperimmunoglobulin E syndrome (Minegishi, Y, et al. Immunity 25:745-55, 2006; Macchi P, et al. Nature. 377:65-8, 1995). Therefore a JAK1 inhibitor with reduced affinity for other JAKs would have significant advantages over a less-selective inhibitor with respect to reduced side effects involving immune suppression, anemia and thrombocytopenia.

Another aspect of the present invention pertains to methods of treating a JAK-associated disease or disorder in an individual (e.g., patient) by administering to the individual in need of such treatment a therapeutically effective amount or dose of a compound of the present invention or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, chronic obstructive pulmonary disease (COPD), and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, eszematous dermatitis, contact dermatitis, atopic dermatitis (atropic eczema), and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated disease include diseases associated with cartilage turnover, for example, gouty arthritis, septic or infectious arthritis, reactive arthritis, reflex sympathetic dystrophy, algodystrophy, Tietze syndrome, costal athropathy, osteoarthritis deformans endemica, Mseleni disease, Handigodu disease, degeneration resulting from fibromyalgia, systemic lupus erythematosus, scleroderma, or ankylosing spondylitis.

Further examples of JAK-associated disease include congenital cartilage malformations, including hereditary chondrolysis, chondrodysplasias, and pseudochrondrodysplasias (e.g., microtia, enotia, and metaphyseal chrondrodysplasia).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, uterine leiomyosarcoma, melanoma etc.), hematological cancers (e.g., lymphoma, leukemia such as acute lymphoblastic leukemia (ALL), acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides.

In some embodiments, the JAK inhibitors described herein, or in combination with other JAK inhibitors, such as those reported in U.S. Ser. No. 11/637,545, which is incorporated herein by reference in its entirety, can be used to treat inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

JAK-associated diseases can further include those characterized by expression of: JAK2 mutants such as those having at least one mutation in the pseudo-kinase domain (e.g., JAK2V617F); JAK2 mutants having at least one mutation outside of the pseudo-kinase domain; JAK1 mutants; JAK3 mutants; erythropoietin receptor (EPOR) mutants; or deregulated expression of CRLF2.

JAK-associated diseases can further include myeloproliferative disorders (MPDs) such as polycythemia vera (PV), essential thrombocythemia (ET), primary myelofibrosis (PMF), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is myelofibrosis (e.g., primary myelofibrosis (PMF), post polycythemia vera myelofibrosis (Post-PV MF) or post-essential thrombocythemia myelofibrosis (Post-ET MF)). In some embodiments, the myeloproliferative disorder is myelofibrosis with myeloid metaplasia (MMM). In some embodiments, the myeloproliferative disorder is post-essential thrombocythemia myelofibrosis (Post-ET MF). In some embodiments, the myeloproliferative disorder is post polycythemia vera myelofibrosis (Post-PV MF).

The present invention further provides methods of treating psoriasis or other skin disorders by administration of a topical formulation containing a compound of the invention.

In some embodiments, JAK inhibitors described herein can be used to treat pulmonary arterial hypertension.

The present invention further provides a method of treating dermatological side effects of other pharmaceuticals by administration of the compound of the invention. For example, numerous pharmaceutical agents result in unwanted allergic reactions which can manifest as acneiform rash or related dermatitis. Example pharmaceutical agents that have such undesirable side effects include anti-cancer drugs such as gefitinib, cetuximab, erlotinib, and the like. The compounds of the invention can be administered systemically or topically (e.g., localized to the vicinity of the dermatitis) in combination with (e.g., simultaneously or sequentially) the pharmaceutical agent having the undesirable dermatological side effect. In some embodiments, the compound of the invention can be administered topically together with one or more other pharmaceuticals, where the other pharmaceuticals when topically applied in the absence of a compound of the invention cause contact dermatitis, allergic contact sensitization, or similar skin disorder. Accordingly, compositions of the invention include topical formulations containing the compound of the invention and a further pharmaceutical agent which can cause dermatitis, skin disorders, or related side effects.

Further JAK-associated diseases include inflammation and inflammatory diseases. Example inflammatory diseases include sarcoidosis, inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases. In some embodiments, the inflammation disease of the eye is blepharitis.

The JAK inhibitors described herein can further be used to treat ischemia reperfusion injuries or a disease or condition related to an inflammatory ischemic event such as stroke or cardiac arrest. The JAK inhibitors described herein can further be used to treat endotoxin-driven disease state (e.g., complications after bypass surgery or chronic endotoxin states contributing to chronic cardiac failure). The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J Biol. Chem.* 2004, 279(19): 19936-47. Epub 2004 Mar. 2, both of which are incorporated herein by reference in their entirety. The JAK inhibitors described herein can be used to treat Alzheimer's disease.

The JAK inhibitors described herein can further be used to treat other inflammatory diseases such as systemic inflammatory response syndrome (SIRS) and septic shock.

The JAK inhibitors described herein can further be used to treat gout and increased prostate size due to, e.g., benign prostatic hypertrophy or benign prostatic hyperplasia.

Further JAK-associated diseases include bone resorption diseases such as osteoporosis, osteoarthritis. Bone resorption can also be associated with other conditions such as hormonal imbalance and/or hormonal therapy, autoimmune disease (e.g. osseous sarcoidosis), or cancer (e.g. myeloma). The reduction of the bone resorption due to the JAK inhibitors can be about 10%, about 20%, about 30%, about 40%, about 50%, about 60%, about 70%, about 80%, or about 90%.

In some embodiments, JAK inhibitors described herein can further be used to treat a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", *The Ocular Surface,* 5(2), 75-92 April 2007, which is incorporated herein by reference in its entirety. In some embodiments, the dry eye disorder is selected from aqueous tear-deficient dry eye (ADDE) or evaporative dry eye disorder, or appropriate combinations thereof. In some embodiments, the dry eye disorder is Sjogren syndrome dry eye (SSDE). In some embodiments, the dry eye disorder is non-Sjogren syndrome dry eye (NSSDE).

In a further aspect, the present invention provides a method of treating conjunctivitis, uveitis (including chronic uveitis), chorioditis, retinitis, cyclitis, sclieritis, episcleritis, or iritis; treating inflammation or pain related to corneal transplant, LASIK (laser assisted in situ keratomileusis), photorefractive keratectomy, or LASEK (laser assisted sub-epithelial keratomileusis); inhibiting loss of visual acuity related to corneal transplant, LASIK, photorefractive keratectomy, or LASEK; or inhibiting transplant rejection in a patient in need thereof, comprising administering to the patient a therapeutically effective amount of the compound of the invention, or a pharmaceutically acceptable salt thereof.

Additionally, the compounds of the invention, or in combination with other JAK inhibitors, such as those reported in U.S. Ser. No. 11/637,545, which is incorporated herein by reference in its entirety, can be used to treat respiratory dysfunction or failure associated with viral infection, such as influenza and SARS.

In some embodiments, the present invention provides a compound as described in any of the embodiments herein, or a pharmaceutically acceptable salt thereof, for use in a method of treating any of the diseases or disorders described herein. In some embodiments, the present invention provides the use of a compound as described in any of the embodiments herein, or a pharmaceutically acceptable salt thereof, for the preparation of a medicament for use in a method of treating any of the diseases or disorders described herein.

In some embodiments, the present invention provides a compound as described in any of the embodiments herein, or a pharmaceutically acceptable salt thereof, for use in a method of modulating JAK1. In some embodiments, the present invention also provides use of a compound as described in any of the embodiments herein, or a pharmaceutically acceptable salt thereof, for the preparation of a medicament for use in a method of modulating JAK1.

As used herein, the term "contacting" refers to the bringing together of indicated moieties in an in vitro system or an in vivo system. For example, "contacting" a JAK with a compound of the invention includes the administration of a compound of the present invention to an individual or patient, such as a human, having a JAK, as well as, for example, introducing a compound of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the therapeutically effective amount is about 5 mg to about 1000 mg, or about 10 mg to about 500 mg.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing the disease; for example, preventing a disease, condition or disorder in an individual who may be predisposed to the disease, condition or disorder but does not yet experience or display the pathology or symptomatology of the disease.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, which is incorporated herein by reference in its entirety, or other agents can be used in combination with the compounds described herein for treatment of JAK-associated diseases, disorders or conditions. The one or more additional pharmaceutical agents can be administered to a patient simultaneously or sequentially.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone. Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491, all of which are incorporated herein by reference in their entirety.

Example suitable Flt-3 inhibitors include compounds, and their pharmaceutically acceptable salts, as disclosed in WO 03/037347, WO 03/099771, and WO 04/046120, all of which are incorporated herein by reference in their entirety.

Example suitable RAF inhibitors include compounds, and their pharmaceutically acceptable salts, as disclosed in WO 00/09495 and WO 05/028444, both of which are incorporated herein by reference in their entirety.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402, all of which are incorporated herein by reference in their entirety.

In some embodiments, one or more of the compounds of the invention can be used in combination with one or more other kinase inhibitors including imatinib, particularly for treating patients resistant to imatinib or other kinase inhibitors.

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

In some embodiments, the additional therapeutic agent is fluocinolone acetonide (Retisert®), or rimexolone (AL-2178, Vexol, Alcon).

In some embodiments, the additional therapeutic agent is cyclosporine (Restasis®).

In some embodiments, the additional therapeutic agent is a corticosteroid. In some embodiments, the corticosteroid is triamcinolone, dexamethasone, fluocinolone, cortisone, prednisolone, or flumetholone.

In some embodiments, the additional therapeutic agent is selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), actemra, gemcitabine, oxaliplatin, L-asparaginase, or thalidomide.

In some embodiments, the additional therapeutic agent is an anti-angiogenic agent, cholinergic agonist, TRP-1 receptor modulator, a calcium channel blocker, a mucin secretagogue, MUC1 stimulant, a calcineurin inhibitor, a corticosteroid, a P2Y2 receptor agonist, a muscarinic receptor agonist, an mTOR inhibitor, another JAK inhibitor, Bcr-Abl kinase inhibitor, Flt-3 kinase inhibitor, RAF kinase inhibitor, and FAK kinase inhibitor such as, for example, those described in WO 2006/056399, which is incorporated herein by reference in its entirety. In some embodiments, the additional therapeutic agent is a tetracycline derivative (e.g., minocycline or doxycline). In some embodiments, the additional therapeutic agent binds to FKBP12.

In some embodiments, the additional therapeutic agent is an alkylating agent or DNA cross-linking agent; an antimetabolite/demethylating agent (e.g., 5-flurouracil, capecitabine or azacitidine); an anti-hormone therapy (e.g., hormone receptor antagonists, SERMs, or aromatase inhibitor); a mitotic inhibitor (e.g. vincristine or paclitaxel); an topoisomerase (I or II) inhibitor (e.g. mitoxantrone and irinotecan); an apoptotic inducers (e.g. ABT-737); a nucleic acid therapy (e.g. antisense or RNAi); nuclear receptor ligands (e.g., agonists and/or antagonists: all-trans retinoic acid or bexarotene); epigenetic targeting agents such as histone deacetylase inhibitors (e.g. vorinostat), hypomethylating agents (e.g. decitabine); regulators of protein stability such as Hsp90 inhibitors, ubiquitin and/or ubiquitin like conjugating or deconjugating molecules; or an EGFR inhibitor (erlotinib).

In some embodiments, the additional therapeutic agent(s) are demulcent eye drops (also known as "artificial tears"), which include, but are not limited to, compositions containing polyvinylalcohol, hydroxypropyl methylcellulose, glycerin, polyethylene glycol (e.g. PEG400), or carboxymethyl cellulose. Artificial tears can help in the treatment of dry eye by compensating for reduced moistening and lubricating capacity of the tear film. In some embodiments, the additional therapeutic agent is a mucolytic drug, such as N-acetyl-cysteine, which can interact with the mucoproteins and, therefore, to decrease the viscosity of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

In some embodiments, the additional therapeutic agent is an inhibitor of one or more Pim kinases. The second therapeutic agent in the methods and compositions of the present invention can be any active agent, such as a chemical compound or a macromolecule or a biopolymer, that inhibits at least one Pim kinase, such as Pim-1, Pim-2, or Pim-3. In some embodiments, the Pim inhibitor inhibits Pim-1. In some embodiments, the Pim inhibitor inhibits Pim-2. In some embodiments, the Pim inhibitor inhibits Pim-3. In some embodiments, the Pim inhibitor inhibits Pim-1, Pim-2, and Pim-3. In some embodiments, the Pim inhibitor is selective for one or more Pims over other kinases. In further embodiments, the Pim inhibitor is a selective inhibitor of Pim-1 over Pim-2 and Pim-3. In further embodiments, the Pim inhibitor is a selective inhibitor of Pim-2 over Pim-1 and Pim-3. In yet further embodiments, the Pim inhibitor is a selective inhibitor of Pim-3 over Pim-1 and Pim-2.

A selective Pim inhibitor generally inhibits the Pim kinase target it is selective for with more potency than for the target is it selective against. In some embodiments, the selectivity can be at least about 2-fold, at least about 3-fold, at least about 5-fold, at least about 10-fold, at least about 20-fold, at least about 50-fold, or at least about 100-fold. Potency can be measured by one or more in vitro assays, such as the assays provided below in the Examples.

Example Pim kinase inhibitors include the compounds described in U.S. Pat. No. 7,750,007, WO 2011/057784, WO 2011/029802, WO 2010/026121, WO 2010/026122, WO 2010/026124, WO 2010/022081, WO 2010/022076, WO 2010/001169, WO 2010/000978, WO 2009/064486, WO 2009/109576, WO 2008/106692, WO 2008/124323 (US 2010/029633), WO 2008/082840 (US 2008/161578), WO 2008/082839 (U.S. Pat. App. Pub. No. 2008/161559), WO 2008/058126 (U.S. Pat. No. 7,750,007), and WO 2008/022164 (U.S. Pat. App. Pub. No. 2010/210627), each of which is incorporated herein by reference in its entirety.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose, and polyethylene oxide. In some embodiments, the composition comprises at least one compound described herein, or a pharmaceutically acceptable salt thereof, and microcrystalline cellulose, lactose monohydrate, and hydroxypropyl methylcellulose. In some embodiments, the composition comprises at least one compound described herein, or a pharmaceutically acceptable salt thereof, and microcrystalline cellulose, lactose monohydrate, and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions of the invention contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions of the invention contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

In some embodiments, the compound, or pharmaceutically acceptable salt thereof, is administered as an ophthalmic composition. Accordingly, in some embodiments, the methods comprise administration of the compound, or pharmaceutically acceptable salt thereof, and an ophthalmically acceptable carrier. In some embodiments, the ophthalmic composition is a liquid composition, semi-solid composition, insert, film, microparticles or nanoparticles.

In some embodiments, the ophthalmic composition is a liquid composition. In some embodiments, the ophthalmic composition is a semi-solid composition. In some embodiments, the ophthalmic composition is a topical composition. The topical compositions include, but are not limited to liquid and semi-solid compositions. In some embodiments, the ophthalmic composition is a topical composition. In some embodiments, the topical composition comprises aqueous solution, an aqueous suspension, an ointment or a gel. In some embodiments, the ophthalmic composition is topically applied to the front of the eye, under the upper eyelid, on the lower eyelid and in the cul-de-sac. In some embodiments, the ophthalmic composition is sterilized. The sterilization can be accomplished by known techniques like sterilizing filtration of the solution or by heating of the solution in the ampoule ready for use. The ophthalmic compositions of the invention can further contain pharmaceutical excipients suitable for the preparation of ophthalmic formulations. Examples of such excipients are preserving agents, buffering agents, chelating agents, antioxidant agents and salts for regulating the osmotic pressure.

As used herein, the term "ophthalmically acceptable carrier" refers to any material that can contain and release the compound, or pharmaceutically acceptable salt thereof, and that is compatible with the eye. In some embodiments, the ophthalmically acceptable carrier is water or an aqueous solution or suspension, but also includes oils such as those used to make ointments and polymer matrices such as used in ocular inserts. In some embodiments, the composition may be an aqueous suspension comprising the compound, or pharmaceutically acceptable salt thereof. Liquid ophthalmic compositions, including both ointments and suspensions, may have a viscosity that is suited for the selected route of administration. In some embodiments, the ophthalmic composition has a viscosity in the range of from about 1,000 to about 30,000 centipoise.

In some embodiments, the ophthalmic compositions may further comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxpropyl-guar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

Aqueous ophthalmic compositions (solutions or suspensions) generally do not contain physiologically or ophthalmically harmful constituents. In some embodiments, purified or deionized water is used in the composition. The pH may be adjusted by adding any physiologically and ophthalmically acceptable pH adjusting acids, bases or buffers to within the range of about 5.0 to 8.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Salts and buffers include citrate/dextrose, sodium bicarbonate, ammonium chloride and mixtures of the aforementioned acids and bases.

In some embodiments, the methods involve forming or supplying a depot of the therapeutic agent in contact with the external surface of the eye. A depot refers to a source of therapeutic agent that is not rapidly removed by tears or other eye clearance mechanisms. This allows for continued, sustained high concentrations of therapeutic agent to be present in the fluid on the external surface of the eye by a single application. Without wishing to be bound by any theory, it is believed that absorption and penetration may be dependent on both the dissolved drug concentration and the contact duration of the external tissue with the drug containing fluid. As the drug is removed by clearance of the ocular fluid and/or absorption into the eye tissue, more drug is provided, e.g. dissolved, into the replenished ocular fluid from the depot. Accordingly, the use of a depot may more easily facilitate loading of the ocular tissue for more insoluble therapeutic agents. In some embodiments, the depot can remain for up to eight hours or more. In some embodiments, the ophthalmic depot forms includes, but is not limited to, aqueous polymeric suspensions, ointments, and solid inserts.

In some embodiments, the ophthalmic composition is an ointment or gel. In some embodiment, the ophthalmic composition is an oil-based delivery vehicle. In some embodiments, the composition comprises a petroleum or lanolin base to which is added the active ingredient, usually as 0.1 to 2%, and excipients. Common bases may include, but are not limited to, mineral oil, petrolatum and combinations thereof. In some embodiments, the ointment is applied as a ribbon onto the lower eyelid.

In some embodiments, the ophthalmic composition is an ophthalmic insert. In some embodiments, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the therapeutic agent is generally dispersed therein or bonded to the polymer matrix. In some embodiments, the therapeutic agent may be slowly released from the matrix through dissolution or hydrolysis of the covalent bond. In some embodiments, the polymer is bioerodible (soluble) and the dissolution rate thereof can control the release rate of the therapeutic agent dispersed therein. In another form, the polymer matrix is a biodegradable polymer that breaks down such as by hydrolysis to thereby release the therapeutic agent bonded thereto or dispersed therein. In further embodiments, the matrix and therapeutic agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly (dl-lactide-co-glycolide) (PLGA), or a copolymer of any of these. In some embodiments, the therapeutic agent is dispersed into the matrix material or dispersed amongst the monomer composition used to make the matrix material prior to polymerization. In some embodiments, the amount of therapeutic agent is from about 0.1 to about 50%, or from about 2 to about 20%. In further embodiments, the biodegradable or bioerodible polymer matrix is used so that the spent insert does not have to be removed. As the biodegradable or bioerodible polymer is degraded or dissolved, the therapeutic agent is released.

In further embodiments, the ophthalmic insert comprises a polymer, including, but are not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly(dimethyl siloxane), polyethylene oxide, poly(lactide-co-glycolide), poly(2-hydroxyethylmethacrylate), poly(vinyl alcohol), or poly(propylene fumarate). In some embodiments, the insert comprises Gelfoam® R. In some embodiments, the insert is a polyacrylic acid of 450 kDa-cysteine conjugate.

In some embodiments, the ophthalmic composition is a ophthalmic film. Polymers suitable for such films include, but are not limited to, those described in Wagh, et al. (ibid), In some embodiments, the film is a soft-contact lens, such as ones made from copolymers of N,N-diethylacrylamide and methacrylic acid crosslinked with ethyleneglycol dimethacrylate.

In some embodiments, the ophthalmic composition comprises microspheres or nanoparticles. In some embodiment, the microspheres comprise gelatin. In some embodiments, the microspheres are injected to the posterior segment of the eye, in the chroroidal space, in the sclera, intravitreally or sub-retinally. In some embodiments, the microspheres or nanoparticles comprises a polymer including, but not limited to, those described in Wagh, et al. (ibid), which is incorporated herein by reference in its entirety. In some embodiments, the polymer is chitosan, a polycarboxylic acid such as polyacrylic acid, albumin particles, hyaluronic acid esters, polyitaconic acid, poly(butyl)cyanoacrylate, polycaprolactone, poly(isobutyl)caprolactone, poly(lactic acid-co-glycolic acid), or poly(lactic acid). In some embodiments, the microspheres or nanoparticles comprise solid lipid particles.

In some embodiments, the ophthalmic composition comprises an ion-exchange resin. In some embodiments, the ion-exchange resin is an inorganic zeolite or synthetic organic resin. In some embodiments, the ion-exchange resin includes, but is not limited to, those described in Wagh, et al. (ibid), which is incorporated herein by reference in its entirety. In some embodiments, the ion-exchange resin is a partially neutralized polyacrylic acid.

In some embodiments, the ophthalmic composition is an aqueous polymeric suspension. In some embodiments, the therapeutic agent or a polymeric suspending agent is suspended in an aqueous medium. In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro JAK labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is to be understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a JAK by monitoring its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be JAK inhibitors according to at least one assay described infra.

EXAMPLES

Experimental procedures for compounds of the invention are provided below. Open Access Prep LC-MS Purification of some of the compounds prepared was performed on Waters mass directed fractionation systems. The basic equipment setup, protocols, and control software for the operation of these systems have been described in detail in literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity under the following conditions: Instrument; Agilent 1100 series, LC/MSD, Column: Waters Sunfire™ $C_{18}$ 5 μm, 2.1×5.0 mm, Buffers: mobile phase A: 0.025% TFA in water and mobile phase B: 0.025% TFA in acetonitrile; gradient 2% to 80% of B in 3 minutes with flow rate 1.5 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm column, eluting with mobile phase A: 0.1% TFA (trifluoroacetic acid) in water and mobile phase B: 0.1% TFA in acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the with 30×100 mm column was 60 mL/minute.

pH=10 purifications: Waters XBridge $C_{18}$ 5 μm, 19×100 mm column, eluting with mobile phase A: 0.15% $NH_4OH$ in water and mobile phase B: 0.15% $NH_4OH$ in acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1. 4-{3-(Cyanomethyl)-3-[4-(1H-pyrrolo[2,3-b]pyridin-4-yl)-1H-pyrazol-1-yl]azetidin-1-yl}-N-isopropylbenzamide

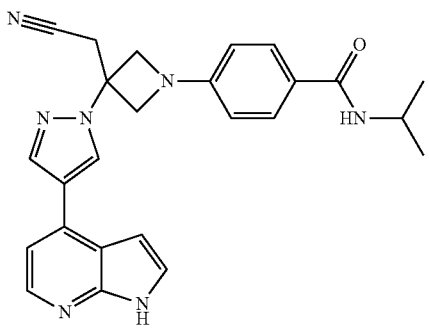 [SMILES: CC(C)NC(=O)c1ccc(N2CC(CC#N)(n3cc(-c4ccnc5[nH]ccc45)cn3)C2)cc1]

Step 1: ethyl 4-(3-hydroxyazetidin-1-yl)benzoate

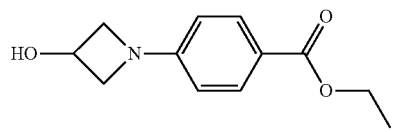

A mixture of ethyl 4-fluorobenzoate (0.841 g, 5.00 mmol, Aldrich: Cat.#102644), azetidin-3-ol hydrochloride (0.438 g, 4.00 mmol, Aldrich: Cat.#680079) and potassium carbonate (1.38 g, 9.98 mmol) in dimethyl sulfoxide (4 mL) was heated at 180° C. for 2 hours. After cooling, the mixture was diluted with ethyl acetate (50 mL), and washed with water and brine. The organic layer was dried over $MgSO_4$, filtered, and concentrated under reduced pressure. The residue was purified by flash chromatography on a silica gel column with ethyl acetate in hexane (0-50%) to afford the desired product (0.643 g, 72.6%). LCMS $(M+H)^+$: m/z=222.1.

Step 2: 4-(3-hydroxyazetidin-1-yl)benzoic acid

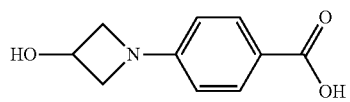

A mixture of 1-[4-(3-hydroxyazetidin-1-yl)phenyl]-2-methoxyethanone (1.33 g, 6.00 mmol) and lithium hydroxide monohydrate (504 mg, 12.0 mmol) in water (4 mL), methanol (3 mL) and THF (6 mL) was stirred at 40° C. overnight. The mixture was neutralized with 3 N HCl aqueous solution (~4 mL) to pH about 7, extracted with ethyl acetate, dried over $Na_2SO_4$, filtered and concentrated under reduced pressure to afford the crude product (1.10 g, 94.9%) which was directly used in next step reaction without further purification. LCMS $(M+H)^+$: m/z=194.1.

Step 3: 4-(3-hydroxyazetidin-1-yl)-N-isopropylbenzamide

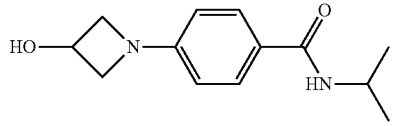 [SMILES: CC(C)NC(=O)c1ccc(N2CC(O)C2)cc1]

Benzotriazol-1-yloxytris(dimethylamino)phosphonium hexafluorophosphate (4.64 g, 10.5 mmol, Aldrich: Cat.#226084) was added to a mixture of 4-(3-hydroxyazetidin-1-yl)benzoic acid (1.93 g, 10.0 mmol), 2-propanamine (4.26 mL, 50.0 mmol) and N,N-diisopropylethylamine (3.88 g, 30.0 mmol) in dichloromethylene (10 mL). The mixture was stirred at room temperature for 2 hours, and diluted with DCM. The mixture was washed with aqueous $NaHCO_3$ and brine, dried over $Na_2SO_4$, filtered and concentrated under reduced pressure. The residue was purified by flash chromatography on a silica gel column with ethyl acetate in hexane (gradient: 0-50%) to afford the desired product (2.21 g, 94.3%). LCMS $(M+H)^+$: m/z=235.1.

Step 4: N-isopropyl-4-(3-oxoazetidin-1-yl)benzamide

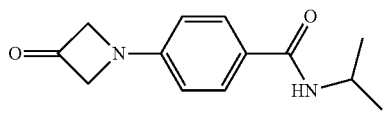 [SMILES: CC(C)NC(=O)c1ccc(N2CC(=O)C2)cc1]

To a cooled (−78° C.) solution of oxalyl chloride (1.05 mL, 12.4 mmol) in dichloromethylene (20 mL) was added dropwise dimethyl sulfoxide (1.71 mL, 24.1 mmol). The mixture was stirred at −78° C. for 10 minutes. Then a suspension of 4-(3-hydroxyazetidin-1-yl)-N-isopropylbenzamide (1.72 g, 7.34 mmol) in dichloromethylene (20 mL) was added. The mixture was stirred at −78° C. for 1 hour, and then triethylamine (7.04 mL, 50.5 mmol) was added. The mixture was stirred at −78° C. for an additional 1.5 hour. The mixture was washed with aq. $NaHCO_3$ and brine, dried over $Na_2SO_4$, filtered and concentrated under reduced pressure. The precipitates were washed with ether and collected by filtration to afford the desired product (1.32 g, 77%) which was directly used in the next step reaction without further purification. LCMS $(M+H)^+$: m/z=233.1.

Step 5: 4-[3-(cyanomethylene)azetidin-1-yl]-N-isopropylbenzamide

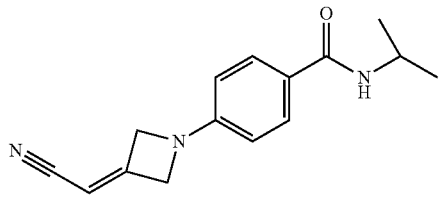 [SMILES: CC(C)NC(=O)c1ccc(N2CC(=CC#N)C2)cc1]

To a cooled (at −6 to 0° C.) solution of 1.0 M potassium tert-butoxide in tetrahydrofuran (7.10 mL, 7.10 mmol) was added dropwise a solution of diethyl cyanomethylphosphonate (1.20 mL, 7.43 mmol, Aldrich: Cat.#D91705) in tetrahydrofuran (10.0 mL) over a period of 10 minutes and at −6 to 0° C. The reaction was warmed and stirred at room temperature for 1 hour. The reaction mixture was re-cooled at −6° C. To the reaction mixture was then added a solution of N-isopropyl-4-(3-oxoazetidin-1-yl)benzamide (1.30 g, 5.60 mmol) in tetrahydrofuran (10.0 mL) over a period of 10 minutes. During this time the temperature of the reaction mixture was between −5 to 0° C. The reaction was allowed to warm to room temperature and was stirred for 3 hours. The reaction mixture was filtered through a pad of silica gel and washed with ethyl acetate. The filtrate was concentrated, and the residue was treated with ether. The precipitates formed were collected by filtration to give 0.60 g desired product. The mother liquid was concentrated under reduced pressure. The residue was purified by flash chromatography on a silica gel column with ethyl acetate in hexane (gradient: 30-80%) to afford the desired product (0.21 g). the total product is 0.81 g (57%). LCMS $(M+H)^+$: m/z=256.1.

Step 6: 4-bromo-1-{[2-(trimethylsilyl)ethoxy]methyl}-1H-pyrrolo[2,3-b]pyridine

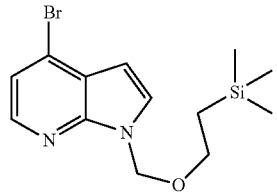 [SMILES: C[Si](C)(C)CCOCn1ccc2c(Br)ccnc21]

4-Bromo-1H-pyrrolo[2,3-b]pyridine (10.0 g, 0.0508 mol, Aldrich: Cat.#703451) was dissolved in N,N-dimethylformamide (100 mL) and cooled under nitrogen to 0° C. Sodium hydride (3.00 g, 0.0750 mol, 60% dispersion in mineral oil) was added portion-wise. The reaction was stirred for 10 minutes. [β-(Trimethylsilyl)ethoxy]methyl chloride (10.8 mL, 0.0609 mol, Aldrich: Cat.#238902) was added slowly to the reaction mixture, stirred at 0° C. for 45 minutes, and allowed to warm to room temperature. The solvent was removed under reduced pressure. The residue was diluted with ethyl ether (100 mL), and washed with water and brine, dried over sodium sulfate and concentrated under reduced pressure. The residue was purified by flash chromatography on a silica gel column with ethyl acetate in hexane (0-25%) to afford the desired product (16.04 g, 96.6%). LCMS $(M+H)^+$: m/z=327.0/329.0

Step 7: 4-(1H-pyrazol-4-yl)-1-{[2-(trimethylsilyl)ethoxy]methyl}-1H-pyrrolo[2,3-b]pyridine

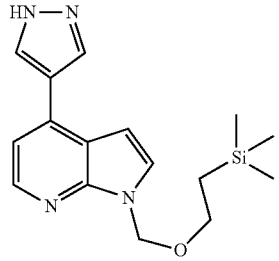 [SMILES: C[Si](C)(C)CCOCn1ccc2c(-c3cn[nH]c3)ccnc21]

A mixture of 4-bromo-1-{[2-(trimethylsilyl)ethoxy]methyl}-1H-pyrrolo[2,3-b]pyridine (1.63 g, 4.98 mmol), tert-butyl 4-(4,4,5,5-tetramethyl-1,3,2-dioxaborolan-2-yl)-1H-pyrazole-1-carboxylate (1.61 g, 5.48 mmol, Aldrich: Cat.#632732), tetrakis(triphenylphosphine)palladium(0) (288 mg, 0.249 mmol) and sodium carbonate (1.58 g, 14.9 mmol) in 1,4-dioxane (16.0 mL) and water (8.0 mL) was stirred at 110° C. for 2 hours. After cooling, the mixture was diluted with ethyl acetate, and washed with water and brine, dried over Na$_2$SO$_4$, filtered and concentrated under reduced pressure. The residue was treated with ether, filtered and washed with ether to afford the desired product (1.08 g, 69%) which was directly used in next step reaction without further purification. LCMS (M+H)$^+$: m/z=315.1.

Step 8: 4-{3-(cyanomethyl)-3-[4-(1-{[2-(trimethylsilyl)ethoxy]methyl}-1H-pyrrolo[2,3-b]pyridin-4-yl)-1H-pyrazol-1-yl]azetidin-1-yl}-N-isopropylbenzamide

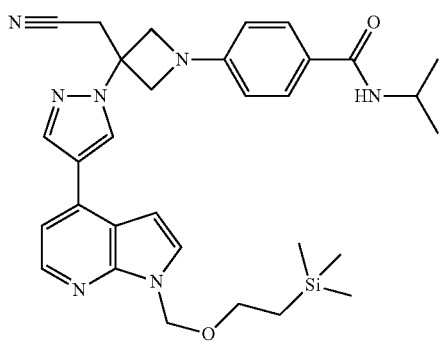 [SMILES: CC(C)NC(=O)c1ccc(N2CC(CC#N)(n3cc(-c4ccnc5c4ccn5COCC[Si](C)(C)C)cn3)C2)cc1]

A mixture of 4-(1H-pyrazol-4-yl)-1-{[2-(trimethyl silyl)ethoxy]methyl}-1H-pyrrolo[2,3-b]pyridine (0.811 g, 2.58 mmol), 4-[3-(cyanomethylene)azetidin-1-yl]-N-isopropylbenzamide (0.625 g, 2.45 mmol) and 1,8-diazabicyclo[5.4.0]undec-7-ene (190 μL, 1.3 mmol) in acetonitrile (8 mL, 200 mmol) was heated at 50° C. for 1 hour. After cooling, the solvent was removed under reduced pressure. The residue was diluted with dichloromethylene, neutralized with 0.5 N HCl aqueous solution to about pH 7. The organic layer was washed with brine, dried over MgSO$_4$, filtered and concentrated under reduced pressure to afford the desired product (1.40 g, 84.3%), which was directly used in the next step reaction without further purification. LCMS (M+H)$^+$: m/z=570.3.

Step 9: 4-{3-(cyanomethyl)-3-[4-(1H-pyrrolo[2,3-b]pyridin-4-yl)-1H-pyrazol-1-yl]azetidin-1-yl}-N-isopropylbenzamide

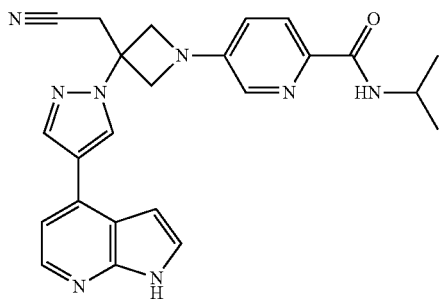 [SMILES: CC(C)NC(=O)c1ccc(N2CC(CC#N)(n3cc(-c4ccnc5[nH]ccc45)cn3)C2)cn1]

4-{3-(Cyanomethyl)-3-[4-(1-{[2-(trimethylsilyl)ethoxy]methyl}-1H-pyrrolo[2,3-b]pyridin-4-yl)-1H-pyrazol-1-yl]azetidin-1-yl}-N-isopropylbenzamide was dissolved in dichloromethylene (5 mL). To the solution was added trifluoroacetic acid (TFA) (2.5 mL). The mixture was stirred at room temperature for 1 hour. The volatiles were removed under reduced pressure. The residue was dissolved in methanol (10 mL). To the solution was added ethylenediamine (1 mL). The mixture was stirred at room temperature for 4 hours, and was purified by RP-HPLC (pH=10) to afford the desired product (0.415 g). LCMS (M+H)$^+$: m/z=440.1. The high purity (99.6%) of the product was obtained by re-crystallization from acetone-ether. $^1$H NMR (400 MHz, CDCl$_3$): δ 9.57 (s, 1H), 8.31 (d, J=4.9 Hz, 1H), 8.15 (s, 1H), 8.11 (s, 1H), 7.70 (m, 2H), 7.39 (d, J=3.4 Hz, 1H), 7.18 (d, J=4.9 Hz, 1H), 6.70 (d, J=3.4 Hz, 1H), 6.55 (m, 2H), 5.79 (d, J=7.8 Hz, 1H), 4.47 (d, J=8.3 Hz, 2H), 4.38 (d, J=8.3 Hz, 2H), 4.27 (m, 1H), 3.45 (s, 2H), 1.25 (d, J=6.7 Hz, 6H).

Example 2. 5-{3-(Cyanomethyl)-3-[4-(1H-pyrrolo[2,3-b]pyridin-4-yl)-1H-pyrazol-1-yl]azetidin-1-yl}-N-[(1S)-1-cyclopropylethyl]pyridine-2-carboxamide

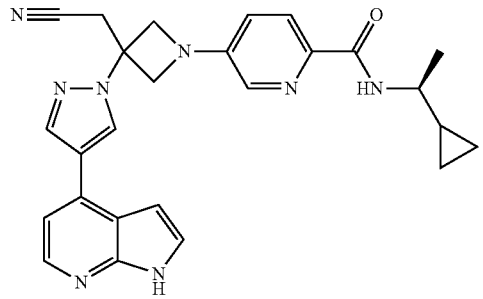 [SMILES: C[C@H](NC(=O)c1ccc(N2CC(CC#N)(n3cc(-c4ccnc5[nH]ccc45)cn3)C2)cn1)C1CC1]

Step 1: 5-bromo-N-[(1S)-1-cyclopropylethyl]pyridine-2-carboxamide (1S)-1-Cyclopropylethanamine (0.50 mL, 5.4 mmol, Alfa Aesar: Cat.#H27499) was added to a mixture of 5-bromopyridine-2-carboxylic acid (1.0 g, 5.0 mmol, Alfa Aesar: Cat.#B25675) in methylene chloride (30.0 mL), followed by benzotriazol-1-yloxytris(dimethylamino)phosphonium hexafluorophosphate (2.4 g, 5.4 mmol) and N,N-diisopropylethylamine (1.7 mL, 9.9 mmol). The reaction mixture was stirred at room temperature overnight. The reaction mixture was worked up with aqueous Na$_2$CO$_3$, and extracted with dichloromethylene (3×20 mL). The combined organic layers were washed with brine, dried over MgSO$_4$, filtered and concentrated under reduced pressure. The residue was purified by flash chromatography on a silica gel column with ethyl acetate in hexanes (0-15%) to afford the desired product. LCMS (M+H)$^+$: m/z=269.0/271.0.

Step 2: tert-butyl 3-(cyanomethylene)azetidine-1-carboxylate

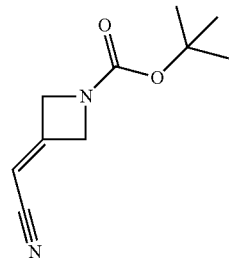

To a solution of 1.0 M potassium tert-butoxide in tetrahydrofuran (30.7 mL, 0.0307 mol) at 0° C. was added dropwise a solution of diethyl cyanomethylphosphonate (5.20 mL, 0.0322 mol) in tetrahydrofuran (39.12 mL). The reaction was warmed to room temperature and then cooled at 0° C. again. To the reaction mixture was added a solution of tert-butyl 3-oxoazetidine-1-carboxylate (5.0 g, 0.029 mol, Aldrich: Cat.#696315) in tetrahydrofuran (7.82 mL). The reaction was allowed to warm to room temperature and stirred overnight. After quenched with water, the mixture was extracted with ethyl acetate. The combined organic layers were washed with brine, dried over MgSO$_4$ and evaporated under reduced pressure. The crude mixture was purified by flash chromatography on a silica gel column with ethyl acetate in hexanes (0-70%) to give the desired product (5.40 g, 95%). LCMS (M+Na)$^+$: m/z=217.1.

Step 3: tert-butyl 3-(cyanomethyl)-3-[4-(1-{[2-(trimethylsilyl)ethoxy]methyl}-1H-pyrrolo[2,3-b]pyridin-4-yl)-1H-pyrazol-1-yl]azetidine-1-carboxylate

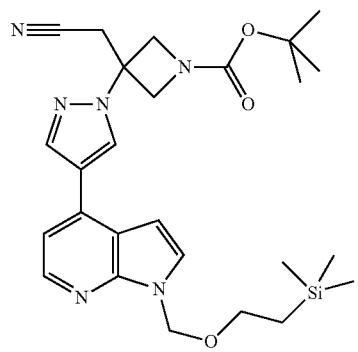 [SMILES: CC(C)(C)OC(=O)N1CC(CC#N)(n2cc(-c3ccnc4c3ccn4COCC[Si](C)(C)C)cn2)C1]

A mixture of 4-(1H-pyrazol-4-yl)-1-{[2-(trimethylsilyl)ethoxy]methyl}-1H-pyrrolo[2,3-b]pyridine (0.527 g, 1.68 mmol), tert-butyl 3-(cyanomethylene)azetidine-1-carboxylate (0.358 g, 1.84 mmol) and 1,8-diazabicyclo[5.4.0]undec-7-ene (135 µL, 0.903 mmol) in acetonitrile (4.0 mL) was heated at 50° C. for 1 hour. After cooling, the solvent was removed under reduced pressure. The residue was diluted with ethyl acetate, neutralized with 0.5 N HCl aqueous solutions, washed brine, dried over Na$_2$SO$_4$, filtered and concentrated under reduced pressure to afford the desired product (0.85 g, quantitative) which was directly used in next step reaction without further purification. LCMS (M+H)$^+$: m/z=509.3.

Step 4: {3-[4-(1-{[2-(trimethylsilyl)ethoxy]methyl}-1H-pyrrolo[2,3-b]pyridin-4-yl)-1H-pyrazol-1-yl]azetidin-3-yl}acetonitrile

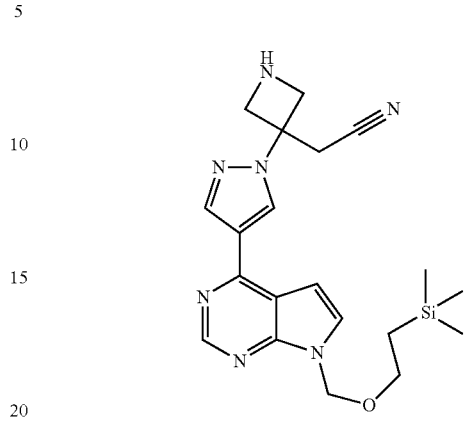

tert-Butyl 3-(cyanomethyl)-3-[4-(1-{[2-(trimethylsilyl)ethoxy]methyl}-1H-pyrrolo[2,3-b]pyridin-4-yl)-1H-pyrazol-1-yl]azetidine-1-carboxylate (0.85 g, 1.7 mmol) was dissolved in ethyl acetate (2 mL). To the solution was added 4.0 M hydrogen chloride in 1,4-dioxane (2.0 mL, 8.0 mmol). The mixture was stirred at room temperature for 3 hours. Ether was added, the mixture was centrifuged, and then the solvents were decanted. The residue was dried under vacuum to afford the desired product as HCl salt which was directly used in next step reaction without further purification. LCMS (M+H)$^+$: m/z=409.2

Step 5: 5-{3-(cyanomethyl)-3-[4-(1-{[2-(trimethylsilyl)ethoxy]methyl}-1H-pyrrolo[2,3-b]pyridin-4-yl)-1H-pyrazol-1-yl]azetidin-1-yl}-N-[(1S)-1-cyclopropylethyl]pyridine-2-carboxamide

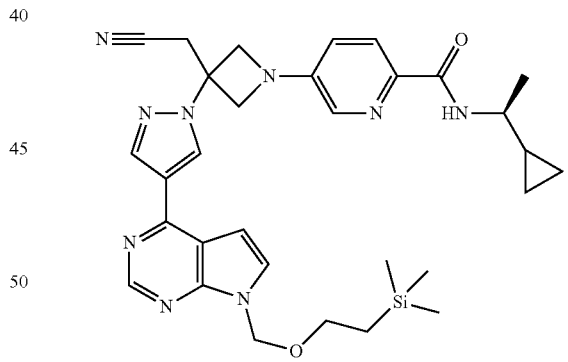

2,2'-Bis(diphenylphosphino)-1,1'-binaphthyl (91.1 mg, 0.146 mmol, Aldrich: Cat.#481084) was added to a mixture of {3-[4-(1-{[2-(trimethylsilyl)ethoxy]methyl}-1H-pyrrolo[2,3-b]pyridin-4-yl)-1H-pyrazol-1-yl]azetidin-3-yl}acetonitrile hydrochloride (0.445 g, 1.00 mmol), 5-bromo-N-[(1S)-1-cyclopropylethyl]pyridine-2-carboxamide (0.273 g, 1.01 mmol), and cesium carbonate (0.971 g, 2.98 mmol) in toluene (10 mL) under N$_2$, followed by palladium acetate (32.2 mg, 0.143 mmol). The reaction mixture was stirred at 120° C. overnight. The reaction mixture was worked up with aqueous NaHCO$_3$, and extracted with ethyl acetate (3×30 mL). The combined organic layers were washed with brine, dried over MgSO$_4$, filtered and concentrated under reduced pressure. The residue was purified by flash chromatography on a silica gel column with ethyl acetate in hexane (0-70%) to afford the desired product (0.350 g, 58.6%). LCMS (M+H)⁺: m/z=597.3.

Step 6: 5-{3-(cyanomethyl)-3-[4-(1H-pyrrolo[2,3-b]pyridin-4-yl)-1H-pyrazol-1-yl]azetidin-1-yl}-N-[(1S)-1-cyclopropylethyl]pyridine-2-carboxamide 5-{3-(Cyanomethyl)-3-[4-(1-{[2-(trimethylsilyl)ethoxy]methyl}-1H-pyrrolo[2,3-b]pyridin-4-yl)-1H-pyrazol-1-yl]azetidin-1-yl}-N-[(1S)-1-cyclopropylethyl]pyridine-2-carboxamide (0.350 g, 0.75 mmol) was dissolved in dichloromethylene (3 mL). To the solution was added TFA (1.5 mL). The mixture was stirred at room temperature for 2 hours. The volatiles were evaporated under reduced pressure. The residue was dissolved in methanol (5 mL), and ethylenediamine (1.0 mL) was added. The mixture was stirred at room temperature overnight, and was purified by RP-HPLC (pH=10) to afford the desired product. LCMS (M+H)⁺: m/z=467.3.

Example 3. 4-{3-(Cyanomethyl)-3-[4-(7H-pyrrolo[2,3-d]pyrimidin-4-yl)-1H-pyrazol-1-yl]azetidin-1-yl}-3-fluoro-N-isopropylbenzamide

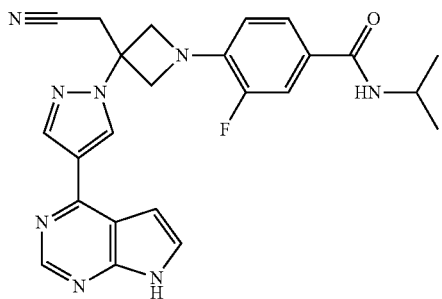 [SMILES: CC(C)NC(=O)c1ccc(N2CC(CC#N)(n3cc(-c4ncnc5[nH]ccc45)cn3)C2)c(F)c1]

Step 1: 4-bromo-3-fluoro-N-isopropylbenzamide

2-Propanamine (1.2 mL, 14 mmol) was added to a mixture of 4-bromo-3-fluorobenzoic acid (2.09 g, 9.54 mmol, Alfa Aesar: Cat.#B25475) in methylene chloride (52.2 mL, 815 mmol), followed by benzotriazol-1-yloxytris(dimethylamino)-phosphonium hexafluorophosphate (4.6 g, 10. mmol) and N,N-diisopropylethylamine (3.3 mL, 19 mmol). The reaction mixture was stirred at room temperature overnight. The reaction mixture was worked up with aqueous NaHCO₃, and extracted with dichloromethylene (3×20 mL). The combined organic layers were washed with brine, dried over MgSO₄, filtered and concentrated under reduced pressure. The residue was purified by flash chromatography on a silica gel column with ethyl acetate in hexanes (0-20%) to afford the desired product (2.28 g, 91.8%). LCMS (M+H)⁺: m/z=260.0/262.0.

Step 2: 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-3-fluoro-N-isopropylbenzamide

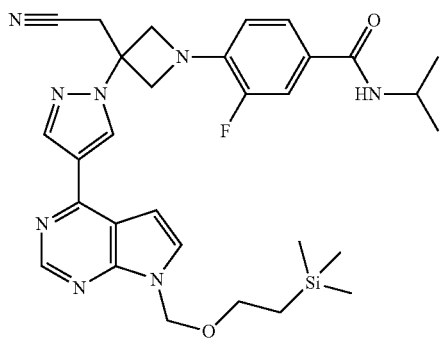 [SMILES: CC(C)NC(=O)c1ccc(N2CC(CC#N)(n3cc(-c4ncnc5c4ccn5COCC[Si](C)(C)C)cn3)C2)c(F)c1]

2,2'-Bis(diphenylphosphino)-1,1'-binaphthyl (0.32 g, 0.52 mmol) was added to a mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (2.50 g, 5.18 mmol) (see WO 2009/114512), 4-bromo-3-fluoro-N-isopropylbenzamide (1.6 g, 6.2 mmol), and cesium carbonate (5.1 g, 16 mmol) in toluene (120 mL) under N₂, followed by palladium acetate (0.12 g, 0.52 mmol). The reaction mixture was stirred at 120° C. for 5 hours. After the reaction mixture was cooled to room temperature, the organic layer was separated from the solid. The solid was dissolved in water (50 mL), extracted with ethyl acetate (3×50 mL). The combined organic layers were washed with brine, dried over MgSO₄, filtered, and concentrated under reduced pressure. The residue was purified by flash chromatography on a silica gel column with ethyl acetate in dichloromethylene (0-40%) to afford the desired product (2.20 g, 72.1%). LCMS (M+H)⁺: m/z=589.3.

Step 3: 4-{3-(cyanomethyl)-3-[4-(7H-pyrrolo[2,3-d]pyrimidin-4-yl)-1H-pyrazol-1-yl]azetidin-1-yl}-3-fluoro-N-isopropylbenzamide Boron trifluoride etherate (2.0 mL, 16 mmol) was added to a solution of 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-3-fluoro-N-isopropylbenzamide (2.20 g, 3.74 mmol) in acetonitrile (30.0 mL) at 0° C. under N₂. The reaction mixture was stirred at room temperature overnight. The reaction was cooled to 0° C., water (5 mL) was added. After stirring at room temperature for 30 minutes, 5.0 M ammonium hydroxide in water (9 mL, 50 mmol) was added slowly at 0° C. over a period of 5 minutes. Then the reaction mixture was stirred at room temperature overnight. The reaction mixture was worked up with aqueous NaHCO₃, and extracted with ethyl acetate (3×20 mL). The combined organic layers were washed with brine, dried over MgSO₄, filtered and concentrated under reduced pressure. The residue was purified by flash chromatography on a silica gel column with MeOH in dichloromethylene (0-5%) to afford the desired product (1.50 g, 63%) which was further purified by re-crystallization from acetone to afford the pure product (1.25 g, purity: 99.96%). The product was then converted to TFA salt. LCMS (M+H)⁺: m/z=459.2. ¹H NMR (300 Hz, DMSO-d₆): δ 12.73 (s, 1H), 9.11 (s, 1H), 8.85 (s, 1H), 8.57 (s, 1H), 8.03 (d, J=8.0 Hz, 1H), 7.81 (t, J=2.5 Hz, 1H), 7.64 (s, 1H), 7.60 (t, J=2.5 Hz, 1H), 7.27 (d, J=2.5 Hz, 1H), 6.72 (t, J=9.0 Hz, 1H), 4.66 (d, J=7.0 Hz, 2H), 4.41 (d, J=7.0 Hz, 2H), 4.04 (m, 1H), 3.73 (s, 2H), 1.12 (d, J=6.5 Hz, 6H).

Example 4. 4-{3-(Cyanomethyl)-3-[4-(7H-pyrrolo[2,3-d]pyrimidin-4-yl)-1H-pyrazol-1-yl]azetidin-1-yl}-N-[(1R)-1-cyclopropylethyl]-3-fluorobenzamide

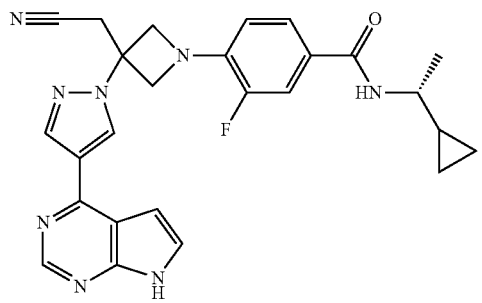 [SMILES: C[C@@H](NC(=O)c1ccc(N2CC(CC#N)(n3cc(-c4ncnc5[nH]ccc45)cn3)C2)c(F)c1)C1CC1]

Step 1: 4-bromo-N-[(1R)-1-cyclopropylethyl]-3-fluorobenzamide

N,N-Diisopropylethylamine (0.92 mL, 5.3 mmol) was added to a mixture of 4-bromo-3-fluorobenzoic acid (0.58 g, 2.6 mmol), (1R)-1-cyclopropylethanamine (0.27 mL, 2.9 mmol, Alfa Aesar: Cat.#H26902) and benzotriazol-1-yloxytris(dimethylamino)-phosphonium hexafluorophosphate (1.3 g, 2.9 mmol) in methylene chloride (5.8 mL, 91 mmol). The reaction mixture was stirred at room temperature for 30 minutes, worked up with aqueous NaHCO$_3$, and extracted with dichloromethylene (3×20 mL). The combined organic layers were washed with brine, dried over MgSO$_4$, filtered and concentrated under reduced pressure. The residue was purified by flash chromatography on a silica gel column with ethyl acetate in hexanes (0-10%) to afford the desired product (0.71 g, 94%). LCMS (M+H)$^+$: m/z=286.0/288.0.

Step 2: 4-{3-(cyanomethyl)-3-[4-(7H-pyrrolo[2,3-d]pyrimidin-4-yl)-1H-pyrazol-1-yl]azetidin-1-yl}-N-[(1R)-1-cyclopropylethyl]-3-fluorobenzamide This compound was prepared as TFA salt by using procedures analogous to those described for the synthesis of Example 3, Step 2-3 starting from {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride and 4-bromo-N-[(1R)-1-cyclopropylethyl]-3-fluorobenzamide (from Step 1, above). LCMS (M+H)$^+$: m/z=485.2. $^1$H NMR (400 MHz, DMSO-d$_6$): δ 12.67 (s, 1H), 9.01 (s, 1H), 8.88 (s, 1H), 8.46 (s, 1H), 8.03 (d, J=8.0 Hz, 1H), 7.71 (t, J=2.5 Hz, 1H), 7.52 (s, 1H), 7.48 (s, 1H), 7.17 (d, J=2.5 Hz, 1H), 6.61 (t, J=8.4 Hz, 1H), 4.53 (d, J=8.0 Hz, 2H), 4.28 (d, J=8.0 Hz, 2H), 3.63 (s, 2H), 3.28 (m, 1H), 1.04 (d, J=6.5 Hz, 6H), 0.82 (m, 1H), 0.30 (m, 1H), 0.20 (m, 1H), 0.06 (m, 1H), 0.01 (m, 1H).

Example 5. 4-{3-(Cyanomethyl)-3-[4-(7H-pyrrolo[2,3-d]pyrimidin-4-yl)-1H-pyrazol-1-yl]azetidin-1-yl}-N-[(1S)-1-cyclopropylethyl]-3-fluorobenzamide

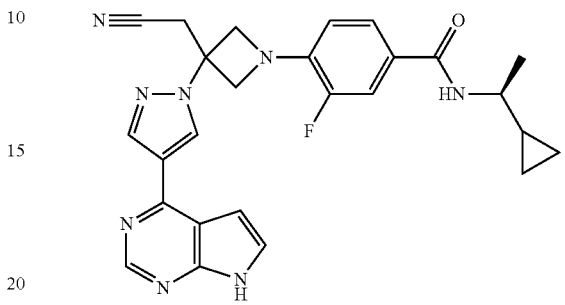

Step 1: methyl 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-3-fluorobenzoate

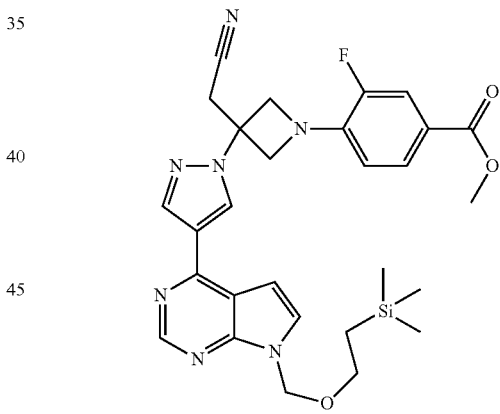

2,2'-Bis(diphenylphosphino)-1,1'-binaphthyl (0.11 g, 0.18 mmol) was added to a mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (0.86 g, 1.8 mmol), methyl 4-bromo-3-fluorobenzoate (0.50 g, 2.1 mmol, Combi-Blocks: Cat.#CA-4107), and cesium carbonate (1.7 g, 5.4 mmol) in toluene (25.0 mL) under N$_2$, followed by palladium acetate (0.040 g, 0.18 mmol). The reaction mixture was stirred at 120° C. for 5 hours. The reaction mixture was diluted with ethyl acetate, filtered, and concentrated under reduced pressure to afford the desired crude product (1.06 g) which was directly used in next step reaction without further purification. LCMS (M+H)$^+$: m/z=562.3.

Step 2: 4-{3-(cyanomethyl)-3-[4-(7-{[2-(trimethyl-silyl)ethoxy]methyl}-7H-pyrrolo[2,3-d]pyrimidin-4-yl)-1H-pyrazol-1-yl]azetidin-1-yl}-3-fluorobenzoic acid

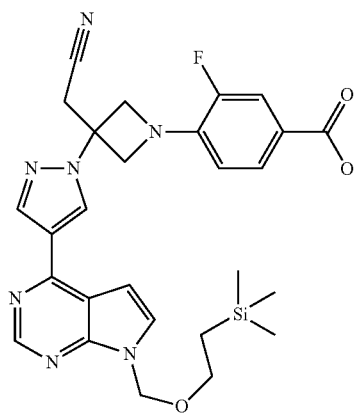 [SMILES: C[Si](C)(C)CCOCn1ccc2c(-c3cnn(C4(CC#N)CN(c5ccc(C(=O)O)cc5F)C4)c3)ncnc21]

Lithium hydroxide monohydrate (0.21 g, 5.0 mmol) was added to a mixture of methyl 4-{3-(cyanomethyl)-3-[4-(7-{[2-(trimethylsilyl)ethoxy]methyl}-7H-pyrrolo[2,3-d]py-rimidin-4-yl)-1H-pyrazol-1-yl]azetidin-1-yl}-3-fluoroben-zoate (1.06 g) in methanol (15.0 mL) and water (3.0 mL). The reaction mixture was stirred at 40° C. overnight. The mixture was adjusted to pH 3 with aqueous HCl (1.00 N), and concentrated under reduced pressure to remove methanol. The solid formed was filtered and washed with water, and dried under reduced pressure to afford the crude product (0.95 g) which was directly used in next step reaction without further purification. LCMS (M+H)$^+$: m/z=548.3.

Step 3: 4-{3-(cyanomethyl)-3-[4-(7H-pyrrolo[2,3-d]pyrimidin-4-yl)-1H-pyrazol-1-yl]azetidin-1-yl}-N-[(1S)-1-cyclopropylethyl]-3-fluorobenzamide A mixture of 4-{3-(cyanomethyl)-3-[4-(7-{[2-(trimethyl-silyl)ethoxy]methyl}-7H-pyrrolo[2,3-d]pyrimidin-4-yl)-1H-pyrazol-1-yl]azetidin-1-yl}-3-fluorobenzoic acid (20.0 mg, 0.0365 mmol) and benzotriazol-1-yloxytris(dimethyl-amino)phosphonium hexafluorophosphate (19 mg, 0.044 mmol) in dichloromethylene (1.0 mL) was added to a mixture of (1S)-1-cyclopropylethanamine (4.7 mg, 0.055 mmol) and triethylamine (15 μL, 0.11 mmol) in methylene chloride (0.6 mL). The reaction mixture was stirred at room temperature overnight. The reaction mixture was worked up with aqueous NaHCO$_3$, and extracted with dichloromethyl-ene (2×2 mL). The combined organic layers were washed with water (1 mL), concentrated and dried under reduced pressure. The residue was treated with methylene chloride (1.3 mL) and trifluoroacetic acid (0.6 mL), and stirred at room temperature for 1.5 hours. The mixture was concentrated under reduced pressure. The residue was dissolved in methanol (1.3 mL). Ethylenediamine (0.086 mL, 1.3 mmol) were added. The reaction mixture was stirred at room temperature for 2 hours, and purified by RP-HPLC (pH=10) (the conditions are already mention before the examples) to afford the desired product. LCMS (M+H)$^+$: m/z=485.2.

Example 6. 4-{3-(Cyanomethyl)-3-[4-(7H-pyrrolo[2,3-d]pyrimidin-4-yl)-1H-pyrazol-1-yl]azetidin-1-yl}-2,5-difluoro-N-isopropylbenzamide

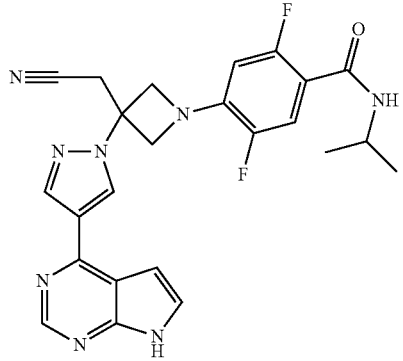 [SMILES: CC(C)NC(=O)c1cc(F)c(N2CC(CC#N)(n3cc(-c4ncnc5[nH]ccc45)cn3)C2)cc1F]

This compound was prepared by using procedures analogous to those described for the synthesis of Example 3, Step 1-3 starting from 4-chloro-2,5-difluorobenzoic acid (Aldrich: Cat.#443824), 2-propanamine and {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride. LCMS (M+H)$^+$: m/z=477.2. $^1$H NMR (400 MHz, DMSO-d$_6$): δ 12.61 (s, 1H), 9.08 (s, 1H), 8.84 (s, 1H), 8.57 (s, 1H), 7.80 (m, 2H), 7.37 (dd, J=13.0, 7.0 Hz, 1H), 7.23 (m, 1H), 6.63 (dd, J=13.0, 8.0 Hz, 1H), 4.51 (d, J=9.0 Hz, 2H), 4.42 (d, J=9.0 Hz, 2H), 3.78 (s, 2H), 4.03 (m, 1H), 1.13 (d, J=6.5 Hz, 6H).

Example 7. 4-{3-(Cyanomethyl)-3-[4-(7H-pyrrolo[2,3-d]pyrimidin-4-yl)-1H-pyrazol-1-yl]azetidin-1-yl}-N-cyclopropyl-3-fluoro-N-methylbenzamide

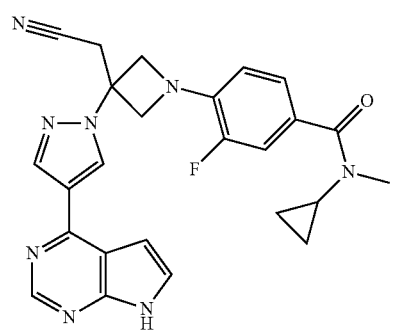 [SMILES: CN(C(=O)c1ccc(N2CC(CC#N)(n3cc(-c4ncnc5[nH]ccc45)cn3)C2)c(F)c1)C1CC1]

This compound was prepared by using procedures analogous to those described for the synthesis of Example 3, Step 1-3 starting from 4-bromo-3-fluorobenzoic acid, N-methyl-cyclopropanamine hydrochloride (J&W PharmLab: Cat.#20-0433S) and {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride. LCMS (M+H)$^+$: m/z=471.2. $^1$H NMR (400 MHz, DMSO-D$_6$): δ 12.83 (s, 1H), 9.17 (s, 1H), 8.91 (s, 1H), 8.60 (s, 1H), 7.85 (s, 1H), 7.33 (m, 3H), 6.71 (t, J=9.0 Hz, 1H), 4.66 (d, J=8.0 Hz, 2H), 4.41 (d, J=8.0 Hz, 2H), 3.79 (s, 2H), 2.97 (m, 1H), 2.93 (s, 3H), 0.59 (m, 2H), 0.42 (m, 2H).

Example 8. 5-Chloro-4-{3-(cyanomethyl)-3-[4-(7H-pyrrolo[2,3-d]pyrimidin-4-yl)-1H-pyrazol-1-yl]azetidin-1-yl}-2-fluoro-N-isopropylbenzamide

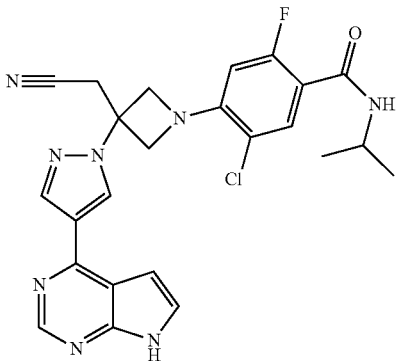 [SMILES: CC(C)NC(=O)c1cc(Cl)c(N2CC(CC#N)(n3cc(-c4ncnc5[nH]ccc45)cn3)C2)cc1F]

This compound was prepared by using procedures analogous to those described for the synthesis of Example 3, Step 1-3 starting from 4,5-dichloro-2-fluorobenzoic acid (Ark Pharm, Inc., Cat. #: AK-29091), 2-propanamine and {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride. LCMS (M+H)⁺: m/z=493.2/495.2. ¹H NMR (400 MHz, DMSO-d₆): δ 12.65 (s, 1H), 9.09 (s, 1H), 8.85 (s, 1H), 8.56 (s, 1H), 7.86 (dd, J=8.0, 2.5 Hz, 1H), 7.78 (m, 1H), 7.52 (d, J=7.0 Hz, 1H), 7.23 (m, 1H), 6.64 (d, J=12.0 Hz, 1H), 4.77 (d, J=9.0 Hz, 2H), 4.51 (d, J=9.0 Hz, 2H), 3.75 (s, 2H), 4.00 (m, 1H), 1.12 (d, J=6.5 Hz, 6H).

Example 9. 5-{3-(Cyanomethyl)-3-[4-(7H-pyrrolo[2,3-d]pyrimidin-4-yl)-1H-pyrazol-1-yl]azetidin-1-yl}-N-isopropylpyridine-2-carboxamide

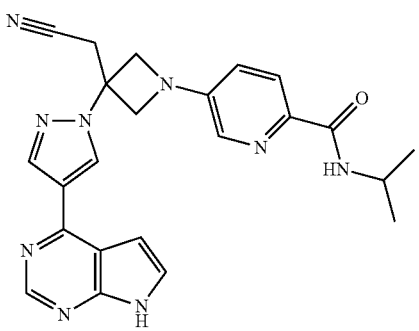 [SMILES: CC(C)NC(=O)c1ccc(N2CC(CC#N)(n3cc(-c4ncnc5[nH]ccc45)cn3)C2)cn1]

This compound was prepared by using procedures analogous to those described for the synthesis of Example 3, Step 1-3 starting from 5-bromopyridine-2-carboxylic acid, 2-propanamine and {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride. LCMS (M+H)⁺: m/z=442.2. ¹H NMR (400 MHz, DMSO-d₆): δ 12.82 (s, 1H), 9.12 (s, 1H), 8.88 (s, 1H), 8.59 (s, 1H), 8.12 (d, J=8.0 Hz, 1H), 7.94 (d, J=2.5 Hz, 1H), 7.86 (d, J=8.0 Hz, 1H), 7.83 (m, 1H), 7.28 (m, 1H), 7.10 (dd, J=8.0, 3.0 Hz, 1H), 4.66 (d, J=8.0 Hz, 2H), 4.41 (d, J=8.0 Hz, 2H), 3.78 (s, 2H), 4.05 (m, 1H), 1.16 (d, J=6.5 Hz, 6H).

Example 10. 4-{3-(Cyanomethyl)-3-[4-(7H-pyrrolo[2,3-d]pyrimidin-4-yl)-1H-pyrazol-1-yl]azetidin-1-yl}-3-fluoro-N-[(1S)-2,2,2-trifluoro-1-methylethyl]benzamide

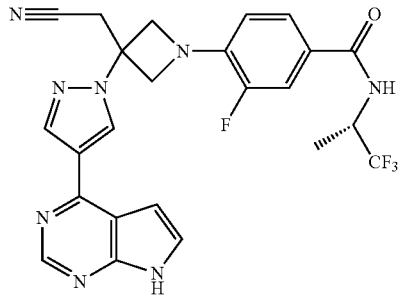 [SMILES: C[C@H](NC(=O)c1ccc(N2CC(CC#N)(n3cc(-c4ncnc5[nH]ccc45)cn3)C2)c(F)c1)C(F)(F)F]

Step 1: 4-bromo-3-fluoro-N-[(1S)-2,2,2-trifluoro-1-methylethyl]benzamide (2S)-1,1,1-Trifluoropropan-2-amine hydrochloride (0.068 g, 0.46 mmol) (ACS Scientific Inc., Cat. #2-01-6) was added to a mixture of 4-bromo-3-fluorobenzoic acid (0.100 g, 0.457 mmol) and N,N,N',N'-tetramethyl-O-(7-azabenzotriazol-1-yl)uronium hexafluorophosphate (0.26 g, 0.68 mmol) in methylene chloride (2.50 mL), followed by N,N-diisopropylethylamine (0.16 mL, 0.91 mmol). The reaction mixture was stirred at room temperature overnight. The reaction mixture was worked up with aqueous NaHCO₃, and extracted with methylene chloride (3×20 mL). The combined organic layers were washed with brine, dried over MgSO₄, filtered and concentrated under reduced pressure. The residue was purified by flash chromatography on a silica gel column with ethyl acetate in hexanes (0-20%) to afford the desired product. LCMS (M+H)⁺: m/z=314.0/316.0.

Step 2: 4-{3-(cyanomethyl)-3-[4-(7H-pyrrolo[2,3-d]pyrimidin-4-yl)-1H-pyrazol-1-yl]azetidin-1-yl}-3-fluoro-N-[(1S)-2,2,2-trifluoro-1-methylethyl]benzamide This compound was prepared as TFA salt by using procedures analogous to those described for the synthesis of Example 3, Step 2-3 starting from {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride and 4-bromo-3-fluoro-N-[(1S)-2,2,2-trifluoro-1-methylethyl]benzamide (from Step 1, above). LCMS (M+H)⁺: m/z=513.2.

¹H NMR (300 MHz, DMSO-d₆): δ 12.64 (s, 1H), 9.08 (s, 1H), 8.83 (s, 1H), 8.61 (d, J=8.5 Hz, 1H), 8.57 (s, 1H), 7.79

(m, 1H), 7.70 (s, 1H), 7.66 (m, 1H), 7.23 (d, J=2.3 Hz, 1H), 6.76 (t, J=8.5 Hz, 1H), 4.80 (m, 1H), 4.68 (d, J=8.0 Hz, 2H), 4.53 (d, J=8.0 Hz, 2H), 3.76 (s, 2H), 1.32 (d, J=7.0 Hz, 3H).

Example 11. 5-{3-(Cyanomethyl)-3-[4-(7H-pyrrolo[2,3-d]pyrimidin-4-yl)-1H-pyrazol-1-yl]azetidin-1-yl}-N-[(1S)-1-cyclopropylethyl]pyridine-2-carboxamide

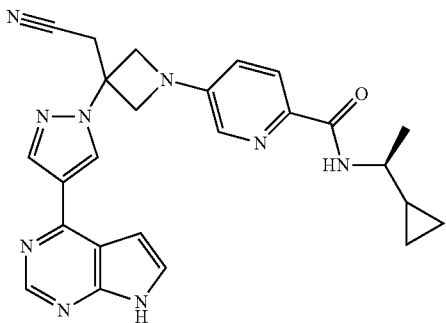 [SMILES: C[C@H](NC(=O)c1ccc(N2CC(CC#N)(n3cc(-c4ncnc5[nH]ccc45)cn3)C2)cn1)C1CC1]

This compound was prepared by using procedures analogous to those described for the synthesis of Example 3, Step 2-3 starting from 5-bromo-N-[(1S)-1-cyclopropylethyl]pyridine-2-carboxamide (Example 2, Step 1) and {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride. LCMS (M+H)$^+$: m/z=468.2.

$^1$H NMR (400 MHz, DMSO-d$_6$): δ 12.60 (s, 1H), 9.14 (s, 1H), 8.90 (s, 1H), 8.60 (s, 1H), 8.26 (d, J=8.0 Hz, 1H), 7.97 (d, J=3.0 Hz, 1H), 7.88 (d, J=8.0 Hz, 1H), 7.84 (m, 1H), 7.28 (m, 1H), 7.12 (dd, J=8.0, 3.0 Hz, 1H), 4.68 (d, J=8.0 Hz, 2H), 4.43 (d, J=8.0 Hz, 2H), 3.80 (s, 2H), 3.39 (m, 1H), 1.12 (t, J=7.0 Hz, 3H), 1.05 (m, 1H), 0.45 (m, 1H), 0.38 (m, 1H), 0.22 (m, 1H).

Example 12. 5-{3-(Cyanomethyl)-3-[4-(7H-pyrrolo[2,3-d]pyrimidin-4-yl)-1H-pyrazol-1-yl]azetidin-1-yl}-N-(3,3-difluorocyclobutyl)pyridine-2-carboxamide

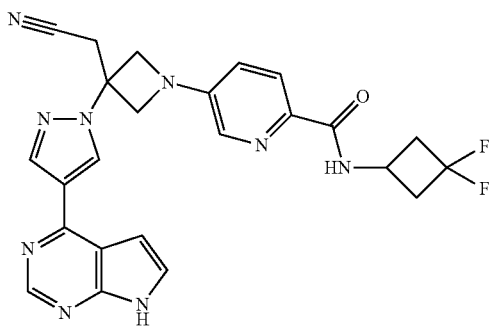 [SMILES: N#CCC1(n2cc(-c3ncnc4[nH]ccc34)cn2)CN(c2ccc(C(=O)NC3CC(F)(F)C3)nc2)C1]

Step 1: methyl 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}pyridine-2-carboxylate

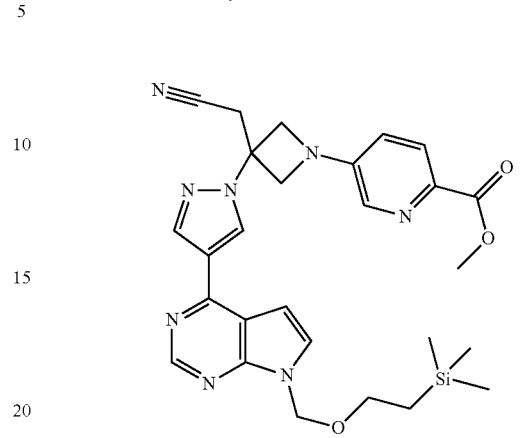

A mixture of 2,2'-bis(diphenylphosphino)-1,1'-binaphthyl (660 mg, 1.1 mmol), {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile hydrochloride (4.76 g, 10.7 mmol), methyl 5-bromopicolinate (3.00 g, 13.9 mmol), palladium acetate (240 mg, 1.1 mmol) and cesium carbonate (10 g, 32 mmol) in toluene (120 mL) was de-gassed and recharged with nitrogen for three times. The reaction mixture was stirred at 100° C. overnight. After cooling the reaction mixture was quenched with water, and extracted with ethyl acetate (3×50 mL). The combined organic layers were washed with brine, dried over MgSO$_4$, filtered and concentrated under reduced pressure. The residue was purified by flash chromatography on a silica gel column with MeOH in dichloromethylene (0-5%) to afford the desired product (3.70 g, 63.6%). LCMS (M+H)$^+$: m/z=545.3.

Step 2: 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}pyridine-2-carboxylic acid A mixture of lithium hydroxide monohydrate (0.87 g, 21 mmol) and methyl 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}pyridine-2-carboxylate (3.70 g, 6.79 mmol) in methanol (10.0 mL) and water (5.0 mL) was stirred at room temperature overnight. The mixture was adjusted to pH 3 with aqueous HCl (1.0 N), and concentrated under reduced pressure to remove methanol. The solid formed was filtered and washed with water, and dried under reduced pressure to afford the crude product. LCMS (M+H)$^+$: m/z=531.1.

Step 3: 5-{3-(cyanomethyl)-3-[4-(7H-pyrrolo[2,3-d]pyrimidin-4-yl)-1H-pyrazol-1-yl]azetidin-1-yl}-N-(3,3-difluorocyclobutyl)pyridine-2-carboxamide A mixture of benzotriazol-1-yloxytris(dimethylamino)phosphonium hexafluorophosphate (60.0 mg, 0.14 mmol), 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}pyridine-2-carboxylic acid (48.4 mg, 0.0913 mmol), 3,3-difluorocyclobutanamine hydrochloride (20. mg, 0.14 mmol, Molbridge: Cat.#MB00001399) and N,N-diisopropylethylamine (64 μL, 0.36 mmol) in methylene chloride (2 mL) was stirred at room temperature overnight. The reaction mixture was worked up with aqueous NaHCO$_3$, and extracted with dichloromethylene (2×2 mL). The combined organic layers were washed with water (1 mL), concentrated and dried under reduced pressure. The residue was dissolved in dichloromethylene (1 mL) and trifluoroacetic acid (0.5 mL). The mixture was stirred at room temperature for 1.5 hours, and concentrated under reduced pressure. The residue was dissolved in methanol (2.5 mL). Ethylenediamine (0.21 mL, 3.2 mmol) were added. The reaction mixture was stirred at room temperature for 2 hours, and purified by RP-HPLC (pH=10) to afford the desired product. LCMS (M+H)$^+$: m/z=490.1. $^1$H NMR (300 MHz, DMSO-d$_6$): δ 12.50 (br, 1H), 9.01 (s, 1H), 8.93 (d, J=7.8 Hz, 1H), 8.76 (s, 1H), 8.50 (s, 1H), 7.89 (d, J=2.7 Hz, 1H), 7.81 (d, J=8.6 Hz, 1H), 7.70 (dd, J=3.4, 2.5 Hz, 1H), 7.15 (dd, J=3.5, 1.5 Hz, 1H), 7.04 (dd, J=8.6, 2.8 Hz, 1H), 4.63 (d, J=9.0 Hz, 2H), 4.36 (d, J=8.9 Hz, 2H), 4.23 (m, 1H), 3.73 (s, 2H), 2.80 (m, 4H).

Example 13. 4-{3-(Cyanomethyl)-3-[4-(7H-pyrrolo[2,3-d]pyrimidin-4-yl)-1H-pyrazol-1-yl]azetidin-1-yl}-N-isopropylbenzamide

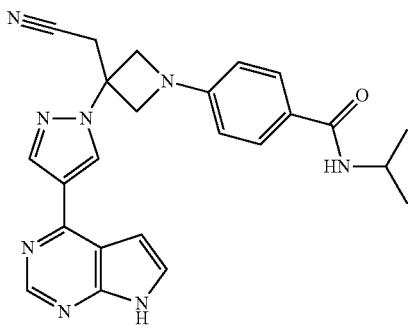 [SMILES: CC(C)NC(=O)c1ccc(N2CC(CC#N)(n3cc(-c4ncnc5[nH]ccc45)cn3)C2)cc1]

Step 1: 4-bromo-N-isopropylbenzamide

A solution of 4-bromobenzoic acid (4.00 g, 19.9 mmol, Aldrich: Cat.#108510) and thionyl chloride (10.0 mL, 137 mmol) was heated by microwave irradiation at 100° C. for 1 h, turning the heterogeneous solution to a homogeneous solution. The volatiles were removed in vacuo and the residue was azeotropically washed with dry acetonitrile several times (20 mL×4) to remove excess thionyl chloride. The residue was dissolved in anhydrous methylene chloride (40 mL) and cooled to 0° C. prior to the addition of 2-propanamine (8.0 mL, 94 mmol, 99.5% pure Aldrich [75-31-0]). After 1 hour, the reaction mixture was diluted with methylene chloride (20 mL) and quenched with H$_2$O (5 mL). The layers were separated and the organic layer was washed with H$_2$O (1×5 mL), saturated NaHCO$_3$ (1×5 mL), H$_2$O (1×5 mL), 1 N HCl (3×5 mL), H$_2$O (1×5 mL), and brine (5 mL). The organic layer was dried over Na$_2$SO$_4$, filtered, and concentrated in vacuo to afford the desired product (4.50 g, 93% yield) which was used directly in the next step without further purification. LCMS (M+H)$^+$: m/z=242/244.

Step 2: 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-isopropylbenzamide

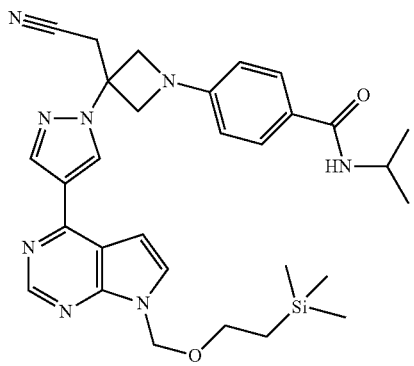 [SMILES: CC(C)NC(=O)c1ccc(N2CC(CC#N)(n3cc(-c4ncnc5c4ccn5COCC[Si](C)(C)C)cn3)C2)cc1]

A mixture of 4-bromo-N-isopropylbenzamide (1.82 g, 7.52 mmol), {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile hydrogen chloride (2.23 g, 5.00 mmol), palladium acetate (78 mg, 0.35 mmol, Aldrich [3375-31-3]), (9,9-dimethyl-9H-xanthene-4,5-diyl)bis(diphenylphosphine) (405 mg, 0.700 mmol, Aldrich [161265-03-8]), and cesium carbonate (3.03 g, 9.30 mmol) in toluene (22 mL) was de-gassed and purged several times with N$_2$ (g) prior to heating at 105° C. in a sealed vial for 2 days. Upon cooling to room temperature the reaction mixture was filtered through a pad of celite, concentrated in-vacuo and purified by flash chromatography on a silica gel column eluting with MeOH in methylene chloride (0-5%) to afford the desired product (1.74 g, 61% yield). LCMS (M+H)$^+$: m/z=571.3.

Step 3: 4-{3-(cyanomethyl)-3-[4-(7H-pyrrolo[2,3-d]pyrimidin-4-yl)-1H-pyrazol-1-yl]azetidin-1-yl}-N-isopropylbenzamide 4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-isopropylbenzamide (1.74 g, 3.05 mmol) was dissolved in methylene chloride (5.0 mL) and trifluoroacetic acid (5.0 mL, 26 mmol) and stirred at room temperature After 4 hours, LC/MS data indicated that the reaction was complete and the desired product was formed (LCMS (M+H)$^+$: m/z=471.3). The volatiles were removed in vacuo and the residue was azeotropically washed with acetonitrile several times (4×10 mL) to remove the excess TFA. The residue was dissolved in methanol (15 mL) and to this was added 14.8 M ammonium hydroxide in H$_2$O (3.0 mL, 44 mmol) and ethylenediamine (0.10 mL, 1.5 mmol) and the resulting solution was stirred at room temperature for 3 hours to afford the desired product. The product was further precipitated out as a white solid by the addition of H$_2$O (15 mL) and the heterogeneous solution was stirred for 30 minutes prior to pouring into water (60 mL). The precipitate was filtered off, washed with water (2×10 mL), and dried under high vacuum to afford the desired product (1.05 g, 78% yield). LCMS (M+H)$^+$: m/z=441.1. $^1$H NMR (400 MHz, CD$_3$OD): δ 8.78 (s, 1H), 8.66 (s, 1H), 8.42 (s, 1H), 7.99 (d, J=8.0 Hz, 1H), 7.75 (d, J=8.5 Hz, 2H), 7.50 (d, J=4.0 Hz, 1H), 7.00 (d, J=4.0 Hz, 1H), 6.64 (t, J=8.5 Hz, 2H), 4.55 (d, J=8.0 Hz, 2H), 4.40 (d, J=8.0 Hz, 2H), 4.19 (m, 1H), 3.62 (s, 2H), 1.22 (d, J=7.0 Hz, 6H).

Example 14. 4-{3-(Cyanomethyl)-3-[4-(7H-pyrrolo[2,3-d]pyrimidin-4-yl)-1H-pyrazol-1-yl]azetidin-1-yl}-2-fluoro-N-isopropylbenzamide

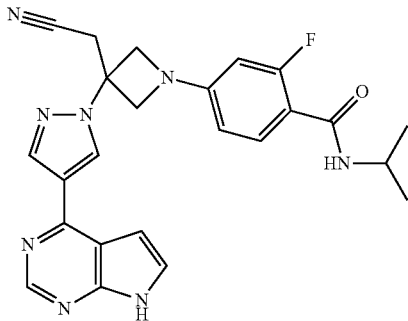 [SMILES: CC(C)NC(=O)c1ccc(N2CC(CC#N)(n3cc(-c4ncnc5[nH]ccc45)cn3)C2)cc1F]

Step 1: 4-bromo-2-fluoro-N-isopropylbenzamide

A solution of 4-bromo-2-fluorobenzoic acid (1.50 g, 6.85 mmol, Combi-Blocks: Cat.# CA-4096), N,N,N',N'-tetramethyl-O-(7-azabenzotriazol-1-yl)uronium hexafluorophosphate (2.86 g, 7.53 mmol), and N,N-diisopropylethylamine (2.4 mL, 14 mmol) in methylene chloride (20. mL) was stirred for 10 minutes. 2-Propanamine (2.3 mL, 27 mmol) was then added and stirring was continued for 1.5 hours LC/MS data indicated that the major reaction component was the desired product. The reaction mixture was diluted with methylene chloride (40 mL) and H₂O (3 mL). The layers were separated and the organic layer was washed with water (3×3 mL) and 1N HCl (3×3 mL). The combined aqueous phases were extracted with methylene chloride (5 mL). The combined organic layers were washed with brine (3 mL), dried over Na₂SO₄, filtered and concentrated in-vacuo. The crude product was purified by flash chromatography on a silica gel column eluting with ethyl acetate in hexanes (0-15%) to afford the desired product. LCMS (M+H)⁺: m/z=260.0/262.0.

Step 2: 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-2-fluoro-N-isopropylbenzamide

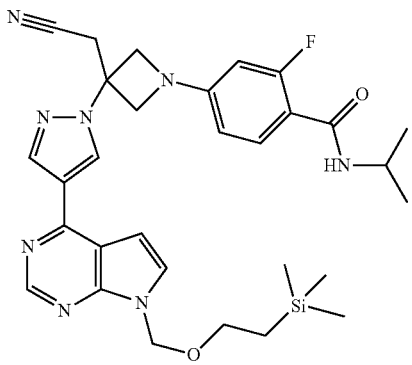 [SMILES: CC(C)NC(=O)c1ccc(N2CC(CC#N)(n3cc(-c4ncnc5c4ccn5COCC[Si](C)(C)C)cn3)C2)cc1F]

A mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile [1.0]-hydrogen chloride (1.71 g, 3.84 mmol), cesium carbonate (2.6 g, 8.1 mmol), palladium acetate (94 mg, 0.42 mmol), (9,9-dimethyl-9H-xanthene-4,5-diyl)bis(diphenylphosphine) (470 mg, 0.81 mmol), and 4-bromo-2-fluoro-N-isopropylbenzamide (1.00 g, 3.84 mmol) in toluene (20 mL, 200 mmol) was de-gassed, purged with N₂ (g) three times, and heated to 100° C. overnight. Upon cooling to room temperature, the crude reaction mixture was filtered through a pad of celite and the inorganics were washed with ethyl acetate (5×10 mL). The filtrate was concentrated in-vacuo and purified by flash chromatography on a silica gel column eluting with methanol in methylene chloride (0-5%) to afford the desired product (1.6 g, 70% yield). LCMS (M+H)⁺: m/z=589.3.

Step 3: 4-{3-(cyanomethyl)-3-[4-(7H-pyrrolo[2,3-d]pyrimidin-4-yl)-1H-pyrazol-1-yl]azetidin-1-yl}-2-fluoro-N-isopropylbenzamide 4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-2-fluoro-N-isopropylbenzamide (0.7 g, 1.19 mmol) was dissolved in methylene chloride (5.0 mL) and to this was added trifluoroacetic acid (5.0 mL) and the solution was stirred at room temperature for 1 hour. LC/MS data indicated that the main reaction component was the desired product (LCMS (M+H)⁺: m/z=489.2). The volatiles were removed in-vacuo and the residue was azeotropically washed with acetonitrile (3×10 mL). The resulting residue was dissolved in methanol (4 mL) followed by the addition of ethylenediamine (400 µL) and ammonium hydroxide (1.2 mL). After stirring at room temperature for 2 hours, LC/MS data indicated that the main reaction component was the desired product. The crude reaction mixture was purified by RP-HPLC (pH=2) to afford the desired product as TFA salt. LCMS (M+H)⁺: m/z=459.2. ¹H NMR (500 MHz, CD₃OD): δ 9.09 (s, 1H), 8.90 (s, 1H), 8.56 (s, 1H), 7.85 (d, J=3.7 Hz, 1H), 7.66 (t, J=8.5 Hz, 1H), 7.33 (d, J=3.8 Hz, 1H), 6.47 (dd, J=8.6, 2.2 Hz, 1H), 6.39 (dd, J=13.5, 2.2 Hz, 1H), 4.61 (d, J=8.8 Hz, 2H), 4.44 (d, J=8.8 Hz, 2H), 4.22-4.13 (m, 1H), 3.68 (s, 2H), 1.23 (d, J=6.6 Hz, 6H).

Example 15. 4-{3-(Cyanomethyl)-3-[4-(7H-pyrrolo[2,3-d]pyrimidin-4-yl)-1H-pyrazol-1-yl]azetidin-1-yl}-N-[(1S)-1-cyclohexylethyl]-2-fluorobenzamide

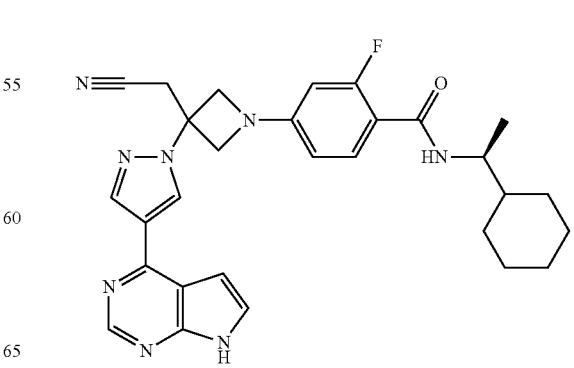

Step 1: Methyl 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-2-fluorobenzoate

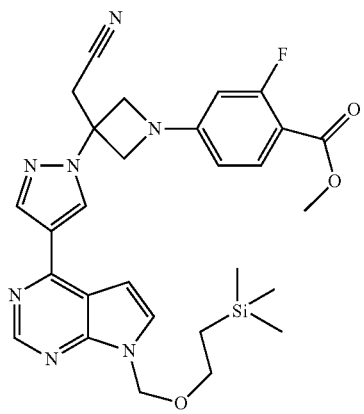 [SMILES: COC(=O)c1ccc(N2CC(CC#N)(n3cc(-c4ncnc5c4ccn5COCC[Si](C)(C)C)cn3)C2)cc1F]

A mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (1.8 g, 3.7 mmol), methyl 4-bromo-2-fluorobenzoate (1.00 g, 4.29 mmol) (Combi-Blocks: Cat.#CA-4291), cesium carbonate (3.6 g, 11 mmol), palladium acetate (0.10 g, 0.44 mmol), and 9,9-dimethyl-9H-xanthene-4,5-diyl)bis(diphenylphosphine (0.54 g, 0.93 mmol) in dry toluene (20 mL) was de-gassed and purged several times with nitrogen, and heated at 90° C. in a sealed vial for 14 hours with stirring. Upon cooling to room temperature, the reaction mixture was filtered through a pad of celite, concentrated in-vacuo and purified by flash chromatography on a silica gel column with hexanes-ethyl acetate to afford the desired product (1.72 g, 82% yield). LCMS (M+H)$^+$: m/z=562.2.

Step 2: 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-2-fluorobenzoic acid To a solution of methyl 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-2-fluorobenzoate (1.22 g, 2.17 mmol) in tetrahydrofuran (10 mL) was added a solution of lithium hydroxide (0.21 g, 8.8 mmol) in water (9.8 mL). The reaction mixture was then stirred at 35° C. for 24 hours. The reaction mixture was diluted with water (5 mL) and pH was adjusted to ~4 with 1 N HCl, extracted with ethyl acetate. The organic fraction was washed with water (1×), brine (1×), dried over anhydrous sodium sulfate, filtered and concentrated in vacuo. The solid was then triturated with methylene chloride-methanol (95:5), filtrated to afford the desired product (0.917 g, 77.1%). LCMS (M+H)$^+$: m/z=562.2.

Step 3: 4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[(1S)-1-cyclohexylethyl]-2-fluorobenzamide

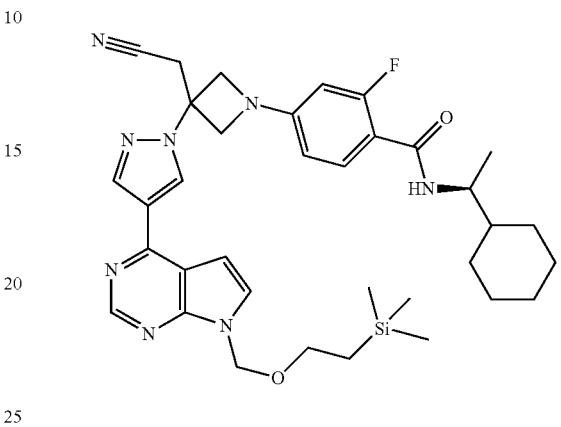

The 4-{3-(cyanomethyl)-3-[4-(7-{[2-(trimethylsilyl)ethoxy]methyl})-7H-pyrrolo[2,3-d]pyrimidin-4-yl)-1H-pyrazol-1-yl]azetidin-1-yl}-2-fluorobenzoic acid (0.015 g, 0.027 mmol), N,N,N',N'-tetramethyl-O-(7-azabenzotriazol-1-yl)uronium hexafluorophosphate (0.016 g, 0.042 mmol), and (1S)-1-cyclohexylethanamine (0.0080 mL, 0.055 mmol, Aldrich: Cat.#336513) in dry 1,2-dichloroethane (0.501 mL) (not all in solution) was stirred for 30 minutes at 60° C., then 14 hours at room temperature (all in solution). LC/MS data showed that the reaction was complete and the desired product was formed. The product was used as is without further purification. LCMS (M+H)$^+$: m/z=657.3.

Step 4: 4-{3-(cyanomethyl)-3-[4-(7H-pyrrolo[2,3-d]pyrimidin-4-yl)-1H-pyrazol-1-yl]azetidin-1-yl}-N-[(1S)-1-cyclohexylethyl]-2-fluorobenzamide To the above reaction mixture in 1,2-dichloroethane (0.5 mL) was added trifluoroacetic acid (0.200 mL) and stirred for 1.5 hours. The volatiles were removed in-vacuo and the residue was azeotropically washed with acetonitrile (3×). The resulting residue was redissolved in methanol (0.500 mL), added ethylenediamine (0.049 mL, 0.74 mmol) and was stirred for 40 minutes, concentrated under reduced pressure. The crude product was then purified by LC/MS (pH=2) to give the desired product as TFA salt (0.009 g, 40% yield). LCMS (M+H)$^+$: m/z=527.2. $^1$H NMR (500 MHz, DMSO-d$_6$): δ 12.36 (s, 1H), 8.98 (s, 1H), 8.76 (s, 1H), 8.50 (s, 1H), 7.71-7.65 (m, 1H), 7.51 (t, J=8.5 Hz, 1H), 7.48 (dd, J=8.5, 4.3 Hz, 1H), 7.14 (d, J=1.9 Hz, 1H), 6.43 (s, 1H), 6.41 (dd, J=4.8, 2.0 Hz, 1H), 4.57 (d, J=8.8 Hz, 2H), 4.31 (d, J=8.8 Hz, 2H), 3.84-3.76 (m, 1H), 3.75 (s, 2H), 1.77-1.65 (m, 4H), 1.60 (d, J=11.4 Hz, 1H), 1.44-1.30 (m, 1H), 1.23-1.08 (m, 3H), 1.06 (d, J=6.8 Hz, 3H), 0.88-0.99 (m, 2H).

Example 16. 4-{3-(Cyanomethyl)-3-[4-(7H-pyrrolo[2,3-d]pyrimidin-4-yl)-1H-pyrazol-1-yl]azetidin-1-yl}-3-fluoro-N-[(1R)-2,2,2-trifluoro-1-methylethyl]benzamide

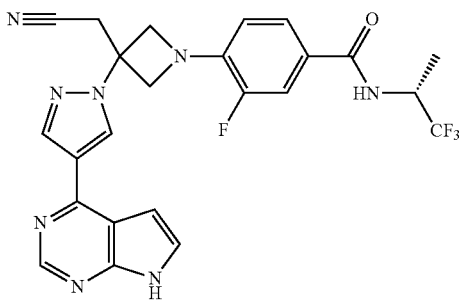 [SMILES: C[C@@H](NC(=O)c1ccc(N2CC(CC#N)(n3cc(-c4ncnc5[nH]ccc45)cn3)C2)c(F)c1)C(F)(F)F]

This compound was prepared by using procedures analogous to those described for the synthesis of Example 5, Step 3 starting from 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-3-fluorobenzoic acid and (2R)-1,1,1-trifluoropropan-2-amine hydrochloride. LCMS (M+H)$^+$: m/z=513.2. $^1$H NMR (400 MHz, DMSO-$d_6$): δ 12.66 (br, 1H), 9.11 (s, 1H), 8.86 (s, 1H), 8.64 (d, J=8.9 Hz, 1H), 8.58 (s, 1H), 7.80 (br, 1H), 7.71 (s, 1H), 7.69 (dd, J=4.0, 1.6 Hz, 1H), 7.26 (br, 1H), 6.78 (t, J=8.7 Hz, 1H), 4.89-4.78 (m, 1H), 4.71 (d, J=7.7 Hz, 2H), 4.45 (dd, J=9.4, 1.8 Hz, 2H), 3.78 (s, 2H), 1.35 (d, J=7.0 Hz, 3H).

Example 17. 5-{3-(Cyanomethyl)-3-[4-(7H-pyrrolo[2,3-d]pyrimidin-4-yl)-1H-pyrazol-1-yl]azetidin-1-yl}-N-[1-(trifluoromethyl)cyclopropyl]pyridine-2-carboxamide

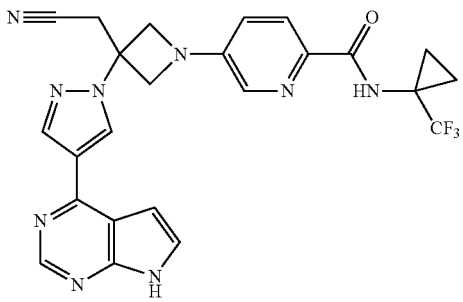 [SMILES: N#CCC1(n2cc(-c3ncnc4[nH]ccc34)cn2)CN(c2ccc(C(=O)NC3(C(F)(F)F)CC3)nc2)C1]

This compound was prepared by using procedures analogous to those described for the synthesis of Example 12, Step 3 starting from 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}pyridine-2-carboxylic acid (Example 12, Step 2) and 1-(trifluoromethyl)cyclopropanamine (Oakwood Products, Inc., Cat. #: 038175). LCMS (M+H)$^+$: m/z=508.2. $^1$H NMR (400 MHz, DMSO-$d_6$): δ 12.69 (br, 1H), 9.12 (s, 1H), 9.11 (d, J=2.9 Hz, 1H), 8.87 (s, 1H), 8.59 (s, 1H), 7.95 (d, =2.7 Hz, 1H), 7.89 (d, J=8.6 Hz, 1H), 7.84-7.80 (br, 1H), 7.26 (dd, J=2.1, 1.3 Hz, 1H), 7.11 (dd, J=8.7, 2.8 Hz, 1H), 4.70 (d, J=9.1 Hz, 2H), 4.44 (d, J=9.2 Hz, 2H), 3.80 (s, 2H), 1.28 (m, 2H), 1.17 (m, 2H).

Example 18. 5-{3-(Cyanomethyl)-3-[4-(7H-pyrrolo[2,3-d]pyrimidin-4-yl)-1H-pyrazol-1-yl]azetidin-1-yl}-N-isopropylpyrazine-2-carboxamide

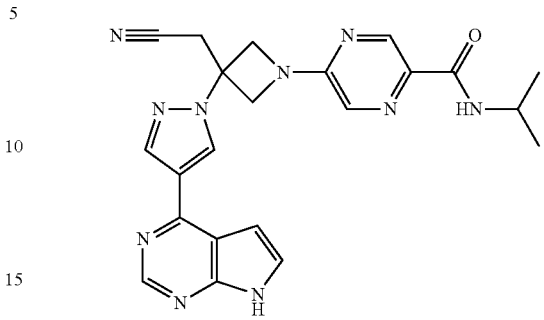

Step 1: methyl 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}pyrazine-2-carboxylate

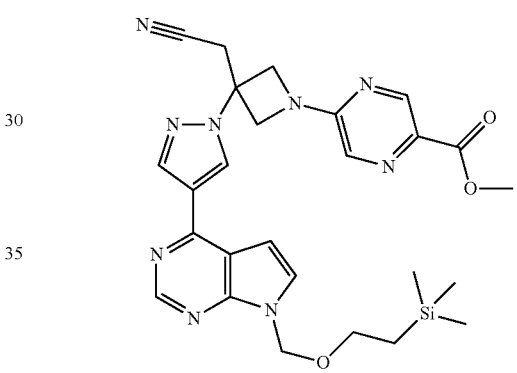

(R)-(+)-2,2'-Bis(diphenylphosphino)-1,1'-binaphthyl (0.065 g, 0.10 mmol) was added to a mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (0.50 g, 1.0 mmol), methyl 5-chloropyrazine-2-carboxylate (0.18 g, 1.0 mmol)(Ark Pharm, Inc., Cat. #: AK-23920), and cesium carbonate (1.0 g, 3.1 mmol) in toluene (15.0 mL) under nitrogen, followed by palladium acetate (0.023 g, 0.10 mmol). The reaction mixture was stirred at 120° C. for 3 h. After cooled to r.t., the reaction mixture was filtered through a pad of celite, washed with ethyl acetate. The filtrate was concentrated under reduced pressure. The residue was purified by flash chromatography on a silica gel column with ethyl acetate in dichloromethane (0-70%) to afford the desired product (0.31 g, 55%). LCMS (M+H)$^+$: m/z=546.3.

Step 2: 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}pyrazine-2-carboxylic acid A mixture of methyl 5-{3-(cyanomethyl)-3-[4-(7-{[2-(trimethylsilyl)ethoxy]-methyl}-7H-pyrrolo[2,3-d]pyrimidin-4-yl)-1H-pyrazol-1-yl]azetidin-1-yl}pyrazine-2-carboxylate (0.31 g, 0.57 mmol), lithium hydroxide monohydrate (0.060 g, 1.4 mmol) in methanol (6.0 mL) and water (2.5 mL) was stirred at 30° C. overnight. The mixture was adjusted to pH=4 with aqueous HCl, and concentrated under reduced pressure to remove MeOH. The resulted solid was filtered, washed with water and ether, and then dried in vacuum to afford the desired product (0.25 g, 83%). LCMS (M+H)$^+$: m/z=532.3

Step 3: 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide Triethylamine (15 μL, 0.11 mmol) was added to a mixture of 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}pyrazine-2-carboxylic acid (19.4 mg, 0.0365 mmol) and benzotriazol-1-yloxytris(dimethylamino)phosphonium hexafluorophosphate (19 mg, 0.044 mmol) and 2-propanamine (3.2 mg, 0.055 mmol) in methylene chloride (1.3 mL). The reaction mixture was stirred at r.t. overnight. The reaction mixture was worked up with aqueous NaHCO$_3$, and extracted with methylene chloride (2×2 mL). The combined organic layers were washed with water (1 mL) and concentrated under reduced pressure. The residue was used for next step without further purification. LCMS (M+H)$^+$: m/z=573.3.

Methylene chloride (1.3 mL) and trifluoroacetic Acid (0.6 mL) were added to the above intermediate. The reaction mixture was stirred at r.t. for 1.5 h. The mixture was concentrated under reduced pressure. The residue was dissolved in methanol (1.3 mL). To the solution was added ethylenediamine (0.086 mL). The reaction mixture was stirred at r.t. for 2 h., and purified by RP-HPLC (pH=10) to afford the desired product. LCMS (M+H)$^+$: m/z=443.2. $^1$H NMR (400 MHz, DMSO-d$_6$): δ 12.15 (br, 1H), 8.97 (s, 1H), 8.68 (s, 1H), 8.63 (d, J=1.2 Hz, 1H), 8.46 (s, 1H), 8.12 (d, =8.4 Hz, 1H), 7.97 (d, J=1.2 Hz, 1H), 7.60 (dd, J=3.3, 2.4 Hz, 1H), 7.07 (dd, J=3.4, 1.7 Hz, 1H), 4.81 (d, J=9.8 Hz, 2H), 4.53 (d, J=9.6 Hz, 2H), 4.13-4.02 (m, 1H), 3.78 (s, 2H), 1.14 (d, J=6.8 Hz, 6H).

Example 19. 4-{3-(Cyanomethyl)-3-[4-(7H-pyrrolo[2,3-d]pyrimidin-4-yl)-1H-pyrazol-1-yl]azetidin-1-yl}-N-[(1S)-2,2,2-trifluoro-1-methylethyl]benzamide bis(trifluoroacetate)

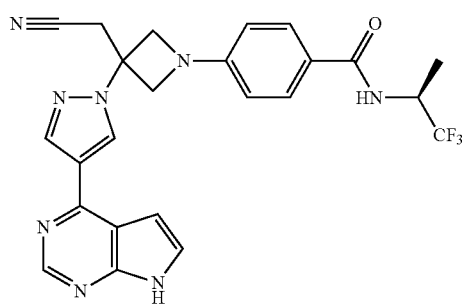 [SMILES: C[C@H](NC(=O)c1ccc(N2CC(CC#N)(n3cc(-c4ncnc5[nH]ccc45)cn3)C2)cc1)C(F)(F)F]

Step 1: methyl 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}benzoate

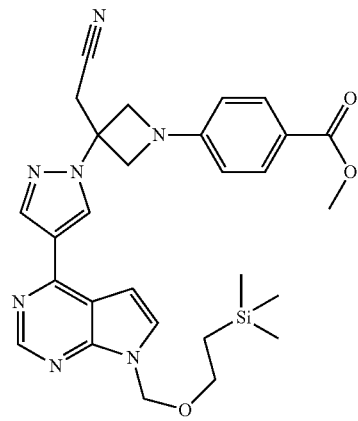 [SMILES: COC(=O)c1ccc(N2CC(CC#N)(n3cc(-c4ncnc5c4ccn5COCC[Si](C)(C)C)cn3)C2)cc1]

A mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (0.250 g, 0.518 mmol), methyl 4-bromobenzoate (0.13 g, 0.60 mmol, Aldrich: Cat.#407593), cesium carbonate (0.39 g, 1.2 mmol), palladium acetate (0.014 g, 0.060 mmol), 9,9-dimethyl-9H-xanthene-4,5-diyl)bis(diphenylphosphine) (0.070 g, 0.12 mmol) in dry toluene (3 mL) was de-gassed and purged several times with nitrogen, and heated at 100° C. in a sealed tube for 14 hours with stirring. Upon cooling to room temperature the reaction mixture was filtered through a pad of celite. The filtrate was washed with water (1×), brine (1×), dried over sodium sulfate, filtered and concentrated in vacuo. The crude product was purified by flash chromatography on a silica gel column with ethyl acetate in hexane to afford the desired product (0.240 g, 87%). LCMS (M+H)$^+$: m/z=544.2.

Step 2: 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}benzoic acid To a solution of methyl 4-{3-(cyanomethyl)-3-[4-(7-{[2-(trimethylsilyl)-ethoxy]methyl}-7H-pyrrolo[2,3-d]pyrimidin-4-yl)-1H-pyrazol-1-yl]azetidin-1-yl}benzoate (0.9 g, 2 mmol) in tetrahydrofuran (8 mL) was added a solution of lithium hydroxide (0.16 g, 6.7 mmol) in water (7.4 mL). The reaction mixture was then stirred at 35° C. The progress of reaction was monitored by LC/MS. After 46 hours, LC/MS data indicated that the main component of the reaction was the desired product LCMS m/z=530.2. The reaction mixture was diluted with water (5 mL), pH was adjusted to ~4 with 1N HCl, and was extracted with ethyl acetate. Organic fraction was then washed water (1×), brine (1×), dried over sodium sulfate and then concentrated in-vacuo. The crude product was purified by flash chromatography on a silica gel column with methanol in methylene chloride to give the desired product (0.450 g, 50%). LCMS (M+H)$^+$: m/z=530.2.

Step 3: 4-{3-(cyanomethyl)-3-[4-(7H-pyrrolo[2,3-d]pyrimidin-4-yl)-1H-pyrazol-1-yl]azetidin-1-yl}-N-[(1S)-2,2,2-trifluoro-1-methylethyl)]benzamide A mixture of 4-{3-(cyanomethyl)-3-[4-(7-{[2-(trimethylsilyl)ethoxy]methyl}-7H-pyrrolo[2,3-d]pyrimidin-4-yl)-

1H-pyrazol-1-yl]azetidin-1-yl}benzoic acid (0.100 g, 0.189 mmol), N,N,N',N'-tetramethyl-O-(7-azabenzotriazol-1-yl) uronium hexafluorophosphate (0.11 g, 0.29 mmol), (2S)-1,1,1-trifluoropropan-2-amine hydrochloride (0.042 g, 0.28 mmol) (ACS Scientific Inc., Cat. #2-01-6) and N,N-diisopropylethylamine (0.13 mL, 0.76 mmol) in anhydrous 1,2-dichloroethane (3 mL) was heated at 60° C. for 15 minutes to dissolve all of the reagents and then stirred at ambient temperature overnight. The volatiles were removed in vacuo and the residue was partitioned between water and ethyl acetate. The organic fraction was washed with brine, dried over sodium sulfate, filtered, and concentrated. The crude product was purified by flash chromatography on a silica gel column with ethyl acetate in hexane (0-60%) to afford the desired intermediate (0.080 g). The intermediate was dissolved in dichloromethane (3 mL) and to this was added trifluoroacetic acid (1.3 mL). After stirring at ambient temperature for 1.5 h., the volatiles were removed in vacuo. The residue was dissolved in methanol (1.6 mL) followed by the addition of ethylenediamine (0.2 mL, 4 mmol). After stirring at ambient temperature for 1 hour, the volatiles were removed in vacuo and the crude product was purified by RP-HPLC (pH=2) to afford the desired product (0.034 g) as TFA salt. LCMS (M+H)⁺: m/z=495.2. ¹H NMR (500 MHz, DMSO-d₆) δ 12.47 (bs, 1H), 9.00 (s, 1H), 8.77 (s, 1H), 8.50 (s, 1H), 8.48 (d, J=8.5 Hz, 1H), 7.81 (d, J=8.8 Hz, 2H), 7.67 (m, 1H), 7.15 (m, 1H), 6.61 (d, J=8.8 Hz, 2H), 4.82 (m, 1H), 4.59 (d, J=8.5 Hz, 2H), 4.33 (d, J=8.5 Hz, 2H), 3.76 (s, 2H), 1.33 (d, J=7.0 Hz, 3H).

Example 20. 4-{3-(Cyanomethyl)-3-[4-(7H-pyrrolo[2,3-d]pyrimidin-4-yl)-1H-pyrazol-1-yl]azetidin-1-yl}-N-[1-(1-methylpiperidin-4-yl)ethyl]benzamide

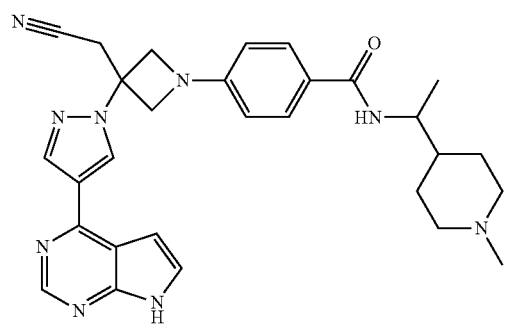 [SMILES: CC(NC(=O)c1ccc(N2CC(CC#N)(n3cc(-c4ncnc5[nH]ccc45)cn3)C2)cc1)C1CCN(C)CC1]

This compound was prepared as TFA salt by using procedures analogous to those described for the synthesis of Example 19, Step 3 started from 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}benzoic acid and 1-(1-methylpiperidin-4-yl)ethanamine (ChemBridge: Cat.#4019769). LCMS (M+H)⁺: m/z=524.3.

Example 21. 4-{3-(Cyanomethyl)-3-[4-(7H-pyrrolo[2,3-d]pyrimidin-4-yl)-1H-pyrazol-1-yl]azetidin-1-yl}-N-[(1R)-1-cyclopropylethyl]-2,5-difluorobenzamide

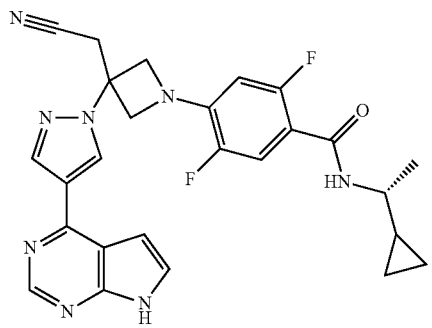 [SMILES: C[C@@H](NC(=O)c1cc(F)c(N2CC(CC#N)(n3cc(-c4ncnc5[nH]ccc45)cn3)C2)cc1F)C1CC1]

Step 1: 4-chloro-N-[(1R)-1-cyclopropylethyl]-2,5-difluorobenzamide

Oxalyl chloride (250.0 μL, 2.954 mmol) was added to a solution of 4-chloro-2,5-difluorobenzoic acid (0.0578 g, 0.300 mmol) in dichloromethylene (3 mL), followed by 15 μL of DMF. The mixture was stirred at room temperature for 1 hour. The volatiles were removed under reduced pressure. The residue was diluted with dichloromethylene (5 mL). To the solution was added potassium carbonate (82.9 mg, 0.600 mmol) in water (1 mL), and (1R)-1-cyclopropylethanamine (41.6 μL, 0.450 mmol). The mixture was stirred at room temperature for 30 minutes, and diluted with DCM, washed with water and brine. The organic layer was dried over MgSO₄, filtered and concentrated under reduced pressure to afford the desired product (0.075 g, 96%) which was directly used in the next step reaction without further purification. LCMS (M+H)⁺: m/z=260.0.

Step 2: 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[(1R)-1-cyclopropylethyl]-2,5-difluorobenzamide

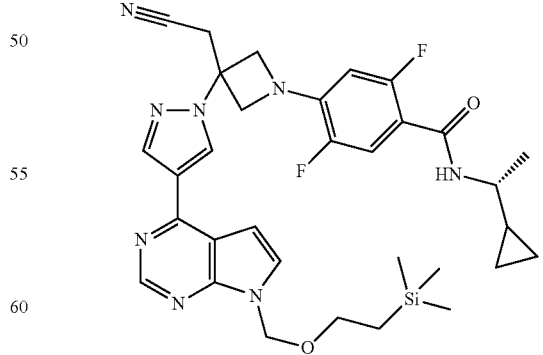

A mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (1.0 g, 2.1 mmol), 4-chloro-N-[(1R)-1-cyclopropylethyl]-2,5-difluorobenzamide (0.54 g, 2.1 mmol), cesium carbonate (2.0 g, 6.2 mmol), (R)-(+)-2,2'-bis(diphenylphosphino)-1,1'-binaphthyl (0.13 g, 0.21 mmol) and palladium acetate (0.046 g, 0.21 mmol) in toluene (20 mL, 200 mmol) was stirred at 105° C. overnight. After the reaction mixture was cooled to room temperature, the solid was filtered off by celite, washed with ethyl acetate. The filtrate was concentrated. The residue was purified by flash chromatography on a silica gel column with ethyl acetate in dichloromethylene (0-60%) to afford the desired product (0.48 g, 36%). LCMS (M+H)+: m/z=633.3.

Step 3: 4-{3-(cyanomethyl)-3-[4-(7H-pyrrolo[2,3-d]pyrimidin-4-yl)-1H-pyrazol-1-yl]azetidin-1-yl}-N-[(1R)-1-cyclopropylethyl]-2,5-difluorobenzamide 4-{3-(Cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[(1R)-1-cyclopropylethyl]-2,5-difluorobenzamide (0.48 g) was dissolved in a solution of trifluoroacetic acid (3 mL, 40 mmol) in methylene chloride (3 mL). The solution was stirred at room temperature for 1.5 hours. It was concentrated under reduced pressure. The residue was dissolved in methanol (5 mL). To the solution was added ethylenediamine (3 mL). The mixture was stirred at room temperature for 2 hours. After concentration the crude material was purified by flash chromatography on a silica gel column with methanol in dichloromethylene (0-10%) to afford the desired product (245 mg, 24%). LCMS (M+H)+: m/z=503.2. $^1$H NMR (400 MHz, DMSO-$d_6$): δ 12.60 (s, 1H), 9.08 (s, 1H), 8.85 (s, 1H), 8.57 (s, 1H), 7.84 (dd, J=8.0, 4.0 Hz, 1H), 7.78 (m, 1H), 7.36 (dd, J=13.0, 7.0 Hz, 1H), 7.23 (m, 1H), 6.64 (dd, J=13.0, 7.0 Hz, 1H), 4.70 (d, J=8.0 Hz, 2H), 4.45 (d, J=8.0 Hz, 2H), 3.78 (s, 2H), 3.43 (m, 1H), 1.09 (d, J=6.5 Hz, 6H), 0.97 (m, 1H), 0.43 (m, 1H), 0.37 (m, 1H), 0.28 (m, 1H), 0.19 (m, 1H).

Example 22. 4-{3-(Cyanomethyl)-3-[4-(7H-pyrrolo[2,3-d]pyrimidin-4-yl)-1H-pyrazol-1-yl]azetidin-1-yl}-2-fluoro-N-[(1S)-2,2,2-trifluoro-1-methylethyl]benzamide

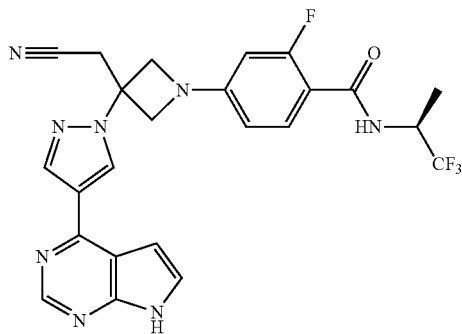 [SMILES: C[C@H](NC(=O)c1ccc(N2CC(CC#N)(n3cc(-c4ncnc5[nH]ccc45)cn3)C2)cc1F)C(F)(F)F]

To a solution of 4-{3-(cyanomethyl)-3-[4-(7-{[2-(trimethylsilyl)ethoxy]methyl})-7H-pyrrolo[2,3-d]pyrimidin-4-yl)-1H-pyrazol-1-yl]azetidin-1-yl}-2-fluorobenzoic acid (25 mg, 0.046 mmol) (Example 15, Step 2) and N,N-diisopropylethylamine (24 μL, 0.14 mmol) in 1,2-dichloroethane (0.5 mL) was added sequentially N,N,N',N'-tetramethyl-O-(7-azabenzotriazol-1-yl)uronium hexafluorophosphate (26 mg, 0.068 mmol) and (2S)-1,1,1-trifluoropropan-2-amine (12 mg, 0.11 mmol). After stirring at ambient temperature for 1.5 h, trifluoroacetic acid (0.5 mL) was added to the reaction mixture and stirring was continued for 1 h. The volatiles were removed in-vacuo and the residue was azeotropically washed with acetonitrile (3×3 mL). The resulting residue was dissolved in methanol (1 mL) and to this was added ammonium hydroxide (0.1 mL) and ethylenediamine (0.020 mL) and the reaction mixture was stirred at ambient temperature for 1 hour. The crude reaction mixture was subjected to RP-HPLC to afford the desired product. LCMS (M+H)+: m/z=513.1. $^1$H NMR (500 MHz, DMSO-$d_6$): δ 12.64 (s, 1H), 9.06 (s, 1H), 8.85 (s, 1H), 8.56 (s, 1H), 8.33 (dd, J=8.9, 1.8 Hz, 1H), 7.79 (s, 1H), 7.52 (t, J=8.5 Hz, 1H), 7.23 (s, 1H), 6.47 (s, 1H), 6.45-6.42 (m, 1H), 4.83-4.75 (m, 1H), 4.59 (dd, J=8.9, 1.7 Hz, 2H), 4.34 (d, J=8.9 Hz, 2H), 3.77 (s, 2H), 1.31 (d, J=7.1 Hz, 3H).

Example 23. 4-{3-(Cyanomethyl)-3-[4-(7H-pyrrolo[2,3-d]pyrimidin-4-yl)-1H-pyrazol-1-yl]azetidin-1-yl}-N-[(1R)-2,2,2-trifluoro-1-methylethyl]benzamide bis(trifluoroacetate)

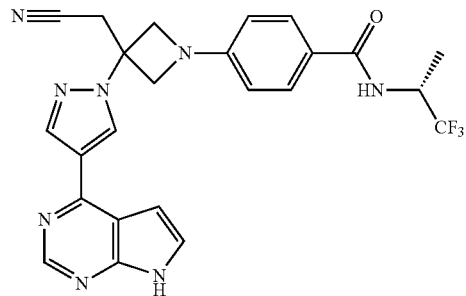 [SMILES: C[C@@H](NC(=O)c1ccc(N2CC(CC#N)(n3cc(-c4ncnc5[nH]ccc45)cn3)C2)cc1)C(F)(F)F]

A mixture of 4-{3-(cyanomethyl)-3-[4-(7-{[2-(trimethylsilyl)ethoxy]methyl)}-7H-pyrrolo[2,3-d]pyrimidin-4-yl)-1H-pyrazol-1-yl]azetidin-1-yl}benzoic acid (0.100 g, 0.189 mmol) (Example 19, Step 2), N,N,N',N'-tetramethyl-O-(7-azabenzotriazol-1-yl)uronium hexafluorophosphate (0.11 g, 0.29 mmol), (2R)-1,1,1-trifluoropropan-2-amine (0.043 g, 0.38 mmol) (SynQuest, catalog # PN 3130-7-R1), and N,N-diisopropylethylamine (0.13 mL, 0.75 mmol) in anhydrous 1,2-dichloroethane (3.35 mL) was stirred for 30 minutes at 55° C. to dissolve the reagents. After the solution became homogeneous, the reaction was allowed to stir at ambient temperature overnight. The reaction mixture was partitioned between water and ethyl acetate. The organic fraction was washed with water, brine, dried over sodium sulfate, filtered, and concentrated in-vacuo. The residue was dissolved in methylene chloride (2.6 mL) and to this was added trifluoroacetic acid (1.3 mL) and the resulting solution was stirred for 1.5 h. The volatiles were removed in-vacuo and the residue was dissolved in methanol (3.2 mL) followed by the addition of ethylenediamine (0.4 mL). After stirring at ambient temperature for 1 h., the volatiles were removed in-vacuo. The residue was purified by RP-HPLC (pH=2) to afford the desired product (0.080 g) as TFA salt. LCMS (M+H)+: m/z=495.2. $^1$H NMR (500 MHz, DMSO-$d_6$) δ 12.5 (bs, 1H), 9.05 (s, 1H), 8.83 (s, 1H), 8.55 (s, 1H), 8.49 (d, J=8.8 Hz, 1H), 7.82 (d, J=8.8 Hz, 2H), 7.75 (s, 1H), 7.21 (s, 1H), 6.62 (d, J=8.8 Hz, 2H), 4.7-4.9 (m, 1H), 4.58 (d, J=8.7 Hz, 2H), 4.34 (d, J=8.7 Hz, 2H), 3.77 (s, 2H), 1.33 (d, J=7.1 Hz, 3H).

Example 24. 5-{3-(Cyanomethyl)-3-[4-(7H-pyrrolo[2,3-d]pyrimidin-4-yl)-1H-pyrazol-1-yl]azetidin-1-yl}-N-ethylpyridine-2-carboxamide

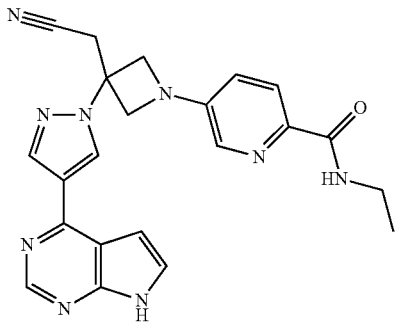 [SMILES: CCNC(=O)c1ccc(N2CC(CC#N)(n3cc(-c4ncnc5[nH]ccc45)cn3)C2)cn1]

This compound was prepared by using procedures analogous to those described for the synthesis of Example 3, Step 1-3 starting from 5-bromopyridine-2-carboxylic acid, ethylamine (2.0 M in tetrahedrofuran solution) and {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride. LCMS (M+H)$^+$: m/z=428.2.

Example 25. 4-{3-(Cyanomethyl)-3-[4-(7H-pyrrolo[2,3-d]pyrimidin-4-yl)-1H-pyrazol-1-yl]azetidin-1-yl}-N-[(1R)-1-methylpropyl]benzamide bis(trifluoroacetate)

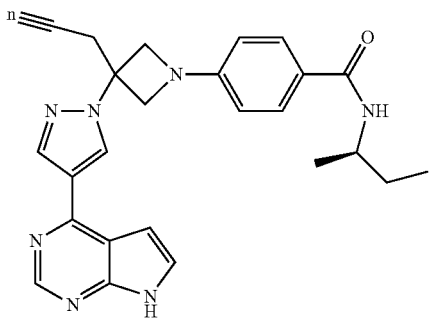

This compound was prepared as TFA salt by using procedures analogous to those described for the synthesis of Example 19, Step 3 started from 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}benzoic acid and (2R)-butan-2-amine (Aldrich: Cat.#296651). LCMS (M+H)$^+$: m/z=455.2. $^1$H NMR (500 MHz, DMSO-d$_6$) δ 12.36 (s, 1H), 8.99 (s, 1H), 8.76 (s, 1H), 8.50 (s, 1H), 7.81 (d, J=8.2 Hz, 1H), 7.76 (d, J=8.7 Hz, 2H), 7.68 (dd, J=3.3, 2.5 Hz, 1H), 7.14 (dd, J=3.4, 1.5 Hz, 1H), 6.59 (d, J=8.7 Hz, 2H), 4.55 (s, 2H), 4.30 (d, J=8.6 Hz, 2H), 3.89 (m, 1H), 3.75 (s, 2H), 1.58-1.39 (m, 2H), 1.10 (d, J=6.6 Hz, 3H), 0.84 (t, J=7.4 Hz, 3H).

Example 26. 4-{3-(Cyanomethyl)-3-[4-(7H-pyrrolo[2,3-d]pyrimidin-4-yl)-1H-pyrazol-1-yl]azetidin-1-yl}-N-(2,2,2-trifluoro-1-methylethyl)benzamide

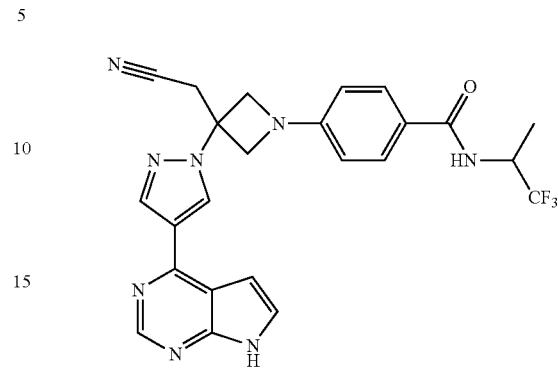

This compound was prepared as TFA salt by using procedures analogous to those described for the synthesis of Example 19, Step 3 started from 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}benzoic acid and 1-methyl-2,2,2-trifluoroethylamine hydrochloride (SynQuest Labs: Cat.#93130-7-08). LCMS (M+H)$^+$: m/z=495.2.

Example 27. 4-{3-(Cyanomethyl)-3-[4-(1H-pyrrolo[2,3-b]pyridin-4-yl)-1H-pyrazol-1-yl]azetidin-1-yl}-3-fluoro-N-isopropylbenzamide

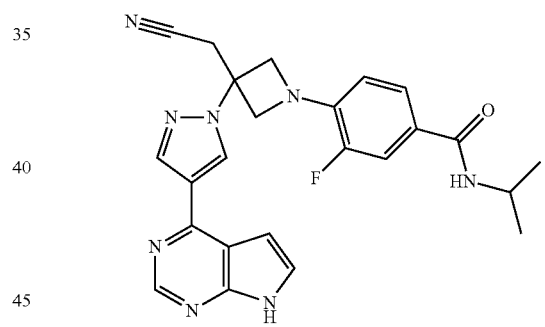

Step 1: tert-butyl 3-(cyanomethyl)-3-[4-(1H-pyrrolo[2,3-b]pyridin-4-yl)-1H-pyrazol-1-yl]azetidine-1-carboxylate A mixture of 4-bromo-1H-pyrrolo[2,3-b]pyridine (1.1 g, 5.7 mmol), tert-butyl 3-(cyanomethyl)-3-[4-(4,4,5,5-tetramethyl-1,3,2-dioxaborolan-2-yl)-1H-pyrazol-1-yl]azetidine-1-carboxylate (2.00 g, 5.15 mmol) (Example 40, Step 1), tetrakis(triphenylphosphine)palladium(0) (0.30 g, 0.26 mmol) and sodium carbonate (1.64 g, 15.4 mmol) in 1,4-dioxane (100 mL) and water (50 mL) under N$_2$(g) was stirred at 100° C. overnight. The reaction mixture was extracted with ethyl acetate (3×20 mL). The combined organic layers were washed with brine, dried over MgSO$_4$, filtered and concentrated under reduced pressure until 5 mL of solvent was left. The resulting precipitate (0.90 g) was collected by filtration and washed with ether. The filtrate was further concentrated under reduced pressure to a volume of about 3 mL. The precipitate formed was filtered, and washed with ether to afford additional product (0.50 g). The filtrate was concentrated under reduced pressure again. The residue was purified by flash chromatography on a silica gel column with methanol in dichloromethane (0-5%) to afford additional desired product (0.55 g). Total amount of product was 1.95 g (yield: 92.3%). LCMS (M+H)$^+$: m/z=379.1.

Step 2: {3-[4-(1H-pyrrolo[2,3-b]pyridin-4-yl)-1H-pyrazol-1-yl]azetidin-3-yl}acetonitrile Trifluoroacetic acid (7.0 mL) was added to tert-butyl 3-(cyanomethyl)-3-[4-(1H-pyrrolo[2,3-b]pyridin-4-yl)-1H-pyrazol-1-yl]azetidine-1-carboxylate (0.90 g, 2.4 mmol) in methylene chloride (7.0 mL). The reaction mixture was stirred at 30° C. for 2 h. The volatiles were removed under reduced pressure to afford the desired product (quantitative) as TFA salt which was directly used in the next step reaction without further purification. LCMS (M+H)$^+$: m/z=279.1.

Step 3: methyl 4-{3-(cyanomethyl)-3-[4-(1H-pyrrolo[2,3-b]pyridin-4-yl)-1H-pyrazol-1-yl]azetidin-1-yl}-3-fluorobenzoate N,N-Diisopropylethylamine (1.6 mL, 9.5 mmol) was added to {3-[4-(1H-pyrrolo[2,3-b]pyridin-4-yl)-1H-pyrazol-1-yl]azetidin-3-yl}acetonitrile TFA salt (2.4 mmol) and methyl 3,4-difluorobenzoate (0.41 g, 2.4 mmol) (Aldrich, Cat.#: 594717) in N-methylpyrrolidinone (NMP) (5.0 mL). The reaction mixture was stirred at 130° C. overnight. The reaction mixture was worked up with saturated aqueous NaHCO$_3$, extracted with ethyl acetate (3×20 mL). The combined organic layers were washed with brine, dried over MgSO$_4$, filtered and concentrated under reduced pressure. The residue was purified by flash chromatography on a silica gel column with methanol in dichloromethane (0-5%) to afford the desired product (0.34 g, 33%). LCMS (M+H)$^+$: m/z=431.1.

Step 4: 4-{3-(cyanomethyl)-3-[4-(1H-pyrrolo[2,3-b]pyridin-4-yl)-1H-pyrazol-1-yl]azetidin-1-yl}-3-fluorobenzoic acid Lithium hydroxide monohydrate (83 mg, 2.0 mmol) was added to a mixture of methyl 4-{3-(cyanomethyl)-3-[4-(1H-pyrrolo[2,3-b]pyridin-4-yl)-1H-pyrazol-1-yl]azetidin-1-yl}-3-fluorobenzoate (0.34 g, 0.79 mmol) in methanol (2.0 mL), water (1.0 mL) and THF (2.0 mL). The reaction mixture was stirred at 35° C. overnight, and adjusted to pH=5 with 1.0 N HCl aqueous solution, and concentrated under reduced pressure to remove methanol and THF. The precipitate formed was filtered, washed with water and ether, and dried in vacuum to afford the desired product (0.17 g, 52%) which was directly used in the next step reaction without further purification. LCMS (M+H)$^+$: m/z=417.1.

Step 5: 4-{3-(cyanomethyl)-3-[4-(1H-pyrrolo[2,3-b]pyridin-4-yl)-1H-pyrazol-1-yl]azetidin-1-yl}-3-fluoro-N-isopropylbenzamide N,N-Diisopropylethylamine (63 µL, 0.36 mmol) was added to a mixture of 4-{3-(cyanomethyl)-3-[4-(1H-pyrrolo[2,3-b]pyridin-4-yl)-1H-pyrazol-1-yl]azetidin-1-yl}-3-fluorobenzoic acid (50.0 mg, 0.120 mmol), and benzotriazol-1-yloxytris(dimethylamino)phosphonium hexafluorophosphate (64 mg, 0.14 mmol) and 2-propanamine (11 mg, 0.18 mmol) in methylene chloride (10 mL). The reaction mixture was stirred at room temperature overnight. The reaction mixture was worked up with aqueous NaHCO$_3$, and extracted with dichloromethylene (2×10 mL). The combined organic layers were washed with brine, dried over MgSO$_4$, filtered and concentrated under reduced pressure. The residue was purified by RP-HPLC (pH=10) to afford the desired product. LCMS (M+H)$^+$: m/z=458.1.

Example 28. 4-{3-(Cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide

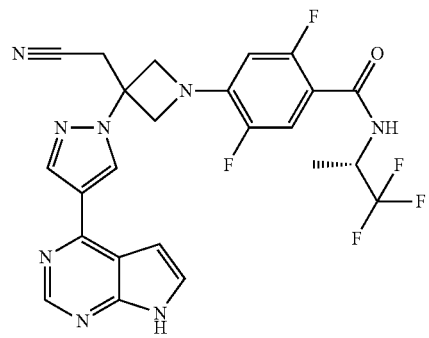 [SMILES: C[C@H](NC(=O)c1cc(F)c(N2CC(CC#N)(n3cc(-c4ncnc5[nH]ccc45)cn3)C2)cc1F)C(F)(F)F]

Step 1: 4-chloro-2,5-difluoro-N-[(1S)-2,2,2-trifluoro-1-methylethyl]benzamide

4-Chloro-2,5-difluorobenzoyl chloride (29.6 mg, 0.140 mmol) (Oakwood, Cat.#: 001628) was added to a mixture of (2S)-1,1,1-trifluoropropan-2-amine hydrochloride (20.0 mg, 0.134 mmol) (SynQuest Lab, Cat.#: 3130-7-S1) and diisopropylethylamine (58 µL, 0.33 mmol) in dichloromethylene (4.0 mL) at 0° C. The reaction mixture was stirred at room temperature for 30 min., worked up with saturated aqueous NaHCO$_3$, and extracted with dichloromethylene (3×10 mL). The combined organic layers were washed with brine, dried over MgSO$_4$, filtered and concentrated under reduced pressure to afford the desired product which was directly used in the next step reaction without further purification. LCMS (M+H)$^+$: m/z=288.0/290.0.

Step 2: 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide (R)-(+)-2,2'-Bis(diphenylphosphino)-1,1'-binaphthyl (8.3 mg, 0.013 mmol) was added to a mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (65 mg, 0.13 mmol), 4-chloro-2,5-difluoro-N-[(1S)-2,2,2-trifluoro-1-methylethyl]benzamide (0.14 mmol), and cesium carbonate (0.13 g, 0.40 mmol) in toluene (4.0 mL) under N$_2$, followed by palladium acetate (3.0 mg, 0.013 mmol). The reaction mixture was stirred at 130° C. for 5 h. After the reaction mixture was cooled to room temperature, the mixture was worked up with water, and extracted with ethyl acetate (3×10 mL). The combined organic layers were washed with brine, dried over MgSO$_4$, filtered and concentrated under reduced pressure to afford the crude product which was directly used in the next step reaction without further purification. LCMS (M+H)$^+$: m/z=661.2.

Step 3: 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide Boron trifluoride etherate (0.051 mL, 0.40 mmol) was added to a solution of 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide in acetonitrile (1.0 mL) at 0° C. under $N_2$. The reaction mixture was stirred at room temperature for 3 h. (LCMS (M+H)$^+$: m/z=561.3). Then the mixture was cooled to 0° C., water (0.13 mL) was added. After 30 min, 5.0 M ammonium hydroxide in water (0.2 mL, 1 mmol) was added slowly at 0° C. over 5 min. The reaction mixture was stirred at room temperature overnight, and purified by RP-HPLC (pH=10) to afford the desired product. LCMS (M+H)$^+$: m/z=531.0. $^1$H NMR (400 MHz, DMSO-d6): δ 12.62 (br, 1H), 9.07 (s, 1H), 8.84 (s, 1H), 8.55 (s, 1H), 8.51 (dd, J=8.8, 1.2 Hz, 1H), 7.78 (br, 1H), 7.35 (dd, J=12.6, 6.5 Hz, 1H), 7.23 (d, J=1.9 Hz, 1H), 6.65 (dd, J=11.9, 7.3 Hz, 1H), 4.76 (m, 1H), 4.70 (d, J=9.3 Hz, 2H), 4.44 (d, J=9.2 Hz, 2H), 3.76 (s, 2H), 1.30 (d, J=7.1 Hz, 3H).

Example 29. 4-{3-(Cyanomethyl)-3-[4-(7H-pyrrolo[2,3-d]pyrimidin-4-yl)-1H-pyrazol-1-yl]azetidin-1-yl}-2,5-difluoro-N-[(1R)-2,2,2-trifluoro-1-methylethyl]benzamide

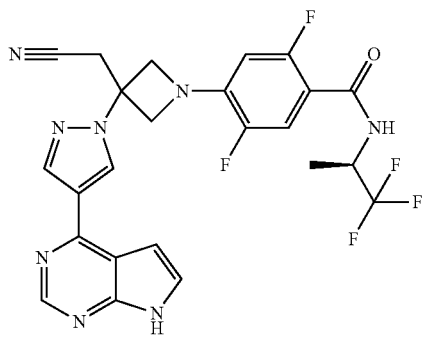 [SMILES: C[C@@H](NC(=O)c1cc(F)c(N2CC(CC#N)(n3cc(-c4ncnc5[nH]ccc45)cn3)C2)cc1F)C(F)(F)F]

Step 1: 4-chloro-2,5-difluoro-N-[(1R)-2,2,2-trifluoro-1-methylethyl]benzamide 4-Chloro-2,5-difluorobenzoyl chloride (29.6 mg, 0.140 mmol) (Oakwood, Cat.#: 001628) was added to a solution of (2R)-1,1,1-trifluoropropan-2-amine hydrochloride (20.0 mg, 0.134 mmol) (SynQuest Lab, Cat.#: 3130-7-R1) in methylene chloride (4.0 mL) at 0° C. The reaction mixture was stirred at room temperature for 30 min., then worked up with saturated aqueous $NaHCO_3$, and extracted with dichloromethylene. The combined organic layers were washed with brine, dried over $MgSO_4$, filtered and concentrated under reduced pressure to afford the desired product which was directly used in the next step reaction without further purification. LCMS (M+H)$^+$: m/z=288.0/289.9.

Step 2: 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-2,5-difluoro-N-[(1R)-2,2,2-trifluoro-1-methylethyl]benzamide (R)-(+)-2,2'-Bis(diphenylphosphino)-1,1'-binaphthyl (8.3 mg, 0.013 mmol) was added to a mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (65 mg, 0.13 mmol), 4-chloro-2,5-difluoro-N-[(1R)-2,2,2-trifluoro-1-methylethyl]benzamide (0.14 mmol), and cesium carbonate (0.13 g, 0.40 mmol) in toluene (4.0 mL) under $N_2$, followed by palladium acetate (3.0 mg, 0.013 mmol). The reaction mixture was stirred at 130° C. for 5 h. After the reaction mixture was cooled to room temperature, the mixture was worked up with water, and extracted with ethyl acetate (3×10 mL). The combined organic layers were washed with brine, dried over $MgSO_4$, filtered and concentrated under reduced pressure to afford the crude product which was directly used in the next step reaction without further purification. LCMS (M+H)$^+$: m/z=661.3.

Step 3: 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1R)-2,2,2-trifluoro-1-methylethyl]benzamide Boron trifluoride etherate (0.051 mL, 0.40 mmol) was added to a solution of the above intermediate in acetonitrile (1.0 mL) at 0° C. under $N_2$. The reaction mixture was stirred at room temperature for 3 h. LCMS (M+H)$^+$: m/z=561.2. Then the mixture was cooled to 0° C., water (0.13 mL) was added. After 30 min., 5.0 M ammonium hydroxide in water (0.2 mL, 1 mmol) was added slowly at 0° C. in 5 min. Then the reaction mixture was stirred at room temperature overnight. The mixture was purified by RP-HPLC (pH=10) to afford the desired product. LCMS (M+H)$^+$: m/z=531.2.

Example 30. 5-{3-(Cyanomethyl)-3-[4-(7H-pyrrolo[2,3-d]pyrimidin-4-yl)-1H-pyrazol-1-yl]azetidin-1-yl}-N-[(1R)-2,2,2-trifluoro-1-methylethyl]pyrazine-2-carboxamide

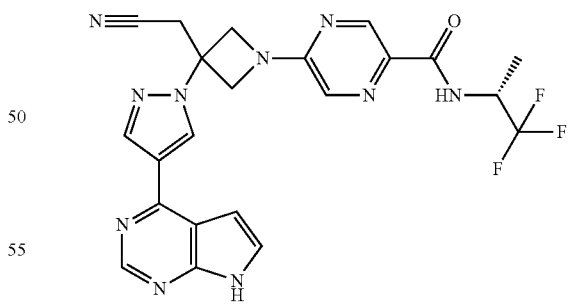

Step 1: 5-chloro-N-[(1R)-2,2,2-trifluoro-1-methylethyl]pyrazine-2-carboxamide N,N-Diisopropylethylamine (1.3 mL, 7.5 mmol) was added to a mixture of 5-chloropyrazine-2-carboxylic acid (0.40 g, 2.5 mmol) (Matrix, Cat.#: 054028), N,N,N',N'-tetramethyl-O-(7-azabenzotriazol-1-yl)uronium hexafluorophosphate (1.0 g, 2.8 mmol) and (2R)-1,1,1-trifluoropropan- 2-amine hydrochloride (0.38 g, 2.5 mmol) in methylene chloride (10 mL). The reaction mixture was stirred at room temperature overnight. The reaction mixture was worked up with saturated aqueous NaHCO$_3$, and extracted with ethyl acetate (3×20 mL). The combined organic layers were washed with brine, dried over MgSO$_4$, filtered and concentrated under reduced pressure. The residue was purified by flash chromatography on a silica gel column with ethyl acetate in hexanes (0-20%) to afford the desired product (0.64 g, 76%). LCMS (M+H)$^+$: m/z=253.9/255.9.

Step 2: 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[(1R)-2,2,2-trifluoro-1-methylethyl]pyrazine-2-carboxamide N,N-Diisopropylethylamine (0.11 mL, 0.62 mmol) was added to a mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (110 mg, 0.22 mmol) and 5-chloro-N-[(1R)-2,2,2-trifluoro-1-methylethyl]pyrazine-2-carboxamide (52 mg, 0.21 mmol) in NMP (2.0 mL). The reaction mixture was stirred at 125° C. for 2 h. The reaction mixture was worked up with saturated aqueous NaHCO$_3$, and extracted with dichloromethylene (3×20 mL). The combined organic layers were washed with brine, dried over MgSO$_4$, filtered and concentrated under reduced pressure. The residue was purified by flash chromatography on a silica gel column with ethyl acetate in dichloromethylene (0-70%) to afford the desired product. LCMS (M+H)$^+$: m/z=627.2.

Step 3: 5-{3-(cyanomethyl)-3-[4-(7H-pyrrolo[2,3-d]pyrimidin-4-yl)-1H-pyrazol-1-yl]azetidin-1-yl}-N-[(1R)-2,2,2-trifluoro-1-methylethyl]pyrazine-2-carboxamide Boron trifluoride etherate (0.078 mL, 0.62 mmol) was added to a solution of 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[(1R)-2,2,2-trifluoro-1-methylethyl]pyrazine-2-carboxamide in acetonitrile (4.0 mL) at 0° C. under N$_2$. The reaction mixture was stirred at room temperature for 3 h. [LCMS (M+H)$^+$: m/z=527.2]. The mixture was cooled to 0° C., water (1.6 mL) was added. After 30 min., 5.0 M ammonium hydroxide in water (0.38 mL, 1.9 mmol) was added slowly at 0° C. over 5 min. Then the reaction mixture was stirred at room temperature overnight. The mixture was worked up with saturated aqueous NaHCO$_3$, extracted with ethyl acetate (3×20 mL). The combined organic layers were washed with brine, dried over MgSO$_4$, filtered and concentrated under reduced pressure. The residue was purified by flash chromatography on a silica gel column with methanol in dichloromethane (0-5%) to afford the desired product (60 mg, 58%). LCMS (M+H)$^+$: m/z=497.1. $^1$H NMR (400 MHz, DMSO-d$_6$): δ 12.73 (br, 1H), 9.13 (s, 1H), 8.87 (s, 1H), 8.83 (d, J=9.2 Hz, 1H), 8.68 (d, J=1.4 Hz, 1H), 8.58 (s, 1H), 8.02 (d, J=1.4 Hz, 1H), 7.82 (dd, J=3.1, 2.2 Hz, 1H), 7.27 (dd, J=3.3, 1.3 Hz, 1H), 4.83 (d, J=9.8 Hz, 2H), 4.81 (m, 1H), 4.58 (d, J=9.9 Hz, 2H), 3.80 (s, 2H), 1.36 (d, J=7.1 Hz, 3H).

Example 31. 5-{3-(Cyanomethyl)-3-[4-(7H-pyrrolo[2,3-d]pyrimidin-4-yl)-1H-pyrazol-1-yl]azetidin-1-yl}-N-[(1S)-2,2,2-trifluoro-1-methylethyl]pyrazine-2-carboxamide

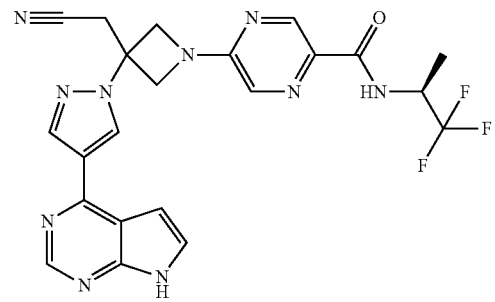 [SMILES: C[C@H](NC(=O)c1cnc(N2CC(CC#N)(n3cc(-c4ncnc5[nH]ccc45)cn3)C2)cn1)C(F)(F)F]

Step 1: 5-chloro-N-[(1S)-2,2,2-trifluoro-1-methylethyl]pyrazine-2-carboxamide N,N-Diisopropylethylamine (1.3 mL, 7.5 mmol) was added to a mixture of 5-chloropyrazine-2-carboxylic acid (0.40 g, 2.5 mmol), N,N,N',N'-tetramethyl-O-(7-azabenzotriazol-1-yl)uronium hexafluorophosphate (1.0 g, 2.8 mmol) and (2S)-1,1,1-trifluoropropan-2-amine (0.28 g, 2.5 mmol) (Oakwood: Cat.#44272) in methylene chloride (10 mL). The reaction mixture was stirred at room temperature overnight. The reaction mixture was worked up with saturated aqueous NaHCO$_3$, and extracted with ethyl acetate (3×20 mL). The combined organic layers were washed with brine, dried over MgSO$_4$, filtered and concentrated under reduced pressure. The residue was purified by flash chromatography on a silica gel column with ethyl acetate in hexanes (0-15%) to afford the desired product (0.64 g, 73%). LCMS (M+H)$^+$: m/z=253.9/255.9.

Step 2: 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[(1S)-2,2,2-trifluoro-1-methylethyl]pyrazine-2-carboxamide N,N-Diisopropylethylamine (0.11 mL, 0.62 mmol) was added to a mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (110 mg, 0.22 mmol) and 5-chloro-N-[(1S)-2,2,2-trifluoro-1-methylethyl]pyrazine-2-carboxamide (52 mg, 0.21 mmol) in NMP (3.0 mL). The reaction mixture was stirred at 120° C. for 2 h. The reaction mixture was worked up with saturated aqueous NaHCO$_3$, and extracted with dichloromethylene (3×20 mL). The combined organic layers were washed with brine, dried over MgSO$_4$, filtered and concentrated under reduced pressure. The residue was purified by flash chromatography on a silica gel column with ethyl acetate in dichloromethylene (0-65%) to afford the desired product (100 mg, 73%). LCMS (M+H)$^+$: m/z=627.2.

Step 3: 5-{3-(cyanomethyl)-3-[4-(7H-pyrrolo[2,3-d]pyrimidin-4-yl)-1H-pyrazol-1-yl]azetidin-1-yl}-N-[(1S)-2,2,2-trifluoro-1-methylethyl]pyrazine-2-carboxamide Boron trifluoride etherate (0.078 mL, 0.62 mmol) was added to a solution of 5-{3-(cyanomethyl)-3-[4-(7-{[2-

(trimethylsilyl)ethoxy]methyl}-7H-pyrrolo[2,3-d]pyrimidin-4-yl)-1H-pyrazol-1-yl]azetidin-1-yl}-N-[(1S)-2,2,2-trifluoro-1-methylethyl]pyrazine-2-carboxamide in acetonitrile (4.0 mL) at 0° C. under $N_2$. The reaction mixture was stirred at room temperature for 3 h. (LCMS (M+H)$^+$: m/z=527.2). The mixture was cooled to 0° C., water (1.6 mL) was added. After 30 min., 5.0 M ammonium hydroxide in water (0.38 mL, 1.9 mmol) was added slowly at 0° C. in 5 min. Then the reaction mixture was stirred at room temperature overnight. The mixture was worked up with saturated aqueous NaHCO$_3$, extracted with ethyl acetate (3×20 mL). The combined organic layers were washed with brine, dried over MgSO$_4$, filtered and concentrated under reduced pressure. The residue was purified by flash chromatography on a silica gel column with methanol in dichloromethane (0-5%) to afford the desired product (52 mg, 51%). LCMS (M+H)$^+$: m/z=497.1. $^1$H NMR (400 MHz, DMSO-d$_6$): δ 12.60 (br, 1H), 9.09 (s, 1H), 8.84 (d, J=8.8 Hz, 1H), 8.83 (s, 1H), 8.69 (d, J=1.4 Hz, 1H), 8.56 (s, 1H), 8.02 (d, J=1.4 Hz, 1H), 7.77 (br, 1H), 7.23 (br, 1H), 4.84 (d, J=9.9 Hz, 2H), 4.80 (m, 1H), 4.57 (d, J=9.9 Hz, 2H), 3.80 (s, 2H), 1.36 (d, J=7.1 Hz, 3H).

Example 32. 5-{3-(Cyanomethyl)-3-[4-(7H-pyrrolo[2,3-d]pyrimidin-4-yl)-1H-pyrazol-1-yl]azetidin-1-yl}-N-[(1S)-1-cyclopropyl-2,2,2-trifluoroethyl]pyrazine-2-carboxamide

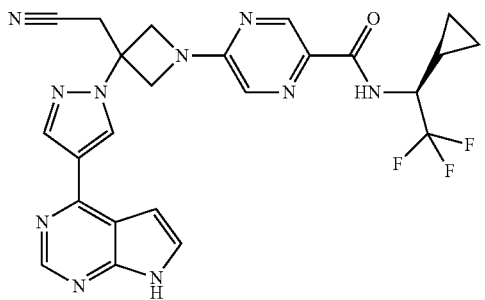 [SMILES: N#CCC1(n2cc(-c3ncnc4[nH]ccc34)cn2)CN(c2cnc(C(=O)N[C@@H](C3CC3)C(F)(F)F)cn2)C1]

Step 1: 5-chloro-N-[(1S)-1-cyclopropyl-2,2,2-trifluoroethyl]pyrazine-2-carboxamide N,N-Diisopropylethylamine (1.3 mL, 7.5 mmol) was added to a mixture of 5-chloropyrazine-2-carboxylic acid (0.40 g, 2.5 mmol), N,N,N',N'-tetramethyl-O-(7-azabenzotriazol-1-yl)uronium hexafluorophosphate (1.0 g, 2.8 mmol) and (1S)-1-cyclopropyl-2,2,2-trifluoroethanamine hydrochloride (0.44 g, 2.5 mmol) (ASIBA Pharmatech, Cat.#: 70092-HCl) in methylene chloride (10 mL). The reaction mixture was stirred at room temperature overnight. The mixture was worked up with saturated aqueous NaHCO$_3$, and extracted with ethyl acetate (3×20 mL). The combined organic layers were washed with brine, dried over MgSO$_4$, filtered and concentrated under reduced pressure. The residue was purified by flash chromatography on a silica gel column with ethyl acetate in hexanes (0-20%) to afford the desired product (0.51 g, 72%). LCMS (M+H)$^+$: m/z=280.0/282.0.

Step 2: 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[(1S)-1-cyclopropyl-2,2,2-trifluoroethyl]pyrazine-2-carboxamide N,N-Diisopropylethylamine (0.11 mL, 0.62 mmol) was added to a mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (110 mg, 0.22 mmol) and 5-chloro-N-[(1S)-1-cyclopropyl-2,2,2-trifluoroethyl]pyrazine-2-carboxamide (58 mg, 0.21 mmol) in NMP (2.0 mL). The reaction mixture was stirred at 125° C. for 2 h. The reaction mixture was worked up with saturated aqueous NaHCO$_3$, and extracted with dichloromethylene (3×20 mL). The combined organic layers were washed with brine, dried over MgSO$_4$, filtered and concentrated under reduced pressure. The residue was purified by flash chromatography on a silica gel column with ethyl acetate in dichloromethylene (0-65%) to afford the desired product (80 mg, 59%). LCMS (M+H)$^+$: m/z=653.2.

Step 3: 5-{3-(cyanomethyl)-3-[4-(7H-pyrrolo[2,3-d]pyrimidin-4-yl)-1H-pyrazol-1-yl]azetidin-1-yl}-N-[(1S)-1-cyclopropyl-2,2,2-trifluoroethyl]pyrazine-2-carboxamide Boron trifluoride etherate (0.078 mL, 0.62 mmol) was added to a solution of 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[(1S)-1-cyclopropyl-2,2,2-trifluoroethyl]pyrazine-2-carboxamide in acetonitrile (4.0 mL) at 0° C. under $N_2$. The reaction mixture was stirred at room temperature for 3 h. LCMS (M+H)$^+$: m/z=553.2. The mixture was cooled to 0° C., then water (1.6 mL) was added. After 30 min, 5.0 M ammonium hydroxide in water (0.38 mL) was added slowly at 0° C. over 5 min. Then the reaction mixture was stirred at room temperature overnight. The reaction mixture was worked up with saturated aqueous NaHCO$_3$, and extracted with ethyl acetate (3×20 mL). The combined organic layers were washed with brine, dried over MgSO$_4$, filtered and concentrated under reduced pressure. The residue was purified by flash chromatography on a silica gel column with methanol in dichloromethane (0-5%) to afford the desired product. LCMS (M+H)$^+$: m/z=523.2. $^1$H NMR (400 MHz, DMSO-d$_6$): δ 12.53 (br, 1H), 8.94 (s, 1H), 8.79 (d, J=9.3 Hz, 1H), 8.68 (s, 1H), 8.51 (d, J=1.4, 1H), 8.40 (s, 1H), 7.86 (d, J=1.4 Hz, 1H), 7.63 (dd, J=3.1, 2.3 Hz, 1H), 7.08 (dd, J=3.3, 1.4 Hz, 1H), 4.66 (d, J=9.9 Hz, 2H), 4.40 (d, J=10.0 Hz, 2H), 3.82 (m, 1H), 3.63 (s, 2H), 1.22 (m, 1H), 0.48 (m, 1H), 0.38 (m, 1H), 0.30 (m, 1H), 0.02 (m, 1H).

Example 33. 5-{3-(Cyanomethyl)-3-[4-(7H-pyrrolo[2,3-d]pyrimidin-4-yl)-1H-pyrazol-1-yl]azetidin-1-yl}-N-[1-(trifluoromethyl)cyclopropyl]pyrazine-2-carboxamide

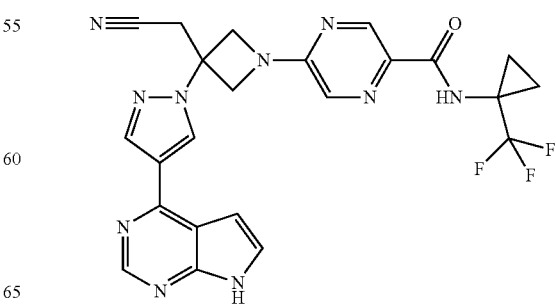

Step 1: 5-chloro-N-[1-(trifluoromethyl)cyclopropyl]pyrazine-2-carboxamide

N,N-Diisopropylethylamine (1.3 mL, 7.5 mmol) was added to a mixture of 5-chloropyrazine-2-carboxylic acid (0.40 g, 2.5 mmol), N,N,N',N'-tetramethyl-O-(7-azabenzotriazol-1-yl)uronium hexafluorophosphate (1.0 g, 2.8 mmol) and 1-(trifluoromethyl)cyclopropanamine (0.32 g, 2.5 mmol) (Oakwood, Cat.#: 038175) in dichloromethylene (10 mL). The reaction mixture was stirred at room temperature overnight. The reaction mixture was worked up with saturated aqueous NaHCO$_3$, and extracted with ethyl acetate (3×20 mL). The combined organic layers were washed with brine, dried over MgSO$_4$, filtered and concentrated under reduced pressure. The residue was purified by flash chromatography on a silica gel column with ethyl acetate in hexanes (0-20%) to afford the desired product (0.41 g, 67%). LCMS (M+H)$^+$: m/z=266.0/267.9.

Step 2: 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[1-(trifluoromethyl)cyclopropyl]pyrazine-2-carboxamide N,N-Diisopropylethylamine (0.71 mL, 4.1 mmol) was added to a mixture of {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile dihydrochloride (0.70 g, 1.4 mmol) and 5-chloro-N-[1-(trifluoromethyl)cyclopropyl]pyrazine-2-carboxamide (0.36 g, 1.4 mmol) in NMP (5.0 mL). The reaction mixture was stirred at 125° C. for 2 h. The reaction mixture was worked up with saturated aqueous NaHCO$_3$, and extracted with dichloromethylene (3×20 mL). The combined organic layers were washed with brine, dried over MgSO$_4$, filtered and concentrated under reduced pressure. The residue was purified by flash chromatography on a silica gel column with ethyl acetate in dichloromethylene (0-80%) to afford the desired product (0.90 g). LCMS (M+H)$^+$: m/z=639.2.

Step 3: 5-{3-(cyanomethyl)-3-[4-(7H-pyrrolo[2,3-d]pyrimidin-4-yl)-1H-pyrazol-1-yl]azetidin-1-yl}-N-[1-(trifluoromethyl)cyclopropyl]pyrazine-2-carboxamide Boron trifluoride etherate (0.52 mL, 4.1 mmol) was added to a solution of 5-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-N-[1-(trifluoromethyl)cyclopropyl]pyrazine-2-carboxamide (0.90 g) in acetonitrile (20 mL) at 0° C. under N$_2$. The reaction mixture was stirred at room temperature for 4 h. LCMS (M+H)$^+$: m/z=539.2. The mixture was cooled to 0° C., water (10. mL) was added. After 30 min., 5.0 M ammonium hydroxide in water (2.5 mL) was added slowly at 0° C. in 5 min. Then the reaction mixture was stirred at room temperature overnight. The reaction mixture was worked up with saturated aqueous NaHCO$_3$, extracted with ethyl acetate (3×20 mL). The combined organic layers were washed with brine, dried over MgSO$_4$, filtered and concentrated under reduced pressure. The residue was purified by flash chromatography on a silica gel column with methanol in dichloromethylene (0-5%) to afford the desired product (0.69 g, 63%). LCMS (M+H)$^+$: m/z=509.0. $^1$H NMR (300 MHz, DMSO-d$_6$): δ 12.71 (br, 1H), 9.16 (s, 1H), 9.13 (s, 1H), 8.88 (s, 1H), 8.68 (d, J=1.2 Hz, 1H), 8.60 (s, 1H), 8.02 (d, J=1.2 Hz, 1H), 7.83 (dd, J=3.2, 2.5 Hz, 1H), 7.28 (dd, J=3.4, 1.4 Hz, 1H), 4.85 (d, J=9.8 Hz, 2H), 4.59 (d, J=10.0 Hz, 2H), 3.82 (s, 2H), 1.29 (m, 2H), 1.17 (m, 2H).

Example 34. 5-{3-(Cyanomethyl)-3-[4-(1H-pyrrolo[2,3-b]pyridin-4-yl)-1H-pyrazol-1-yl]azetidin-1-yl}-N-isopropylpyrazine-2-carboxamide

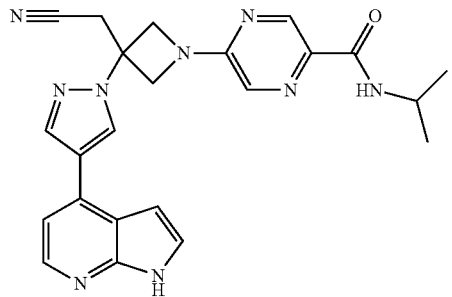 [SMILES: CC(C)NC(=O)c1cnc(N2CC(CC#N)(n3cc(-c4ccnc5[nH]ccc45)cn3)C2)cn1]

Step 1: methyl 5-{3-(cyanomethyl)-3-[4-(1-{[2-(trimethylsilyl)ethoxy]methyl}-1H-pyrrolo[2,3-b]pyridin-4-yl)-1H-pyrazol-1-yl]azetidin-1-yl}pyrazine-2-carboxylate N,N-Diisopropylethylamine (1.0 mL, 6.0 mmol) was added to a mixture of {3-[4-(1-{[2-(trimethylsilyl)ethoxy]methyl}-1H-pyrrolo[2,3-b]pyridin-4-yl)-1H-pyrazol-1-yl]azetidin-3-yl}acetonitrile dihydrochloride (0.96 g, 2.0 mmol) and methyl 5-chloropyrazine-2-carboxylate (0.34 g, 2.0 mmol) in 1,4-dioxane (15 mL). The reaction mixture was stirred at 120° C. overnight. The mixture was worked up with saturated aqueous NaHCO$_3$, and extracted with dichloromethylene (3×20 mL). The combined organic layers were washed with brine, dried over MgSO$_4$, filtered and concentrated under reduced pressure. The residue was purified by flash chromatography on a silica gel column with ethyl acetate in hexanes (0-60%) to afford the desired product (0.13 g, 12%). LCMS (M+H)$^+$: m/z=545.2.

Step 2: 5-{3-(cyanomethyl)-3-[4-(1-{[2-(trimethylsilyl)ethoxy]methyl}-1H-pyrrolo[2,3-b]pyridin-4-yl)-1H-pyrazol-1-yl]azetidin-1-yl}pyrazine-2-carboxylic acid A reaction mixture of methyl 5-{3-(cyanomethyl)-3-[4-(1-{[2-(trimethylsilyl)ethoxy]methyl}-1H-pyrrolo[2,3-b]pyridin-4-yl)-1H-pyrazol-1-yl]azetidin-1-yl}pyrazine-2-carboxylate (0.13 g, 0.24 mmol), lithium hydroxide monohydrate (0.025 g, 0.60 mmol) in methanol (4.0 mL), THF (2.0 mL) and water (1.0 mL) was stirred at 40° C. for 3 h. The mixture was adjusted to pH=4 with 2.0 N HCl aqueous solution, and concentrated under reduced pressure to remove MeOH and THF. The precipitate formed was filtered, washed with water and ether, and dried in vacuum to afford the desired product (0.100 g, 79%). LCMS (M+H)+: m/z=531.4.

Step 3: 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide N,N-Diisopropylethylamine (19 μL, 0.11 mmol) was added to a mixture of 5-{3-(cyanomethyl)-3-[4-(1-{[2-(trimethylsilyl)ethoxy]methyl}-1H-pyrrolo[2,3-b]pyridin-4-yl)-1H-pyrazol-1-yl]azetidin-1-yl}pyrazine-2-carboxylic acid (19.4 mg, 0.0365 mmol), benzotriazol-1-yloxytris(dimethylamino)phosphonium hexafluorophosphate (19 mg, 0.044 mmol) and 2-propanamine (3.2 mg, 0.055 mmol) in DMF (1.0 mL). The reaction mixture was stirred at room temperature overnight. The reaction mixture was worked up with saturated aqueous NaHCO$_3$, and extracted with dichloromethylene (3×20 mL). The combined organic layers were washed with brine, dried over MgSO$_4$, filtered and concentrated under reduced pressure. The residue was treated with methylene chloride (1.3 mL) and TFA (1.3 mL). The mixture was stirred at room temperature for 1.5 h., and concentrated under reduced pressure. The residue was dissolved in methanol (1.3 mL), and treated with ethylenediamine (0.086 mL, 1.3 mmol). The resulting mixture was stirred at room temperature for 2 h, and then purified by RP-HPLC (pH=10) to afford the desired product. LCMS (M+H)$^+$: m/z=442.1. $^1$H NMR (400 MHz, DMSO-d$_6$): δ 12.19 (br, 1H), 8.99 (s, 1H), 8.66 (d, J=1.4 Hz, 1H), 8.47 (s, 1H), 8.32 (d, J=5.7 Hz, 1H), 8.14 (d, J=8.4 Hz, 1H), 8.00 (d, J=1.4 Hz, 1H), 7.67 (dd, J=3.2, 2.7 Hz, 1H), 7.54 (d, J=5.5 Hz, 1H), 7.09 (dd, J=3.5, 2.7 Hz, 1H), 4.82 (d, J=10.0 Hz, 2H), 4.56 (d, J=10.0 Hz, 2H), 4.10 (m, 1H), 3.79 (s, 2H), 1.17 (d, J=6.4 Hz, 6H).

Example 35. 5-{3-(Cyanomethyl)-3-[4-(1H-pyrrolo[2,3-b]pyridin-4-yl)-1H-pyrazol-1-yl]azetidin-1-yl}-N-[(1S)-2,2,2-trifluoro-1-methylethyl]pyrazine-2-carboxamide

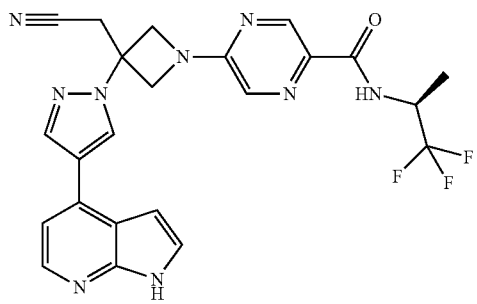 [SMILES: C[C@H](NC(=O)c1cnc(N2CC(CC#N)(n3cc(-c4ccnc5[nH]ccc45)cn3)C2)cn1)C(F)(F)F]

This compound was prepared by using procedures analogous to those described for the synthesis of Example 34, Step 3 starting from 5-{3-(cyanomethyl)-3-[4-(1-{[2-(trimethylsilyl)ethoxy]methyl}-1H-pyrrolo[2,3-b]pyridin-4-yl)-1H-pyrazol-1-yl]azetidin-1-yl}pyrazine-2-carboxylic acid and (2S)-1,1,1-trifluoropropan-2-amine hydrochloride. LCMS (M+H)$^+$: m/z=496.1. $^1$H NMR (400 MHz, DMSO-d$_6$) δ 12.23 (br, 1H), 8.99 (s, 1H), 8.83 (d, J=9.3 Hz, 1H), 8.69 (d, J=1.4 Hz, 1H), 8.47 (s, 1H), 8.32 (d, J=5.6 Hz, 1H), 8.02 (d, J=1.4 Hz, 1H), 7.67 (dd, J=3.3, 2.6 Hz, 1H), 7.55 (d, J=5.5 Hz, 1H), 7.09 (dd, J=3.4, 1.7 Hz, 1H), 4.83 (d, J=10.0 Hz, 2H), 4.80 (m, 2H), 4.57 (d, J=9.6 Hz, 2H), 3.78 (s, 2H), 1.36 (d, J=7.2 Hz, 3H).

Example 36. 5-{3-(Cyanomethyl)-3-[4-(1H-pyrrolo[2,3-b]pyridin-4-yl)-1H-pyrazol-1-yl]azetidin-1-yl}-N-(2,2,2-trifluoroethyl)pyrazine-2-carboxamide

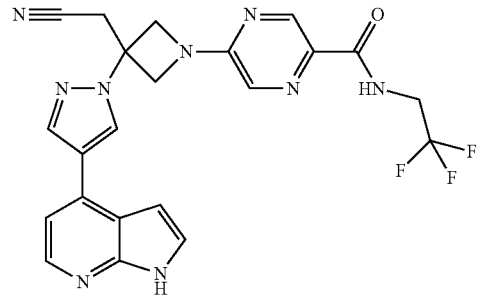 [SMILES: N#CCC1(n2cc(-c3ccnc4[nH]ccc34)cn2)CN(c2cnc(C(=O)NCC(F)(F)F)cn2)C1]

This compound was prepared by using procedures analogous to those described for the synthesis of Example 34, Step 3 starting from 5-{3-(cyanomethyl)-3-[4-(1-{[2-(trimethylsilyl)ethoxy]methyl}-1H-pyrrolo[2,3-b]pyridin-4-yl)-1H-pyrazol-1-yl]azetidin-1-yl}pyrazine-2-carboxylic acid and 2,2,2-trifluoroethanamine. LCMS (M+H)$^+$: m/z=482.1.

Example 37. 4-{3-(Cyanomethyl)-3-[4-(7H-pyrrolo[2,3-d]pyrimidin-4-yl)-1H-pyrazol-1-yl]azetidin-1-yl}-N-(2,2-difluoroethyl)-2,5-difluorobenzamide

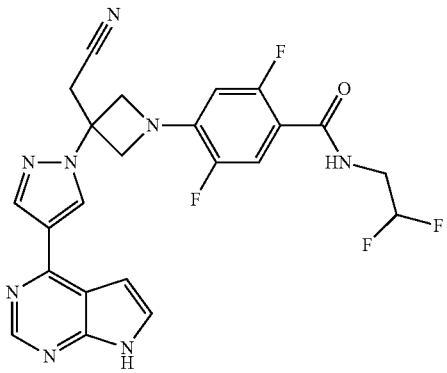 [SMILES: N#CCC1(n2cc(-c3ncnc4[nH]ccc34)cn2)CN(c2cc(F)c(C(=O)NCC(F)F)cc2F)C1]

Step 1: 4-chloro-N-(2,2-difluoroethyl)-2,5-difluorobenzamide

A solution of 4-chloro-2,5-difluorobenzoic acid (1.28 g, 6.64 mmol), N,N-diisopropylethylamine (3.5 mL, 20 mmol), and N,N,N',N'-tetramethyl-O-(7-azabenzotriazol-1-yl)uronium hexafluorophosphate (3.07 g, 8.07 mmol) in 1,2-dichloroethane (20 mL) was stirred for 10 min. at room temperature prior to the addition of a solution of 2,2-difluoroethanamine (538 mg, 6.64 mmol) in dichloroethane (2 mL). The resulting solution was stirred for 1 h. at room temperature. LCMS data indicated that the major reaction component was the desired product. The crude reaction mixture was concentrated under reduced pressure. The residue was purified by flash chromatography on a silica gel column with methanol in dichloromethane (0-10%) to afford the desired product. LCMS (M+H)$^+$: m/z=256.0.

Step 2: 4-{3-(cyanomethyl)-3-[4-(7H-pyrrolo[2,3-d]pyrimidin-4-yl)-1H-pyrazol-1-yl]azetidin-1-yl}-N-(2,2-difluoroethyl)-2,5-difluorobenzamide A solution of 4-chloro-N-(2,2-difluoroethyl)-2,5-difluorobenzamide (0.907 g, 3.55 mmol), {3-[4-(7-{[2-(trimethylsilyl)ethoxy]methyl}-7H-pyrrolo[2,3-d]pyrimidin-4-yl)-1H-pyrazol-1-yl]azetidin-3-yl}acetonitrile HCl salt (1.57 g, 3.52 mmol), palladium acetate (55 mg, 0.24 mmol), (9,9-dimethyl-9H-xanthene-4,5-diyl)bis(diphenylphosphine) (285 mg, 0.493 mmol) and cesium carbonate (2.16 g, 6.63 mmol) in toluene (25 mL) was de-gassed and purged with $N_2$ (g) several times prior to heating to 105° C. and stirring for 3 d. LCMS data indicated that ~50% of the starting material was converted to the desired product. In an effort to drive the reaction to completion a second aliquot of 4-chloro-N-(2,2-difluoroethyl)-2,5-difluorobenzamide (353 mg), palladium acetate (58 mg), (9,9-dimethyl-9H-xanthene-4,5-diyl)bis(diphenylphosphine) (274 mg), and cesium carbonate (550 mg) was added and stirring was continued overnight at 105° C. LCMS data indicated that there was no significant improvement. The crude reaction mixture was filtered through a pad of celite and the inorganics were washed thoroughly with ethyl acetate. The filtrate was concentrated under reduced pressure and the residue was purified by flash chromatography on a silica gel column with methanol in dichloromethane (0-15%) to afford the desired product (0.789 g).

The above pure product was dissolved in dichloromethane (10 mL) and treated with trifluoroacetic acid (10 mL). The mixture was stirred at ambient temperature for 2.5 h. The volatiles were removed under reduced pressure and the residue was azeotropically washed with acetonitrile (3×10 mL). The resulting residue was dissolved in methanol (20 mL) and treated with $NH_4OH$ aqueous solution (2 mL). The reaction mixture was stirred at ambient temperature for 2 h. The crude reaction mixture was concentrated in-vacuo and subjected to flash chromatography on a silica gel column with methanol in dichloromethane (0-15%) to afford the desired product (229 mg). The product was dissolved in acetonitrile (15 mL) and cooled to 0° C. prior to the addition of trifluoroacetic acid (0.2 mL). The reaction mixture was allowed to warm to ambient temperature while stirring for 30 min. Water (10 mL) was added and the solution was frozen and subjected to lyophilization to afford the desired product as the corresponding trifluoroacetic acid salt. LCMS (M+H)$^+$: m/z=499.4. $^1$H NMR (500 MHz, DMSO-d$_6$) δ 12.73 (s, 1H), 9.11 (s, 1H), 8.88 (s, 1H), 8.58 (s, 1H), 8.26 (q, J=5.7 Hz, 1H), 7.84-7.79 (m, 1H), 7.43 (dd, J=12.7, 6.5 Hz, 1H), 7.27 (d, J=2.0 Hz, 1H), 6.65 (dd, J=12.3, 7.3 Hz, 1H), 6.09 (tt, J=56.1, 4.1 Hz, 1H), 4.72 (d, J=8.8 Hz, 2H), 4.47 (d, J=7.8 Hz, 2H), 3.76 (s, 2H), 3.64 (tt, J=15.4, 4.4 Hz, 2H).

Example 38. 4-{3-(Cyanomethyl)-3-[4-(7H-pyrrolo[2,3-d]pyrimidin-4-yl)-1H-pyrazol-1-yl]azetidin-1-yl}-N-[(1S)-1-cyclopropyl-2,2,2-trifluoroethyl]benzamide

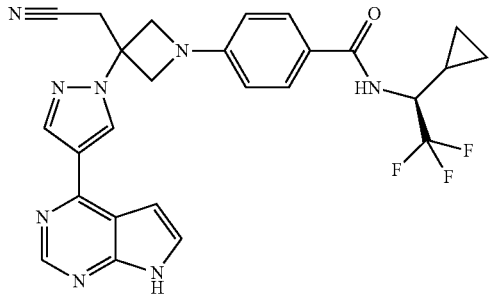 [SMILES: N#CCC1(n2cc(-c3ncnc4[nH]ccc34)cn2)CN(c2ccc(C(=O)N[C@@H](C3CC3)C(F)(F)F)cc2)C1]

To an oven dried vial containing (1S)-1-cyclopropyl-2,2,2-trifluoroethanamine HCl salt (130 mg, 0.74 mmol) (ASIBA Pharmatech, Cat.#: 70092-HCl) and equipped with a magnetic stirring bar was placed anhydrous 1,2-dichloroethane (0.5 mL) followed by N,N-diisopropylethylamine (140 μL, 0.83 mmol). The reaction vial was purged with $N_2$ (g) and sealed prior to the addition of 2.0 M trimethylaluminum in toluene (180 μL, 0.37 mmol). After stirring at room temperature for 20 min., a solution of methyl 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}benzoate (100. mg, 0.184 mmol) (Example 19, Step 1) in 1,2-dichloroethane (1.0 mL) was added and the reaction mixture was heated at 65° C. and stirred for 16 h. LCMS data indicated that the reaction was ~50% complete. A second aliquot of a pre-stirred solution of (1S)-1-cyclopropyl-2,2,2-trifluoroethanamine HCl salt (130 mg), N,N-diisopropylethylamine (140 μL), and 2.0 M trimethylaluminum in toluene (180 μL) in 1,2-dichloroethane (0.5 mL) was added and stirring was continued for 4 h. LC/MS data indicated that the reaction was complete. Upon cooling to room temperature, the reaction mixture was diluted with dichloromethane (4 mL) and DOWEX 50WX8-400 ion-exchange resin was carefully added to the reaction mixture. After stirring at room temperature for 30 min, the inorganics were filtered off and thoroughly washed with dichloromethane. The crude reaction mixture was purified by flash chromatography on a silica gel column with methanol in dichloromethane (0-10%) to afford the desired product (90 mg, 75% yield). The pure product was dissolved in dichloromethane (2 mL) and trifluoroacetic acid (2 mL) and was stirred at room temperature for 1 h. The volatiles were removed under reduced pressure and the residue was azeotropically washed with acetonitrile (3×3 mL). The resulting residue was dissolved in methanol (3 mL), and $NH_4OH$ aqueous solution (200 μL) and ethylenediamine (50 μL) were added and the reaction mixture was stirred at room temperature for 1 h. The crude reaction mixture was subjected to RP-HPLC (pH=2) to afford the desired product as the corresponding trifluoroacetic acid salt as a white solid. LCMS (M+H)$^+$: m/z=521.2. $^1$H NMR (500 MHz, DMSO-d$_6$): δ 12.48 (s, 1H), 9.03 (s, 1H), 8.80 (s, 1H), 8.66 (d, J=8.9 Hz, 1H), 8.53 (s, 1H), 7.84 (d, J=8.7 Hz, 2H), 7.73 (s, 1H), 7.18 (s, 1H), 6.62 (d, J=8.7 Hz, 2H), 4.58 (d, J=8.7 Hz, 2H), 4.33 (d, J=8.7 Hz, 2H), 4.08 (dt, J=17.3, 8.6 Hz, 1H), 3.76 (s, 2H), 1.30-1.19 (m, 1H), 0.68 (dt, J=12.4, 5.6 Hz, 1H), 0.51 (q, J=7.8, 6.8 Hz, 2H), 0.29-0.23 (m, 1H).

Example 39. 4-{3-(Cyanomethyl)-3-[4-(7H-pyrrolo[2,3-d]pyrimidin-4-yl)-1H-pyrazol-1-yl]azetidin-1-yl}-N-[(1R)-1-cyclopropylethyl]-2-fluorobenzamide

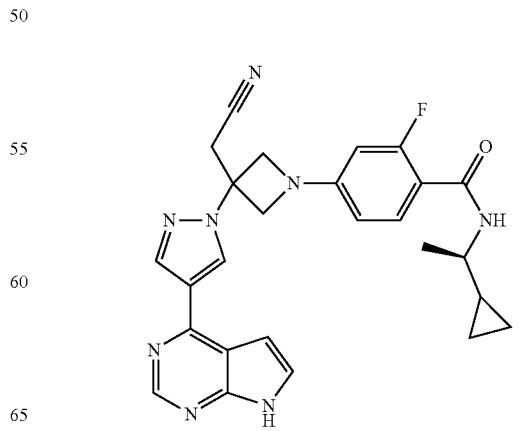

To a sealed vial that was purged with $N_2$ (g) and contained a solution of (1R)-1-cyclopropylethanamine (150 μL, 1.62 mmol) (Alfa Aesar H26902 lot 10151885, CAS 6240-96-9, 98% ee) in 1,2-dichloroethane (2 mL) was added 2.0 M trimethylaluminum in toluene (0.800 mL, 1.60 mmol) via syringe and the resulting solution was stirred at room temperature for 30 min. A solution of methyl 4-{3-(cyanomethyl)-3-[4-(7-{[2-(trimethylsilyl)ethoxy]methyl}-7H-pyrrolo[2,3-d]pyrimidin-4-yl)-1H-pyrazol-1-yl]azetidin-1-yl}-2-fluorobenzoate (300. mg, 0.534 mmol) (Example 15, Step 1) in 1,2-dichloroethane (3 mL) was added drop-wise via syringe. The solution was heated to 70° C. and stirred for 16 h. LCMS data indicated that ~60% of the starting material was converted to the desired product. In an effort to drive the reaction to completion a pre-stirred solution of (1R)-1-cyclopropylethanamine (150 μL) and 2.0 M trimethylaluminum in toluene (800 μL) in 1,2-dichloroethane (2 mL) was added via syringe to the reaction mixture at room temperature. The reaction mixture was then heated to 70° C. and stirred for 16 h. LCMS data indicated that the majority of the starting material was converted to the desired product. Upon cooling to room temperature, the reaction mixture was diluted with dichloromethane (5 mL) and DOWEX 50WX8-400 ion-exchange resin was carefully added and the reaction mixture was stirred for 30 min. The inorganics were filtered off and thoroughly washed with dichloromethane. The filtrate was concentrated under reduced pressure and the residue was purified by flash chromatography on a silica gel column with methanol in dichloromethane (0-5%) to afford the desired product (100 mg). The product was dissolved in dichloromethane (4 mL) and TFA (4 mL) and was stirred at room temperature for 1.5 h. The volatiles were removed under reduced pressure and the residue was azeotropically washed with acetonitrile (3×3 mL). The resulting residue was dissolved in methanol (4 mL) and $NH_4OH$ aqueous solution (1 mL) was added and the reaction mixture was stirred at room temperature for 1 h. The crude reaction mixture was concentrated under reduced pressure and subjected to flash chromatography on a silica gel column with methanol in dichloromethane (0-10%) to afford the desired product. The product was dissolved in acetonitrile (15 mL) and cooled to 0° C. prior to the addition of trifluoroacetic acid (0.08 mL). The reaction mixture was allowed to warm to ambient temperature while stirring for 30 min. Water (10 mL) was added and the solution was frozen and subjected to lyophilization to afford the desired product as the corresponding trifluoroacetic acid salt as a white solid. LCMS $(M+H)^+$: m/z=485.5. $^1H$ NMR (500 MHz, $CD_3OD$): δ 9.02 (s, 1H), 8.85 (s, 1H), 8.53 (s, 1H), 7.78 (d, J=3.7 Hz, 1H), 7.67 (t, J=8.5 Hz, 1H), 7.26 (d, J=3.7 Hz, 1H), 6.47 (dd, J=8.6, 2.0 Hz, 1H), 6.40 (dd, J=13.5, 1.9 Hz, 1H), 4.61 (d, J=8.7 Hz, 2H), 4.44 (d, J=8.7 Hz, 2H), 3.67 (s, 2H), 3.51 (p, J=6.8 Hz, 1H), 1.29 (d, J=6.7 Hz, 3H), 0.98 (ddt, J=13.2, 8.3, 4.2 Hz, 1H), 0.54 (td, J=8.4, 4.5 Hz, 1H), 0.47 (tt, J=8.9, 5.3 Hz, 1H), 0.37 (dq, J=9.8, 5.0 Hz, 1H), 0.26 (dq, J=9.5, 4.9 Hz, 1H).

Example 40. 5-{3-(Cyanomethyl)-3-[4-(1H-pyrrolo[2,3-b]pyridin-4-yl)-1H-pyrazol-1-yl]azetidin-1-yl}-N-[1-(trifluoromethyl)cyclopropyl]pyridine-2-carboxamide

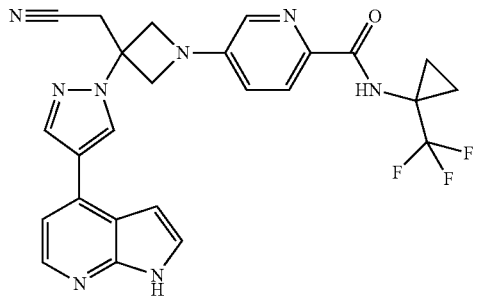 [SMILES: N#CCC1(n2cc(-c3ccnc4[nH]ccc34)cn2)CN(c2ccc(C(=O)NC3(C(F)(F)F)CC3)nc2)C1]

Step 1: tert-butyl 3-(cyanomethyl)-3-[4-(4,4,5,5-tetramethyl-1,3,2-dioxaborolan-2-yl)-1H-pyrazol-1-yl]azetidine-1-carboxylate A mixture of 4-(4,4,5,5-tetramethyl-1,3,2-dioxaborolan-2-yl)-1H-pyrazole (2.0 g, 10. mmol), tert-butyl 3-(cyanomethylene)azetidine-1-carboxylate (2.0 g, 10. mmol) (Example 2, Step 2) and 1,8-diazabicyclo[5.4.0]undec-7-ene (1 mL, 7 mmol) in acetonitrile (3 mL) was stirred at 50° C. overnight. After cooling the mixture was concentrated under reduced pressure. The residue was purified by flash chromatography on a silica gel column with ethyl acetate in hexane (0-50%) to afford the desired product (quantitative). LCMS $(M+Na)^+$: m/z=411.2; $(M-C4H9)^+$: m/z=333.1.

Step 2: tert-butyl 3-(cyanomethyl)-3-[4-(1-{[2-(trimethylsilyl)ethoxy]methyl}-1H-pyrrolo[2,3-b]pyridin-4-yl)-1H-pyrazol-1-yl]azetidine-1-carboxylate A mixture of 4-bromo-1-{[2-(trimethylsilyl)ethoxy]methyl}-1H-pyrrolo[2,3-b]pyridine (1.0 g, 3.0 mmol), tert-butyl 3-(cyanomethyl)-3-[4-(4,4,5,5-tetramethyl-1,3,2-dioxaborolan-2-yl)-1H-pyrazol-1-yl]azetidine-1-carboxylate (1.2 g, 3.0 mmol), tetrakis(triphenylphosphine)palladium(0) (200 mg, 0.2 mmol) and cesium carbonate (3.0 g, 9.2 mmol) in 1,4-dioxane (6 mL) and water (0.9 mL) was degassed and sealed. It was stirred at 90° C. for 2 h. After cooling it was concentrated under reduced pressure. The residue was purified by flash chromatography on a silica gel column with ethyl acetate in hexane (0-50%) to afford the desired product (1.6 g). LCMS $(M+H)^+$: m/z=509.3.

Step 3: {3-[4-(1-{[2-(Trimethylsilyl)ethoxy]methyl}-1H-pyrrolo[2,3-b]pyridin-4-yl)-1H-pyrazol-1-yl]azetidin-3-yl}acetonitrile To a solution of tert-butyl 3-(cyanomethyl)-3-[4-(1-{[2-(trimethylsilyl)ethoxy]methyl}-1H-pyrrolo[2,3-b]pyridin-4-yl)-1H-pyrazol-1-yl]azetidine-1-carboxylate (1.6 g) in methylene chloride (10 mL) was added a solution of 4.0 M of hydrogen chloride in dioxane (20 mL). The mixture was stirred at room temperature overnight. Then it was concentrated under reduced pressure to afford the desired compound as HCl salt (1.5 g). LCMS $(M+H)^+$: m/z=409.2.

Step 4: 5-bromo-N-[1-(trifluoromethyl)cyclopropyl]pyridine-2-carboxamide

A mixture of 5-bromopyridine-2-carboxylic acid (150 mg, 0.74 mmol), 1-(trifluoromethyl)cyclopropanamine (93 mg, 0.74 mmol) (Oakwood, Cat.#: 038175), benzotriazol-1-yloxytris(dimethylamino)phosphonium hexafluorophosphate (345 mg, 0.780 mmol) and triethylamine (310 μL, 2.2 mmol) in methylene chloride (1 mL) was stirred at room temperature for 3 h. The mixture was concentrated under reduced pressure. The residue was purified by flash chromatography on a silica gel column with methanol in dichloromethylene (0-5%) to afford the desired product (124 mg). LCMS $(M+H)^+$: m/z=309.0.

Step 5: 5-{3-(Cyanomethyl)-3-[4-(1H-pyrrolo[2,3-b]pyridin-4-yl)-1H-pyrazol-1-yl]azetidin-1-yl}-N-[1-(trifluoromethyl)cyclopropyl]pyridine-2-carboxamide A mixture of {3-[4-(1-{[2-(trimethylsilyl)ethoxy]methyl}-1H-pyrrolo[2,3-b]pyridin-4-yl)-1H-pyrazol-1-yl]

azetidin-3-yl}acetonitrile HCl salt (40 mg, 0.08 mmol), 5-bromo-N-[1-(trifluoromethyl)cyclopropyl]pyridine-2-carboxamide 26 mg, 0.083 mmol), cesium carbonate (81 mg, 0.25 mmol), (R)-(+)-2,2'-bis(diphenylphosphino)-1,1'-binaphthyl (5.2 mg, 0.0083 mmol) and palladium acetate (1.9 mg, 0.0083 mmol) in toluene (1 mL) was stirred at 105° C. overnight. After the reaction mixture was cooled to room temperature, the solid was separated, and washed with ethyl acetate twice. The combined organic solution was concentrated under reduced pressure. The residue was dissolved in a solution of trifluoroacetic acid (1 mL) in methylene chloride (1:1, 1 mL). After stirred at room temperature for 1.5 h., the mixture was concentrated under reduced pressure. The residue was dissolved in methanol (1 mL). To the solution was added ethylenediamine (0.6 mL). The mixture was stirred at room temperature for 2 h. The product was purified with RP-HPLC (pH=2) to afford the desired product (3.4 mg) as TFA salt. LCMS (M+H)$^+$: m/z=507.2. $^1$H NMR (500 MHz, DMSO-d$_6$): δ 11.98 (s, 1H), 9.04 (s, 1H), 8.89 (s, 1H), 8.39 (s, 1H), 8.26 (d, J=5.3 Hz, 1H), 7.93 (d, J=2.6 Hz, 1H), 7.88 (d, J=8.6 Hz, 1H), 7.63-7.57 (m, 1H), 7.45 (d, J=5.3 Hz, 1H), 7.09 (dd, J=8.5, 2.7 Hz, 1H), 6.99 (dd, J=3.2, 1.4 Hz, 1H), 4.68 (d, J=8.9 Hz, 2H), 4.42 (d, J=8.9 Hz, 2H), 3.75 (s, 2H), 1.32-1.23 (m, 2H), 1.22-1.12 (m, 2H).

Example 41. 5-{3-(Cyanomethyl)-3-[4-(1H-pyrrolo[2,3-b]pyridin-4-yl)-1H-pyrazol-1-yl]azetidin-1-yl}-N-[(1S)-1-cyclopropylethyl]pyrazine-2-carboxamide

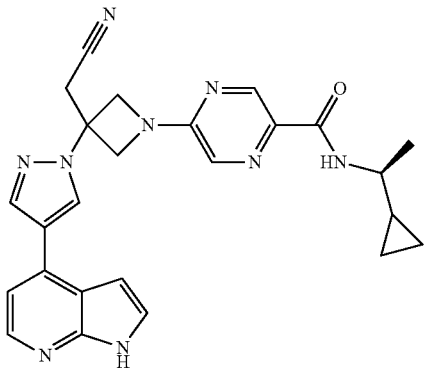 [SMILES: C[C@H](NC(=O)c1cnc(N2CC(CC#N)(n3cc(-c4ccnc5[nH]ccc45)cn3)C2)cn1)C1CC1]

Step 1: 5-Chloro-N-[(1S)-1-cyclopropylethyl]pyrazine-2-carboxamide

A mixture of 5-chloropyrazine-2-carboxylic acid (0.5 g, 3 mmol), (1S)-1-cyclopropylethanamine (0.30 g, 3.5 mmol), N,N,N',N'-tetramethyl-O-(7-azabenzotriazol-1-yl)uronium hexafluorophosphate (1.8 g, 4.7 mmol) and N,N-diisopropylethylamine (1.6 mL, 9.5 mmol) in methylene chloride (5 mL) was stirred at room temperature overnight (22 h.). The mixture was concentrated under reduced pressure. The residue was was purified by flash chromatography on a silica gel column with methanol in dichloromethylene (0-5%) to afford the desired product (0.54 g). LCMS (M+H)$^+$: m/z=226.1.

Step 2: 5-{3-(cyanomethyl)-3-[4-(1-{[2-(trimethylsilyl)ethoxy]ethyl}-1H-pyrrolo[2,3-b]pyridin-4-yl)-1H-pyrazol-1-yl]azetidin-1-yl}-N-[(1S)-1-cyclopropylethyl]pyrazine-2-carboxamide A mixture of {3-[4-(1-{[2-(trimethylsilyl)ethoxy]methyl}-1H-pyrrolo[2,3-b]pyridin-4-yl)-1H-pyrazol-1-yl]azetidin-3-yl}acetonitrile HCl salt (200 mg, 0.4 mmol) (Example 40, Step 3), 5-chloro-N-[(1S)-1-cyclopropylethyl]pyrazine-2-carboxamide (100 mg, 0.46 mmol) in N,N-diisopropylethylamine (0.7 mL, 4 mmol) in a sealed vial was stirred at 120° C. for 1.5 h. After cooling it was concentrated under reduced pressure. The residue was purified by flash chromatography on a silica gel column with methanol in methylene chloride (0-5%) to afford the desired product (0.23 g).

Step 3: 5-{3-(cyanomethyl)-3-[4-(1H-pyrrolo[2,3-b]pyridin-4-yl)-1H-pyrazol-1-yl]azetidin-1-yl}-N-[(1S)-1-cyclopropylethyl]pyrazine-2-carboxamide 5-{3-(Cyanomethyl)-3-[4-(1-{[2-(trimethylsilyl)ethoxy]methyl}-1H-pyrrolo[2,3-b]pyridin-4-yl)-1H-pyrazol-1-yl]azetidin-1-yl}-N-[(1S)-1-cyclopropylethyl]pyrazine-2-carboxamide (0.23 g) was dissolved in a solution of trifluoroacetic acid (2 mL) and methylene chloride (2 mL). The mixture was stirred at room temperature for 2 h, and concentrated to dryness under reduced pressure. The residue was purified by flash chromatography on a silica gel column with methanol in methylene chloride (0-5%) to afford an intermediate which was dissolved in methanol (3.0 mL). To the solution was added ethylenediamine (1.0 mL). The mixture was stirred at room temperature for 2 h. The mixture was concentrated under reduced pressure. The residue was purified by flash chromatography on a silica gel column with methanol in methylene chloride (0-5%) to afford the desired product (0.13 g). LCMS (M+H)$^+$: m/z=468.5. $^1$H NMR (500 MHz, DMSO-d$_6$): δ 12.13 (s, 1H), 8.96 (s, 1H), 8.65 (d, J=1.3 Hz, 1H), 8.44 (s, 1H), 8.30 (d, J=5.5 Hz, 1H), 8.20 (d, J=8.7 Hz, 1H), 8.00 (d, J=1.3 Hz, 1H), 7.67-7.61 (m, 1H), 7.52 (d, J=5.5 Hz, 1H), 7.09-7.04 (m, 1H), 4.82 (d, J=9.7 Hz, 2H), 4.56 (d, J=9.7 Hz, 2H), 3.77 (s, 2H), 3.50-3.28 (m, 1H), 1.22 (d, J=6.7 Hz, 3H), 1.15-0.98 (m, 1H), 0.49-0.39 (m, 1H), 0.39-0.30 (m, 1H), 0.29-0.22 (m, 1H), 0.22-0.15 (m, 1H).

Example 42. 5-{3-(Cyanomethyl)-3-[4-(1H-pyrrolo[2,3-b]pyridin-4-yl)-1H-pyrazol-1-yl]azetidin-1-yl}-N-[(1S)-1-cyclopropyl-2,2,2-trifluoroethyl]pyrazine-2-carboxamide

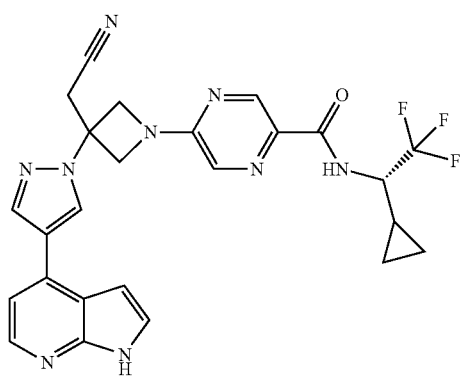 [SMILES: N#CCC1(n2cc(-c3ccnc4[nH]ccc34)cn2)CN(c2cnc(C(=O)N[C@@H](C3CC3)C(F)(F)F)cn2)C1]

Step 1: {3-[4-(4,4,5,5-tetramethyl-1,3,2-dioxaborolan-2-yl)-1H-pyrazol-1-yl]azetidin-3-yl}acetonitrile A mixture of tert-butyl 3-(cyanomethyl)-3-[4-(4,4,5,5-tetramethyl-1,3,2-dioxaborolan-2-yl)-1H-pyrazol-1-yl]azetidine-1-carboxylate (1.5 g, 3.9 mmol) (Example 40, Step 1) in methylene chloride (15 mL) and 4.0 M hydrogen chloride in dioxane (3.9 mL) was stirred at room temperature over weekend. The mixture was treated with triethylamine (1 mL), and the volatiles were removed under reduced pressure. The residue was purified by flash chromatography on a silica gel column with methanol in methylene chloride (0-5%) to afford the desired product (0.95 g, 85%). LCMS (M+H)$^+$: m/z=289.2.

Step 2: Methyl 5-{3-(cyanomethyl)-3-[4-(4,4,5,5-tetramethyl-1,3,2-dioxaborolan-2-yl)-1H-pyrazol-1-yl]azetidin-1-yl}pyrazine-2-carboxylate A mixture of {3-[4-(4,4,5,5-tetramethyl-1,3,2-dioxaborolan-2-yl)-1H-pyrazol-1-yl]azetidin-3-yl}acetonitrile HCl salt (400. mg, 1.23 mmol), methyl 5-chloropyrazine-2-carboxylate (223 mg, 1.29 mmol), cesium carbonate (800 mg, 2.5 mmol), palladium acetate (28 mg, 0.12 mmol) and (S)-(−)-2,2'-bis(diphenylphosphino)-1,1'-binaphthyl (150 mg, 0.25 mmol) in toluene (5 mL) was stirred at 100° C. for 3 h. After the reaction mixture was cooled to room temperature, the solid was separated, and washed with ethyl acetate twice. The filtrate was concentrated under reduced pressure. The residue was purified by flash chromatography on a silica gel column with methanol in methylene chloride (0-5%) to afford the desired product (0.28 g). LCMS (M+H)$^+$: m/z=425.2.

Step 3: Methyl 5-{3-(cyanomethyl)-3-[4-(1H-pyrrolo[2,3-b]pyridin-4-yl)-1H-pyrazol-1-yl]azetidin-1-yl}pyrazine-2-carboxylate A mixture of methyl 5-{3-(cyanomethyl)-3-[4-(4,4,5,5-tetramethyl-1,3,2-dioxaborolan-2-yl)-1H-pyrazol-1-yl]azetidin-1-yl}pyrazine-2-carboxylate (0.28 g, 0.66 mmol), 4-bromo-1H-pyrrolo[2,3-b]pyridine (0.14 g, 0.72 mmol), tetrakis(triphenylphosphine)palladium(0) (0.04 g, 0.03 mmol) and sodium bicarbonate (0.28 g, 3.3 mmol) in a solution of water (0.5 mL) and 1,4-dioxane (1 mL) was degassed for a while and sealed. The mixture was stirred at 85° C. for 3 h. After cooling the mixture was diluted with ethyl acetate. The organic solution was washed with water and brine, dried over Na$_2$SO$_4$. After filtration the filtrate was concentrated under reduced pressure. The residue was purified by flash chromatography on a silica gel column with methanol in methylene chloride (0-5%) to afford the desired product (0.15 g). LCMS (M+H)$^+$: m/z=415.2.

Step 4: 5-{3-(cyanomethyl)-3-[4-(1H-pyrrolo[2,3-b]pyridin-4-yl)-1H-pyrazol-1-yl]azetidin-1-yl}pyrazine-2-carboxylic acid A mixture of methyl 5-{3-(cyanomethyl)-3-[4-(1H-pyrrolo[2,3-b]pyridin-4-yl)-1H-pyrazol-1-yl]azetidin-1-yl}pyrazine-2-carboxylate (0.15 g, 0.36 mmol) and lithium hydroxide monohydrate (46 mg, 1.1 mmol) in methanol (3 mL) and water (1 mL) was stirred at room temperature for 2 h. The mixture was concentrated under reduced pressure to afford the desired product (quantitative) which was directly used in the next step reaction without further purification.

Step 5: 5-{3-(cyanomethyl)-3-[4-(1H-pyrrolo[2,3-b]pyridin-4-yl)-1H-pyrazol-1-yl]azetidin-1-yl}-N-[(1S)-1-cyclopropyl-2,2,2-trifluoroethyl]pyrazine-2-carboxamide A mixture of 5-{3-(cyanomethyl)-3-[4-(1H-pyrrolo[2,3-b]pyridin-4-yl)-1H-pyrazol-1-yl]azetidin-1-yl}pyrazine-2-carboxylic acid (10 mg, 0.02 mmol), (1S)-1-cyclopropyl-2,2,2-trifluoroethanamine HCl salt (6.6 mg, 0.037 mmol), benzotriazol-1-yloxytris(dimethylamino)phosphonium hexafluorophosphate (12 mg, 0.027 mmol) and triethylamine (16 µL, 0.11 mmol) in N,N-dimethylformamide (0.3 mL) was stirred at room temperature for 3 h. It was diluted with methanol, purified by RP-HPLC (pH=2) to afford the desired product (2.9 mg) as TFA salt. LCMS (M+H)$^+$: m/z=522.4. $^1$H NMR (500 MHz, DMSO-d$_6$): δ 12.01 (s, 1H), 8.92 (s, 1H), 8.90 (d, J=9.4 Hz, 1H), 8.69 (d, J=1.1 Hz, 1H), 8.41 (s, 1H), 8.27 (d, J=5.3 Hz, 1H), 8.04 (d, J=1.0 Hz, 1H), 7.65-7.57 (m, 1H), 7.46 (d, J=5.3 Hz, 1H), 7.01 (s, 1H), 4.84 (d, J=9.8 Hz, 2H), 4.58 (d, J=9.8 Hz, 2H), 4.10-3.97 (m, 1H), 3.78 (s, 2H), 1.46-1.33 (m, 1H), 0.73-0.61 (m, 1H), 0.61-0.53 (m, 1H), 0.53-0.44 (m, 1H), 0.27-0.17 (m, 1H).

Example A: In Vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). IC$_{50}$s of compounds were measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM IC$_{50}$ measurements, ATP concentration in the reactions was 1 mM. Reactions were carried out at room temperature for 1 hour and then stopped with 20 µL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). See Table 1 for data related to compounds of the examples.

TABLE 1

IC$_{50}$ data for JAK enzyme assay (at 1 mM ATP)

| Example No. | JAK1 IC$_{50}$ (nM)* | JAK2 IC$_{50}$ (nM)* | JAK2/JAK1** |
|---|---|---|---|
| 1 | + | ++ | A |
| 2 | + | + | A |
| 3 | + | + | A |
| 4 | + | + | A |
| 5 | + | + | A |
| 6 | + | + | A |
| 7 | + | + | A |
| 8 | + | + | A |
| 9 | + | + | A |
| 10 | + | + | A |
| 11 | + | + | A |
| 12 | + | + | A |
| 13 | + | ++ | A |
| 14 | + | ++ | A |
| 15 | + | ++ | A |
| 16 | + | + | A |
| 17 | + | + | A |
| 18 | + | ++ | A |
| 19 | + | ++ | A |
| 20 | + | ++ | A |
| 21 | + | + | A |
| 22 | + | ++ | A |

TABLE 1-continued

IC$_{50}$ data for JAK enzyme assay (at 1 mM ATP)

| Example No. | JAK1 IC$_{50}$ (nM)* | JAK2 IC$_{50}$ (nM)* | JAK2/JAK1** |
|---|---|---|---|
| 23 | + | ++ | A |
| 24 | + | + | A |
| 25 | + | + | A |
| 26 | + | ++ | A |
| 27 | + | + | A |
| 28 | + | + | A |
| 29 | + | + | A |
| 30 | + | ++ | A |
| 31 | + | + | A |
| 32 | + | + | A |
| 33 | + | ++ | A |
| 34 | + | ++ | A |
| 35 | + | ++ | A |
| 36 | + | ++ | A |
| 37 | + | + | A |
| 38 | + | ++ | A |
| 39 | + | ++ | A |
| 40 | + | ++ | A |
| 41 | + | ++ | A |
| 42 | + | ++ | A |

*10 nM or less (+); >10 nM to 40 nM (++)
**A means greater than or equal to 10

Example B: Cellular Assays

Cancer cell lines dependent on cytokines and hence JAK/STAT signal transduction, for growth, can be plated at 6000 cells per well (96 well plate format) in RPMI 1640, 10% FBS, and 1 nG/mL of appropriate cytokine. Compounds can be added to the cells in DMSO/media (final concentration 0.2% DMSO) and incubated for 72 hours at 37° C., 5% $CO_2$. The effect of compound on cell viability is assessed using the CellTiter-Glo Luminescent Cell Viability Assay (Promega) followed by TopCount (Perkin Elmer, Boston, Mass.) quantitation. Potential off-target effects of compounds are measured in parallel using a non-JAK driven cell line with the same assay readout. All experiments are typically performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. Nature 434:1144-1148; Staerk, J., et al. JBC 280:41893-41899). Endpoints include the effects of compounds on cell survival, proliferation, and phosphorylated JAK, STAT, Akt, or Erk proteins.

Certain compounds herein can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 µg/ml streptomycin) at a density of 2×10$^6$ cells/ml at 37° C. for up to 2 days. For IL-2 stimulated cell proliferation analysis, T-cells are first treated with Phytohemagglutinin (PHA) at a final concentration of 10 µg/mL for 72 hours. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C: In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. Hematol J. 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

Example D: Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (Immunol Today. 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 µL (10 µL on the internal pinna and 10 µL on the external pinna) at a concentration of 0.2%. Twenty-four to seventy-two hours after the challenge, ears are measured again. Treatment with the test compounds is given throughout the sensitization and challenge phases (day −1 to day 7) or prior to and throughout the challenge phase (usually afternoon of day 4 to day 7). Treatment of the test compounds (in different concentration) is administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E: In Vivo Anti-Inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press; *Methods in Molecular Biology*: Vol. 225, Inflammation Protocols., Winyard, P. G. and Willoughby, D. A., Humana Press, 2003.).

Example F: Animal Models for the Treatment of Dry Eye, Uveitis, and Conjunctivitis Agents may be evaluated in one or more preclinical models of dry eye known to those schooled in the art including, but not limited to, the rabbit concanavalin A (ConA) lacrimal gland model, the scopolamine mouse model (subcutaneous or transdermal), the Botulinumn mouse lacrimal gland model, or any of a number of spontaneous rodent autoimmune models that result in ocular gland dysfunction (e.g. NOD-SCID, MRL/lpr, or NZB/NZW) (Barabino et al., Experimental Eye Research 2004, 79, 613-621 and Schrader et al., Developmental Opthalmology, Karger 2008, 41, 298-312, each of which is incorporated herein by reference in its entirety). Endpoints in these models may include histopathology of the ocular glands and eye (cornea, etc.) and possibly the classic Schirmer test or modified versions thereof (Barabino et al.) which measure tear production. Activity may be assessed by dosing via multiple routes of administration (e.g. systemic or topical) which may begin prior to or after measurable disease exists.

Agents may be evaluated in one or more preclinical models of uveitis known to those schooled in the art. These include, but are not limited to, models of experimental autoimmune uveitis (EAU) and endotoxin induced uveitis (EIU). EAU experiments may be performed in the rabbit, rat, or mouse and may involve passive or activate immunization. For instance, any of a number or retinal antigens may be used to sensitize animals to a relevant immunogen after which animals may be challenged ocuarly with the same antigen. The EIU model is more acute and involves local or systemic administration of lipopolysaccaride at sublethal doses. Endpoints for both the EIU and EAU models may include fundoscopic exam, histopathology amongst others. These models are reviewed by Smith et al. (Immunology and Cell Biology 1998, 76, 497-512, which is incorporated herein by reference in its entirety). Activity is assessed by dosing via multiple routes of administration (e.g. systemic or topical) which may begin prior to or after measurable disease exists. Some models listed above may also develop scleritis/episcleritis, chorioditis, cyclitis, or iritis and are therefore useful in investigating the potential activity of compounds for the therapeutic treatment of these diseases.

Agents may also be evaluated in one or more preclinical models of conjunctivitis known those schooled in the art. These include, but are not limited to, rodent models utilizing guinea-pig, rat, or mouse. The guinea-pig models include those utilizing active or passive immunization and/or immune challenge protocols with antigens such as ovalbumin or ragweed (reviewed in Groneberg, D. A., et al., Allergy 2003, 58, 1101-1113, which is incorporated herein by reference in its entirety). Rat and mouse models are similar in general design to those in the guinea-pig (also reviewed by Groneberg). Activity may be assessed by dosing via multiple routes of administration (e.g. systemic or topical) which may begin prior to or after measurable disease exists. Endpoints for such studies may include, for example, histological, immunological, biochemical, or molecular analysis of ocular tissues such as the conjunctiva.

Example G: In Vivo Protection of Bone

Compounds may be evaluated in various preclinical models of osteopenia, osteoporosis, or bone resorption known to those schooled in the art. For example, ovariectomized rodents may be used to evaluate the ability of compounds to affect signs and markers of bone remodeling and/or density (W. S. S. Jee and W. Yao, J Musculoskel. Nueron. Interact., 2001, 1(3), 193-207, which is incorporated herein by reference in its entirety). Alternatively, bone density and architecture may be evaluated in control or compound treated rodents in models of therapy (e.g. glucocorticoid) induced osteopenia (Yao, et al. Arthritis and Rheumatism, 2008, 58(6), 3485-3497; and id. 58(11), 1674-1686, both of which are incorporated herein by reference in its entirety). In addition, the effects of compounds on bone resorption and density may be evaluable in the rodent models of arthritis discussed above (Example E). Endpoints for all these models may vary but often include histological and radiological assessments as well as immunohisotology and appropriate biochemical markers of bone remodeling.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound, which is 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide, or a pharmaceutically acceptable salt thereof.

2. A composition comprising a compound according to claim 1, or a pharmaceutically acceptable salt thereof, and a pharmaceutically acceptable carrier.

3. A method of inhibiting an activity of JAK1 comprising contacting JAK1 with a compound according to claim 1, or a pharmaceutically acceptable salt thereof.

4. The method according to claim 3, wherein said compound, or pharmaceutically acceptable salt thereof, is selective for JAK1 over JAK2.

5. A method of ameliorating or inhibiting an autoimmune diseas in a patient in need thereof, comprising administering to said patient a therapeutically effective amount of the compound of claim 1, or a pharmaceutically acceptable salt thereof.

6. The method according to claim 5, wherein the autoimmune disease is a skin disorder.

7. The method according to claim 6, wherein the skin disorder is atopic dermatitis.

8. The method according to claim 5, wherein the autoimmune disease is multiple sclerosis.

9. The method according to claim 5, wherein the autoimmune disease is rheumatoid arthritis.

10. The method according to claim 5, wherein the autoimmune disease is type I diabetes.

11. The method according to claim 5, wherein the autoimmune disease is lupus.

12. The method according to claim 5, wherein the autoimmune disease is inflammatory bowel disease.

13. The method according to claim 5, wherein the autoimmune disease is Crohn's disease.

14. The method according to claim 5, wherein the autoimmune disease is myasthenia gravis.

15. The method according to claim 5, wherein the autoimmune disease is immunoglobulin nephropathies.

16. The method according to claim 5, wherein the autoimmune disease is myocarditis.

17. The method according to claim 5, wherein the autoimmune disease is autoimmune thyroid disorder.

18. The method according to claim 6, wherein the skin disorder is psoriasis.

19. The method according to claim 6, wherein the skin disorder is skin sensitization.

20. The method according to claim 6, wherein the skin disorder is skin irritation.

21. The method according to claim 6, wherein the skin disorder is skin rash.

22. The method according to claim 6, wherein the skin disorder is contact dermatitis.

23. The method according to claim 6, wherein the skin disorder is allergic contact sensitization.

24. The method according to claim 5, wherein the autoimmune disease is psoriatic arthritis.

25. The method according to claim 5, wherein the autoimmune disease is juvenile arthritis.

* * * * *

UNITED STATES PATENT AND TRADEMARK OFFICE
CERTIFICATE OF CORRECTION

PATENT NO. : 10,513,522 B2
APPLICATION NO. : 15/435735
DATED : December 24, 2019
INVENTOR(S) : Wenqing Yao, David M. Burns and Jincong Zhuo Page 1 of 1

It is certified that error appears in the above-identified patent and that said Letters Patent is hereby corrected as shown below:

In the Claims

Column 97, Line 42, Claim 5, delete "diseas" and insert -- disease --.

Signed and Sealed this
Twelfth Day of May, 2020

Andrei Iancu
*Director of the United States Patent and Trademark Office*